US006852529B1

(12) United States Patent (10) Patent No.: US 6,852,529 B1
Cooper et al. (45) Date of Patent: Feb. 8, 2005

(54) GLOUCOSE-REGULATED MRNA INSTABILITY ELEMENT

(75) Inventors: Denise R. Cooper, St. Petersburg, FL (US); Niketa A. Patel, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/435,471

(22) Filed: Nov. 8, 1999

(51) Int. Cl.[7] .......................... C07H 21/04; C12N 5/00; C12N 5/02; C12N 15/00; C12Q 1/68
(52) U.S. Cl. .............................. 435/325; 435/4; 435/6; 435/320.1; 435/455; 536/24.1
(58) Field of Search ............................ 435/4, 6, 320.1, 435/325, 455; 536/24.1, 24.31, 24.33

(56) References Cited

U.S. PATENT DOCUMENTS 5,703,054 A * 12/1997 Bennett et al. ................ 514/44
5,795,961 A * 8/1998 Wallace et al. ............. 530/350

OTHER PUBLICATIONS

GenBank Accession No. AA875851 (Mar. 25, 1998) Alignment with SEQ ID NO.: 9.*
Patel, N.A. et al. "The protein kinase C βII exon confers mRNA Instability in the presence of high glucose concentrations" *J. Biol. Chem.*, 2003, 278(2):1149–1157.
Patel, N.A. et al. "Phosphoinosilide 3–kinase mediates protein kInase C βII mRNA destabilization in rat A10 smooth muscle cell cultures exposed to high glucose" *Arch. Biochem. Biophysics.*, 2002, 403:111–120.
Yamamoto, M. et al. "A shift from normal to high glucose levels stimulates cell proliferation in drug sensitive MCF–7 human breast cancer cells but not in multidrug resistant MCF–7/ADR cells which overproduce PKC–βII" *Int. J. Cancer*, 1999, Sep. 83(1):98–106.
Amara, F.M. et al. "Defining a Novel cis–Element in the 3'–Untranslated Region of Mammalian Ribonucleotide Reductase Component R2 mRNA" *J. Biol. Chem.*, Aug. 1996, 271(33):20126–20131.
Blobe, G.C. et al. "Protein Kinase C βII Specifically Binds to and Is Activated by F–actin" *J. Biol. Chem.*, Jun. 1996, 271(26):15823–15830.
Cañete–Soler, R. et al. "Characterization of Ribonucleoprotein Complexes and Their Binding Sites on the Neurofilament Light Subunit mRNA" *J. Biol. Chem.*, May 1998, 273(20):12655–12661.
Chalfant, C.E. et al. "Regulation of Alternative Splicing of Protein Kinase Cβ by Insulin" *J. Biol. Chem.*, Jun. 1995, 270(22):13326–13332.
Hara, K. et al. "1–Phosphatidylinositol 3–kinase activity is required for insulin–stimulated glucose transport but not in RAS activation in CHO cells" *Proc. Natl. Acad. Sci., USA*, Aug. 1994, 91:7415–7419.

McClain, D.A. et al. "Glucose and glucosamine regulate growth factor gene expression in vascular smooth muscle cells" *Proc. Natl. Acad. Sci., USA*, Sep. 1992, 89:8150–8154.
Nakshatri, H. and P. Bhat–Nakshatri "Multiple parameters determine the specificity of transcriptional response by nuclear receptors HNF–4, ARP–1, PPAR, RAR and RXR through common response elements" *Nucleic Acids Res.*, 1998, 26(10):2491–2499.
Niino, Y.S. et al. "Positive and Negative Regulation of the Transcription of the Human Protein Kinase C β Gene" *J. Biol. Chem.*, Mar. 1992, 267(9):6158–6163.
Obeid, L.M. et al. "Cloning and Characterization of the Major Promoter of the Human Protein Kinase C β Gene" *J. Biol. Chem.*, Oct. 1992, 267(29):20804–20810.
Palmer, R.H. et al. "Activation of PRK1 by Phosphatidylinositol 4,5–Bisphosphate and Phosphatidylinositol 3,4,5–Trisphosphate" *J. Biol. Chem.*, Sep. 1995, 270(38):22412–22416.
Prokipcak, R.D. et al. "Purification and Properties of a Protein That Binds to the C–terminal Coding Region of Human c–myc mRNA" *J. Biol. Chem.*, Mar. 1994, 269(12):9261–9269.
Quilliam, L.A. et al. "Isolation of a NCK–associated Kinase, PRK2, an SH3–binding Protein and Potential Effector of Rho Protein Signaling" *J. Biol. Chem.*, Nov. 1996, 271(46):28772–28776.
Ron, D. et al. "Cloning of an intracellular receptor for protein kinase C: A homolog of the β subunit of G proteins" *Proc. Natl. Acad. Sci. USA*, Feb. 1994, 91:839–843.
Ross, J. "mRNA Stability in Mammalian Cells" *Microbiology Reviews*, Sep 1995, 59(3):423–450.
Sayeski, P.P. and J.E. Kudlow "Glucose Metabolism to Glucosamine is Necessary for Glucose Stimulation of Transforming Growth Factor–α Gene Transcription" *J. Biol. Chem.*, Jun. 1996, 271(25):15237–15243.
Vincent, S. and Settleman, J. "The PRK2 Kinase Is a Potential Effector Target of both Rho and Rac GTPases and Regulates Actin Cytoskeletal Organization" *Mol. Cell. Biol.*, Apr. 1997, 17(4):2247–2256.

(List continued on next page.)

*Primary Examiner*—Anne-Marie Falk
(74) *Attorney, Agent, or Firm*—Saliwanchik, Lloyd & Saliwanchik

(57) ABSTRACT

The subject invention pertains to nucleic acid constructs for post-transcriptional control of expression of a ploynucleotide encoding a protein in a eukaryotic cell, wherein the constructs include a metabolite responsive instability element such as the glucose-regulated mRNA instability element. The subject invention further pertains to host cells and vectors comprising the nucleic acid constructs of the invention, as well as probes, methods, and kits for detecting metabolite responsive instability elements or mutations thereof.

13 Claims, 23 Drawing Sheets

OTHER PUBLICATIONS

Amano, M. et al. "Identification of a Putative Target for Rho as the Serine–Threonine Kinase Protein Kinase, N" *Science*, Feb. 1996, 271(5249):648–650.

Amara, F.M. et al. "A cis–trans Interaction at the 3'–Untranslated Region of Ribonucleotide Reductase mRNA is Regulated by TGF–$\beta_1$, TGF–$\beta_2$, and TGF–$\beta_3$" *Biochem. and Biophysical Res. Comm.*, 1996, 228:347–351.

Benbow, U. and C.E. Brinckerhoff "The AP–1 Site and MMP Gene Regulation: What Is All the Fuss About ?" *Matrix Biology*, 1997, 15:519–526.

Bernstein, P.L. et al. "Control of c–myc mRNA half–life in vitro by a protein capable of binding to a coding region stability determinant" *Genes Dev.*, 1992, 6:642–654.

Chung, J. et al. "PDGF— and insulin–dependent $pp70^{S6K}$ activation mediated by phosphatidylinositol–3–OH kinase" *Nature*, Jul. 1994, 370:71–75.

Hansen, W.R. et al. "The 3'–nontranslated region of rat renal glutaminase mRNA contains a pH–responsive stability element" *Amer. J. Physiology*, Jul. 1996, 271:F126–f131.

Jia, Z. "Protein phosphatases: structures and implications" *Biochem. Cell Biol.*, 1997, 75:17–26.

Kemp, B.E. and R.B. Pearson "Protein kinase recognition sequence motifs" *Trends Biochem. Sci.*, Sep. 1990, 15(9):342–346.

Mukai, H. and Y. Ono "A Novel Protein Kinase with Leucine Zipper–Like Sequences: Its Catalytic Domain is Highly Homologous to That of Protein Kinase C" *Biochem. Biophys. Res. Comm.*, Mar. 1994, 199(2):897–904.

Newton, A.C. "Regulation of protein kinase C" *Curr. Opin. Cell Biol.*, 1997, 9:161–167.

Nishizuka, Y. "Studies and Perspectives of Protein Kinase C" *Science*, Jul. 1986, 233(4761):305–312.

Nishizuka, Y. "Intracellular Signaling by Hydrolysis of Phospholipids and Activation of Protein Kinase C" *Science*, Oct. 1992, 258(5082):607–614.

Nishizuka, Y. "Protein kinase C and lipid signaling for sustained cellular responses" *FASEB J.*, 1995, 9:484–496.

Orekhov, A.N. et al. "Cellular Composition of Atherosclerotic and Uninvolved Human Aortic Subendothelial Intima" *Am J. Pathol.*, 1984, 115:17–24.

Palmer, R.H. and P.J. Parker "Expression, purification and characterization of the ubiquitous protein kinase C–related kinase 1" *Biochem. J.*, 1995, 309:315–320.

Patel, N.A. et al. "Acute hyperglycemia regulates transcription and posttranscriptional stability of PKCβII mRNA in vascular smooth muscle cells" *FASEB J.*, 1999, 13:103–113.

Perrotti, D. et al. "TLS/FUS, a pro–oncogene involved in multiple chromosomal translocations, is a novel regulator of BCR/ABL–mediated leukemogenesis" *The EMBO J.*, 1998, 17(15):4442–4455.

Prekeris, R. et al. "Identification and Localization of an Actin–binding Motif That Is Unique to the Epsilon Isoform of Protein Kinase C and Participates in the Regulation of Synaptic Function" *J. Cell. Biol.*, Jan. 1996, 132(1–2):77–90.

Ridley, A.J. et al. "The Small GTP–Binding Protein rac Regulates Growth Factor–Induced Membrane Ruffling" *Cell*, Aug. 1992, 70:401–410.

Ross, R. "The Pathogenesis of Atherosclerosis—An Update" *N. Eng. J. Med.*, Feb. 1986, 314(8):488–500.

Santen, R.J. et al. "Atherosclerosis in Diabetes Mellitus. Correlations With Serum Lipid Levels, Adiposity, and Serum Insulin Level" *Arch. Intern. Med.*, Dec. 1972, 130(6):833–843.

Schwartz, S.M. et al. "Replication of Smooth Muscle Cells in Vascular Disease" *Cir. Res.*, Apr. 1986, 58(4):427–444.

Shiba, T. et al. "Characterization of the Activation of Protein Kinase C Isoenzymes in the Retina of Diabetic Rats" *Diabetes*, 1990, 39(Supplement 1):31A. Abstract No. 123.

Takai, Y. et al. "Studies on a Cyclic Nucleotide–independent Protein Kinase and Its Proenzyme in Mammalian Tissues" *J. Biol. Chem.*, Nov. 1977, 252(21):7603–7609.

Watanabe, G. "Protein Kinase N (PKN) and PKN–Related Protein Rhophilin as Targets of Small GTPase Rho" *Science*, Feb. 1996, 271(5249):645–648.

\* cited by examiner 1 5' cap
2 5' UTR
3 premature stop codons
4 open reading frame sequences
5 3' UTR sequences
6 ARE sequences
7 3' terminal stem loop
8 poly(A) tail

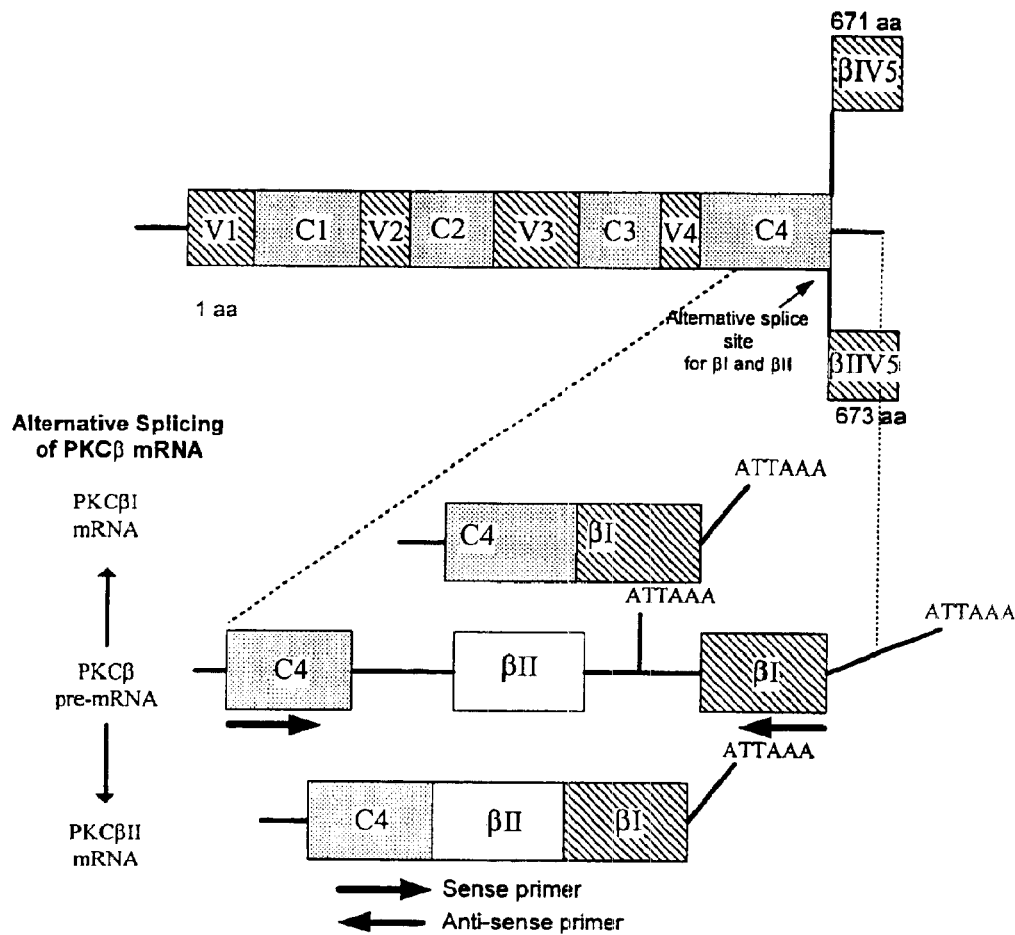

FIG. 25

```
5'TTTTAAACCAAAAGCTTTTTGGGCGAAACGCTGAAACTTC
GACCGGTTTTTCACCCGCCATCCACCAGTCCTAACACCTCC
GACCAGGAAGTCATCAGGAATATTGACCAATCAGAATTCGA
AGGATTTCCTTTGTTAACTCTGAATTTTTAAAACCCGAAGTC
AAGAGCTAGTAGATCTGTAGACCTCCGTCCTTCATTTCTGTC
ATTCAAGCTCACAGCTATCATGAGAGACAAGCGAGACACCT
CCAACTTCGACAAAAGTTCACCAGGCAGCCTGTGGAACTGA
CTCCCACTGACAAACTCTGTCGACTAGAATGCCCTGAATTC
TGCAGATATCCATCACACTGCG 3'
```

FIG. 27

GLOUCOSE-REGULATED MRNA INSTABILITY ELEMENT

BACKGROUND OF INVENTION

Multicellular eukaryotic organisms are capable of responding to extracellular signals to regulate or accentuate gene expression through the process of signal transduction. A large number of the components of the signal transduction pathway are comprised of proteins that are 110 covalently modified by ligands such as hormones, growth factors, cytokines or second messengers like camp, $Ca^{2+}$, diacylglycerol, inositol-3-phosphate and others. This results in the induction of a cascade leading to gene expression in which activation of kinases that phosphorylate tyrosine or serine/threonine residues play central roles. Prominent targets of second messengers are the camp-dependent protein kinase A (PKA) and the $Ca^{2+}$/phospholipid-activated protein kinase C (PKC). The protein kinase C cascade includes several enzymes that are sequentially phosphorylated in response to external stimuli. PKC established its role in signal transduction when it was demonstrated that diacylglycerol, a product of hormone stimulated phosphatidylinositol hydrolysis, was an activator of the enzyme. Multiple lipid pathways contribute to the production of diacylglycerol, the second messenger for PKC. Phorbol esters, which are potent tumor promoters, activate PKC and this discovery led to further excitement in the field (see for example, Nishizuka, 1995, pp.484–496; Nishizuka, 1992, pp.607–614).

Protein kinase C modulates diverse cellular functions such as cell cycle progression and differentiation, apoptosis, and tumor promotion (Nishizuka, 1986, pp.305–312). PKC regulates gene expression via transcription through the activation of cis-elements. It is a mediator of immune responses, hormone secretion and receptor desensitization. Many of these roles are mediated by accentuating membrane structure events. PKC phosphorylates serine or threonine residues at basic sequences with the motif xRxxS/TxRx. Thus histones H1 and IIIS, and protamine, are efficient substrates for PKC. In addition to catalyzing phosphorylation reactions, PKC autophosphorylates in vitro, (on residues Thr-641 and Ser-660 in PKCβII) by an intramolecular mechanism and this may play a role in its proteolytic activation and degradation.

Together with the fact that activation of PKC isozymes is associated with altered gene expression and its presence in the nucleus, it was expected that PKC could phosphoryate some transcription factors and thereby regulate gene expression. PKC phosphorylates CREB, the camp-responsive element-binding protein and as a result CRE binding is enhanced. NF-KB, in the cytosol of resting cells, is in a complex with I-κB. On PKC activation, by phorbol esters, the inhibitory complex dissociates and NF-κB translocates into the nucleus as an active transcription factor. C-jun, a phorbol ester-responsive transcription factor, is also regulated by PKC. Vitamin $D_3$ receptor, a member of the steroid/thyroid hormone family, binds to vitamin $D_3$ and associates with its DNA element thereby altering gene transcription. PKCβ phosphorylates the vitamin $D_3$ receptor, and inhibits transcriptional activation by vitamin $D_3$. TLS/FUS, a DNA-binding nuclear protein, is a regulator of BCR/ABL-mediated leukemogenesis (Perrotti et at., 1998, pp.4442–4455). PKCβII phosphorylates TLS/FUS and regulates its DNA-binding activity in the nucleus.

Historically, Nishizuka et al discovered protein kinase C in rat brain as the proenzyme for a histone protein kinase (see, for example Takai et al., 1977, pp.7603–7609). This protein kinase M (PKM) was generated as a result of partial proteolysis by trypsin or a calcium-dependent protease. From biochemical studies, it was soon established that the proenzyme, PKC, exhibited kinase activity upon membrane association. It is now well established that protein kinase C, a family of serine/threonine kinase isozymes, translocates from the cytosol to another intracellular compartment like the membrane or nucleus in response to stimuli from neurotransmitters, hormones and growth factors. Most PKCs are activated by phosphatidylserine, an acidic lipid located on the cytoplasmic side of the membrane, diacylglycerol and phorbol esters. Some PKC family members also require $Ca^{2+}$ and other lipid second messengers for optimal activity.

Protein Kinase C isozyme family

Biochemical and molecular cloning analysis of protein kinase C revealed a large family of isozymes exhibiting individual characteristics and functions and tissue specific distribution. Protein kinase C isozymes comprise a single polypeptide chain with a 20–70 kDa amino-terminal regulatory domain and an approximately 45 kDa kinase domain at the carboxy-terminus. The PKC isozymes, to date, can be categorized into at least three groups based on their homology and sensitivity to their cofactors (Table 1). The earliest discovered PKC isozymes are the members of convention or classical PKC (cPKC) and include PKCT-α, -βI, -βII (alternatively spliced variants of -β) and -γ. This class of isozymes is activated by diacylglycerol, phosphatidylserine, phorbol esters and $Ca^{2+}$. The novel PKC (nPKC) subfamily of isozymes include PKC-δ, -ε, -η and -θ are calcium-independent. The least understood are the atypical PKC isozymes (aPKC) that are insensitive to phorbol esters but are activated by phosphatidylserine and include PKC-ζ and γ/t. A recently described protein kinase C μ(human) and its murine homolog PKD, form a distinct class in that it is activated by phorbol esters and is phospholipid-dependent, but calcium insensitive. It has a kinase core similar to that of calmodulin-dependent kinases and no pseudosubstrate motif has been identified. However, it contains two unique hydrophobic domains in the N-terminal portion (putative transmembrane sequences) of the enzyme, a plecksterin homology domain and a distinct catalytic domain structure. Another class of PKC, the PKC-related kinases (PRK) consists of three members: PRKs 1, -2 and -3. PRKs are insensitive to $Ca^{2+}$, DAG and phorbol esters (Palmer et al., 1995c, pp.315–320; Mukai et al., 1994b, pp.897–904). PRK family binds to RhoA, which leads to its activation (Vincent et al., 1997, pp.2247–2256; Amano et al., 1996, pp.648–650; Quilliam et al., 1996, pp.28772–28776; Watanbe et al., 1996, pp.645–648).

TABLE 1

PKC Isozyme Family
(Nishizuka, 1986, pp. 305–312; Newton, 1997, pp. 161–167).

| Class | Molecular Weight | Activators |
|---|---|---|
| Conventional PKCs (cPKC) | | |
| α | 76.8 kDa | PS, DAG, $Ca^{2+}$, phorbol esters |
| βI | 76.8 kDa | PS, DAG, $Ca^{2+}$, phorbol esters |
| βII | 76.9 kDa | PS, DAG, $Ca^{2+}$, phorbol esters |
| γ | 78.4 kDa | PS, DAG, $Ca^{2+}$, phorbol esters |

TABLE 1-continued

PKC Isozyme Family
(Nishizuka, 1986, pp. 305–312; Newton, 1997, pp. 161–167).

| Class | Molecular Weight | Activators |
|---|---|---|
| Novel PKCs (NpkC) | | |
| δ | 77.5 kDa | PS, DAG, phorbol esters |
| ε | 83.5 kDa | PS, DAG, phorbol esters |
| η | 78.0 kDa | PS, DAG, phorbol esters |
| θ | 81.6 kDa | PS, DAG, phorbol esters |
| Atypical PKCs (aPKC) | | |
| ζ | 67.7 kDa | PS |
| λ/ι | 67.2 kDa | PS |
| Protein kinase Cμ/ PKD | ? | PS, phorbol esters |

PS, phosphatidyl serine; DAG, diacylglycerol; $Ca^{2+}$, calcium

Structure of Protein Kinase C

Cloning of the cDNA and extensive biochemical and mutational analysis has indicated that the primary amino acid structure of the PKC isozymes is composed of conserved domains (C1–C4), that serve as functional modules, and are separated by variable domains (V1–V5) that contribute to isozyme specificity and function.

The N-terminal regulatory domain and the C-terminal catalytic domain structure of PKC isozymes are diagrammed in FIG. 1. The N-terminal V1 domain of cPKC isozymes is approximately 20 amino acids while that of the nPKC isozymes is longer and may contribute to regulate the functions of the conserved domains. The autoinhibitory domain contains a pseudosubstrate site (at amino acids 22 to 28) that cannot be phosphorylated and blocks the catalytic site. The C1 domain, that immediately follows the pseudosubstrate sequence, binds to diacylglycerol and phorbol esters. It is present as a tandem repeat of two domains in most PKCs except within the atypical PKC isozymes that have only one copy of this domain. The C1 domain contains a cysteine-rich region that comprises of two zinc-finger motifs each with six Cys-residues, that co-ordinates two $Zn^{2+}$ ions, and a DNA-binding motif. No obvious role has yet been elucidated for the $Zn^{2+}$ ions. The C2 domain contains a binding site for acidic lipids and represents the $Ca^{2+}$ binding domain of the $Ca^{2+}$ dependent PKC isozymes (the novel PKC isozymes notably lack this $Ca^{2+}$ binding domain). The V3 or hinge region separates the regulatory and catalytic domains and becomes proteolytically labile when the enzyme translocates to the membrane on activation. On proteolysis, the pseudosubstrate inhibition is relieved which leads to the generation of the constitutively active kinase domain (protein kinase M). The C3 domain contains an ATP-binding motif, $xGxGx_2Gx_{16}Kx$, which is conserved in all protein kinases. The C4 domain contains the substrate-binding site and the phosphate transfer region containing the conserved sequence DFG (Kemp et al., 1990, pp.342–346). The V5 region confers specific function and role to the alternatively spliced PKC13 forms i.e. PKC-βI and -βII. The V5 region is involved in substrate specificity and protein trafficking. Protein kinase C u or PKD has a unique structure in that it contains two hydrophobic domains in the N-terminal (putative transmembrane sequences), a putative pleckstrin homology domain and a distinct catalytic domain.

Tissue, Cellular and Subcellular Localization of PKCs

PKC isozymes show distinct tissue, cellular and subcellular distribution and more than one isoform could be expressed in a cell type (Table 2). PKCα, βI, βII, γ, δ, ε, ζ are expressed in the brain. PKC γ is exclusively expressed in the brain and spinal cord. PKC η, θ and λ are abundant in skin and lung, skeletal muscle, and ovary and testis. This preferential expression could imply tissue specific functions while the ubiquitous expression could suggest that the PKCs are essential for general cell function.

Several PKCs are differentially expressed in various regions and cell types of the brain. PKCγ predominates in the dendrites, cell bodies and axons of Purkinje, PKC α, βI, βII γ are contained in the neurons of the brain. Glial cells also selectively express PKCα and βII.

TABLE 2

| PKC ISOFORMS | TISSUES EXPRESSING HIGHEST LEVELS |
|---|---|
| Conventional PKCs (cPKC) | |
| α | Ubiquitous |
| βI (or β2) | Brian, heart, spleen, vascular smooth muscle |
| βII (or β1) | Brian, heart, spleen, vascular smooth muscle |
| γ | Brain, spinal cord |
| Novel PKCs (nPKC) | |
| δ | Brain, myeloid cells |
| ε | Brain |
| η | Skin, lung, skeletal muscle, ovary, testis |
| θ | Skin, skeletal muscle |
| Atypical PKCs (aPKC) | |
| ζ | Brain |
| λ/ι | Skin, skeletal muscle |

PKC isozymes have been shown to translocate to the nucleus upon activation. Phorbol esters translocate PKCα to 3T3 fibroblast nuclei while PKCβ in HL60 cells is translocated to the nuclei by phorbol ester activation. PKCβ has also been found in liver nuclei. The presence of PKC isozymes in the nucleus suggests that activation of PKC in the nucleus may be important for regulation of gene expression.

The PKC13 Gene

The molecular cloning and biochemical experiments on the genomic structure of the PKC isozymes reveals that they are encoded on distinct chromosomes except PKCβI and -βII which are alternatively spliced products derived from a single PKCβ gene. The variable V5 domain of the PKCβ gene is alternatively spliced to generate PKCβI or PKCβII mRNAs. The βI and βII cDNAs, from rat or rabbit brains, encode 671 and 673 amino acid sequences respectively. The resulting proteins differ in their carboxyl terminal regions by 50–52 amino acid residues.

Alternative splicing of the PKCβ pre-mRNA, shown in FIGS. 3A and 3B, generates the mature PKCβI nRNA and the exon-included PKCβII cRNA that shares a common 3' untranslated region and poly (A) tail with PKCβI mRNA. This insertion in to the coding region introduces a termination codon near the splice site such that the PKCβII sequence is only two amino acids longer than PKCβI polypeptide. As shown in FIG. 4, the PKCβII cDNA is longer than the PKCβI cDNA by means of insertion of a 216 bp independent exon.

The expression of the PKCβ gene is developmentally regulated and shows cell type specificity (Niino, S. et al, 1992, pp.6158–6163). To determine the mechanism for the cell type specificity of transcription of PKCβ gene, Niino et al (Niino, Y., S., S. Ohno, and K. Suzuki. 1992. Positive and negative regulation of the transcription of the human protein kinase C βgene. J. Biol. Chem. 267:6158–6163.) demonstrated the presence of multiple trans-acting factors that act on positive and negative cis-acting elements and regulate transcription of the human PKCβgene, hence providing an explanation for regulation of its cell-type specific expression. Obeid et al (Obeid, L. M., G. C. Blobe, L. A. Karolak, and Y. A. Hannun. 1992. Cloning and characterization of the major promoter of the human protein kinase C β gene. Regulation by phorbol esters. J. Biol. Chem. 267:20804–20810) have cloned the 5' region of the gene for PKCβ and identified its promoter. Although the mRNAs for PKCβI and PKCβII are distinct, the transcription of both the mRNAs is under the regulation of the common PKCβ promoter. The transcriptional initiation site is 197 bp upstream of the translational initiation site. The promoter region for PKC, is GC-rich (>80%) and the TATA and CAAT elements are found upstream of the transcription start site in the reverse order. Other regulatory cis-acting elements are shown in Table 3.

TABLE 3

Potential trans-acting factors regulating cis-acting elements in the promoter region of the PKCβ gene.

| TRANS-ACTING FACTOR | CIS-ACTING ELEMENT | POSITION IN PKCβ GENE |
|---|---|---|
| Oct BP | ATGCAAAT | −76 |
| Sp1 | GGGCGG | −94, −63 |
| E$_{12/47}$ | GCAGGTGG | −110, −26, +18 |
| ChoRE | CACGTG | −318 (CACCCG), −226 (CTCCTG) |
| AP$_2$ | CCCCACCCC | −330 |
| CTF/NF-1 | GCCAAT | −395 |
| AP$_1$ | TGAGTCA | 442 |
| TFIID | TATAAA | −530 |

To study the promoter elements, Obeid, et al (Obeid, L. M., G. C. Blobe, L. A. Karolak, and Y. A. Hannun. 1992. Cloning and characterization of the major promoter of the human protein kinase C 0 gene. Regulation by phorbol esters. J. Biol. Chem. 267:20804–20810) used deletion constructs of PKCβ gene. A 154-bp construct (−111 to +43) that contained an octamer motif, two Sp1 sites and one E box could confer promoter activity. This indicated that the TATA or CAAT motifs were not required for basal promoter activity. They further demonstrated that the phorbol esters transcriptionally up-regulated PKCβ in K562 erythroleukemia cells. A feedback loop exists which acts to induce de novo transcription of PKCβ when phorbol esters activate PKCβ and cause its down-regulation.

Activation of Protein Kinase C
Signaling Pathways that Generate PKC Activators

Stimulation of cell surface receptors activates phospholipase C which hydrolyses phosphatidylinositol 4,5-bisphosphate (PIP$_2$) resulting in the production of diacylglycerol (DAG) and inositol 1,4,5-trisphosphate (IP3). Inositol 1,4,5-trisphosphate stimulates the release of $Ca^{2+}$ from intracellular storage (see FIG. 5). Furthermore, DAG is also produced from phosphocholine and results in a sustained elevation of DAG in response to various signals like phorbol esters, growth factors and cytokines. Both DAG and $Ca^{2+}$ mediate the activation of PKC isozymes as shown in FIG. 6. $Ca^{2+}$ binds to C2 domain of cPKC isozymes. Translocation of the enzyme to the membrane enables its activation by DAG and phosphatidylserine, which is a membrane acidic lipid, through binding at its C1 domain.

Model for Regulation and Activation of Protein Kinase C

For protein kinase C to be functionally active, the newly synthesized enzyme is first localized on the cytoskeleton ad rendered catalytically competent by phosphorylations. Mass spectroscopy has revealed that PKC is phosphorylated at three positions in vivo. The residues corresponding to these phosphorylations in PKCβII include Thr500 in the activation loop, Thr641 and Ser660 at the carboxyl terminus. This triple phosphorylated mature form is inactive because the pseudosubstrate occupies the substrate-binding site. As diagrammed in the FIG. 7, the next step requires the removal of the autoinhibitory pseudosubstrate domain from the kinase core. Activation of protein kinase C by diacylglycerol, $Ca^{2+}$ or phosphatidylserine, and subsequent translocation to the membrane, renders the pseudosubstrate sensitive to proteolysis by trypsin or endoproteinase Arg-C. Maximum binding affinity of PKC to the membrane, mediated by domains C1 and C2, releases the psudosubstrate inhibition. The exposed V3 domain hinge also, becomes proteolytically labile on membrane binding (independent of pseudosubstrate release).

Localization of PKC Isozymes by Anchoring Proteins

Both active and inactive PKC isozymes are localized to specific intracellular sites due to their binding to specific anchoring molecules. The anchoring proteins for activated PKC isozymes are termed receptors for activated C-kinase (RACKs) while proteins that anchor inactive PKC isozymes are termed receptors for inactive PKC isozymes in a selective and saturable manner. For example, RACK1—a PKCβII-specific RACK, co-localizes with activated PKCβII to the perinucleus in cardiac myocytes (Ron et al., 1994, pp.839–843) and enhances its activity. PKCε binds to F-actin in vitro and in synaptosomes through εRACK and thus F-actin may show characteristics of εRACK (Prekeris et al., 1996, pp.77–90). Blobe et al (Blobe et al., 1996, pp.15823–15830) have shown that PKCβII, and not PKCβI, binds to F-actin and stimulates PKCβII activity. These observations may suggest that F-actin may have the characteristics of both εRACK (Prekeris et al., 1996, pp.77–90) and βIIRACK (Ron et al., 1994, pp.839–843).

In inactive PKC, a binding site for RICK is exposed. On activation, PKC isozymes bind to RACKs, altering its conformation and exposing the substrate-binding site. As depicted in FIG. 8, RICK binding site is eliminated. Binding of anchoring proteins to PKC isozymes is mediated through phosphatidylserine (PS) or lipid bridges and through direct protein—protein interactions. These anchoring proteins could contribute to another level of regulation of PKC signaling and provide a platform for cross-talk between PKC isozymes.

Carbohydrate Response Element (ChORE)

Glucose, the preferred energy source for most eukaryotic cells, alters gene expression in diverse cell types. Glucose stimulates insulin gene expression in pancreatic β-cells, IGF-1 expression in glioma cells, liver-type pyruvate kinase (L-PK) and $S_{14}$ gene expression in hepatocytes and alters epidermal growth factor signaling in rat fibroblasts. Towle et al first described the carbohydrate response element (ChORE) in the $S_{14}$ gene that is regulated by glucose (Sayeski, P. P. and J. E. Kudlow. 1996. Glucose metabolism to glucosamine is necessary for glucose stimulation of transforming growth factor-alpha gene expression. J. Biol. Chem. 271:15237–15243) in hepatocytes. A consensus motif comprising of 5'CACGTG 3' is central for the glucose response in both the L-PK and $S_{14}$ genes. CACGTG motif is also the core-binding site for the c-Myc family of transcription factors. Two copies of CACGTG motif (with a 4 bp out 6 bp match) separated by a 5 bp spacer is critical for glucose control of gene expression. The requirement for two CACGTG motifs suggests that two identical or closely related factors may bind to provide the carbohydrate response noted for transcription of the L-PK and $S_{14}$ genes.

Although a carbohydrate response factor has not yet been described, we could speculate the made of action of such a factor. Glucose or its metabolite could serve as a direct activator by binding to the ChoRE. An example is the peroxisome proliferating-activated receptor (PPAR), a member of the thyroid/retinoic acid nuclear receptor family. PPAR activates genes involved in fatty acid oxidation by binding directly to DNA response elements of these genes (Nakshatri et al., 1998, pp.2491–2499). Alternatively, a covalent modification such as phosphorylation/dephosphorylation, in response to carbohydrate metabolism might modify the carbohydrate response factor.

The Pathogenesis of Atherosclerosis

Vascular smooth muscle cell proliferation is a principal contributor to the development of atherosclerosis and hypertension—the two major forms of vascular disease. Atherosclerosis is the predominant factor in the advent of heart attack, stroke and gangrene of the extremities. It is responsible for approximately 50% of all mortality in the USA, Europe and Japan. Blood vessels begin as endothelial channels and develop into adult arteries by differentiation of smooth muscle cells.

Replication of smooth muscle cells occurs as the initial event in the formation of atherosclerotic lesions, preceding lipid accumulation or endothelial injury. Smooth muscle cells may be stimulated to proliferate and develop atherosclerotic plaques within the intimal thickenings (Orekhov et al., 1984, pp.17–24; Santen et al., 1972, pp.833–843). Plaques consist of focal proliferation of smooth muscle cells and accumulation of foam cells and extracellular lipid within the thickenings (Schwartz et al., 1986, pp.427–444). In the early stages of the atherosclerotic process, smooth muscle cells migrate from the media to the intima of the arterial wall. Here, the smooth muscle cells proliferate and deposit extracellular matrix components forming a lesion.

The advanced lesions of atherosclerosis become a disease when in excess and can occlude the artery. The endothelium and smooth muscle cell walls respond to various forms of injury or trauma with excessive inflammation and proliferation. The major hypothesis explaining smooth muscle cell replication and proliferation in the blood vessel is the "response to injury" hypothesis present by Ross in 1986 (Ross, R. 1986. The pathogenesis of atherosclerosis—an update. New England Journal of Medicine 314:488–500). Ross proposed that smooth muscle cells in the wall normally exist in a quiescent state. The principal source of connective tissue in the arterial wall is the smooth muscle cell. Smooth muscle cells show two different phenotypes, synthetic or contractile, based on the presence and distribution of myosin filaments and secretory protein apparatus, endoplasmic reticulum and Golgi. As diagrammed in FIG. 9, the primary role of the smooth muscle cell in the synthetic phenotype is proliferation whereas in the contractile phenotype, it contracts in response to external stimuli.

Injury to the endothelium can be caused by exposure to agents like oxidized LDL, toxins, and viruses or may result from mechanical stress. In response to the injury, the endothelium releases potent growth-regulatory molecules that stimulate smooth muscle cell movement and proliferation into the arterial wall. Growth factors, cytokines, lipids and molecules like nitric oxide induce cell recruitment and migration, cell proliferation and control lipid and protein synthesis in the process of atherogenesis.

As the process continues, monocytes become macrophages on reaching the arterial surface, and accumulate lipid. It then proceeds to become foam cells and together with accompanying lymphocytes become the fatty streak predominantly at branch points of the artery. Continued cell influx and proliferation of the smooth muscle cells lead to advanced lesions and ultimately to the fibrous plaque. FIG. 10 shows a representation of the Ross model. Likewise, there is a shift from the contractile to the synthetic phenotype. Progression of atherosclerotic lesions is accelerated by increased smooth muscle cell proliferation.

Diabetes Mellitus

The prevalence of atherosclerotic vascular disease among diabetic patients occurs more frequently as compared to normal subjects. Diabetes mellitus is one of the major causes of mortality and disability in all ages. Diabetes mellitus is an endocrine disorder caused by relative or total deficiency of insulin action. Hyperglycemia, abnormally high blood glucose level, is the diagnostic hallmark of diabetes. Insulin-dependent or type I diabetes has early onset and is caused by the destruction of pancreatic β cells such that insulin is no longer produced. Non-insulin dependent or type II diabetes occurs in middle to older aged individuals. Patients have reduced basal or glucose-induced insulin release or show insulin resistance. In either case, insufficient insulin action leads to overproduction and underutilization of glucose. The flux of glucose and its metabolites has diverse effects on many cellular processes. Various complications arise with hyperglycemia involving the cardiovascular tissue, peripheral nerves, retina, glomeruli and cells involved in wound healing. Excess glucose can alter signal transduction pathways via activation of diacylglycerol and protein kinase C isozymes.

TABLE 4

Diabetes Mellitus

| | CAUSE | ONSET |
|---|---|---|
| Type I | Destruction of pancreatic β cells | Early |
| Type II | Insulin resistance | Late |

Hyperglycemia and PKC Signal Transduction Pathway

Hyperglycemia is responsible for increasing the risk of developing vascular complications by stimulating abnormal proliferation of vascular smooth muscle cells (VSMC). VSMC exhibit increases in proliferation in response to elevated glucose. Protein kinase C has been implicated as a mediator of diabetes-induced vascular proliferation. Hyperglycemia-induced increases in diacylglycerol (DAG) in tissues like aorta and heart and retina from diabetic rats leads to a sustained elevation of PKC. Multiple cellular and functional abnormalities in the diabetic vascular tissues have been attributed to the activation of DAG-PKC pathway. These include angiogenesis, cardiomyopathy, increased contractility in macrovessels, increased vascular permeability and neovascularization and other diabetic and neurological complications.

Glucose is incorporated into the glycerol backbone of DAG as shown by studies using labeled [$^{14}$C]- or [$^3$H]-glucose in aortic smooth muscle cells and aortic endothelial cells. The de novo synthesis pathway of DAG involves the metabolism of glycolytic intermediates. The fatty acids predominantly incorporated into DAG are palmitate and oleic acid along with glycerol-3-phosphate. The elevation of DAG in the vasculature induced by hyperglycemia or diabetes is maintained chronically. Thus, diabetic hyperglycemia leads to increased activation of PKC. Although, the PKC isozymes and 4 are predominantly detected by immunoblotting studies of vascular cells associated with the DAG-PKC pathway, PKCβII levels are preferentially elevated as a result of increased DAG levels in the aorta and heart of diabetic rats. In prior investigations, experiments were carried out using in vivo diabetic rat models subjected to chronic glucose exposure for 2 to 4 months, see for example, Shiba et al (Shiba, T., W. Heath, R. Sportsman, and G. L. King. 1990. Characterization of the activation of protein kinase C isozymes in the retina of diabetic rats. Diabetes 39(Supplement 1):31A). PKC activity was examined in non-synchronized VSMC cultured under chronic high glucose conditions for 5 to 10 days. The increase in PKC activation was measured as increased translocation of the cytosolic PKC to the membrane.

Acute hyperglycemic conditions are prevalent even in controlled diabetic patients. It was established that hyperglycemia is linked to PKCβ expression in vascular smooth muscle cells but the molecular mechanism was not elucidated. Studies of acute glucose exposure (from 0 to 24 ours) on PKCβ gene expression in VSMC was not carried out. Further, the potential level(s) at which glucose could exert its effect on PKCβ isozymes gene expression had yet to be determined. In order to extend our knowledge towards the immediate effects of hyperglycemia on vascular cell proliferation and function via the PKC pathway, a mechanistic study was undertaken.

Signal Transduction

In order to coordinate growth, differentiation and response to the environment, cells of multi-cellular organisms have an intricate signaling network comprising of soluble signal molecules or direct contacts. Generally, a signaling molecule interacts with a cell surface receptor and initiates a cascade through the cytoplasm leading to the nucleus where the specific genes are regulated. Cell surface receptors such as receptor tyrosine kinase (RTK) or transforming growth factor-β receptors autophosphorylate and phosphorylate the cytoplasmic protein in response to binding of an external ligand. A complex series of intracellular responses results in diverse cellular responses as proliferation, differentiation, cell motility, production of extracellular matrix and transcription of specific genes.

Cytoplasmic signal transduction components include Ras, MAP kinase, PKC and other signaling pathways (FIG. 11). Ras is a small membrane-bound guanine nucleotide-binding protein that acts as a molecular switch linking receptor tyrosine kinase activation to downstream signaling events. Ras cycles between an active GTP-bound form and an inactive GDP-bound form. The activity of Ras is regulated by Sos, a guanidine nucleotide exchange factor (GNEF). The carboxyl-terminal of Sos contains proline-rich motifs that mediate the interaction of Sos with Grb2, an adaptor molecule comprising of a SH2 domain flanked by two SH3 domains. Following receptor tyrosine kinase activation and autophosphorylation, Sos-Grb2 translocates to the plasma membrane and the vicinity of Ras, thereby activating Ras. The downstream effector of RasGTP is Raf, a serine/threonine kinase that links Ras to the MAP kinase pathway.

Mitogen-activated protein kinase (MAPK) or extracellular signal-regulated kinase (ERK) is a serine/threonine kinase that phosphorylates microtubule-associated protein (MAP). MAPK is phosphorylated in response to a variety of mitogens including nerve growth factor (NGF), insulin, insulin-like growth factor II, and phorbol esters. MAP kinase kinase (Mek) activates MAP kinase by phosphorylating both tyrosine and threonine residues. Raf forms a stable complex with Mek and phosphorylates Mek on serine residues in vitro. Ribosomal S6 kinase (Rsk) is a component of the eukaryotic 40S ribosomal subunit that is phosphorylated on multiple serine residues in response to mitogen stimulation. Purified MAP kinase from insulin-stimulated cells could activate Rsk and comprise a step in the kinase pathway to transduce mitogenic signals to the nucleus. Thus the MAP kinase pathway (FIG. 11), consisting of Ras, Raf, Mek, MAPK and Rsk spans from the plasma membrane to the nucleus and serves to transduce mitogenic signals downstream from the membrane receptor tyrosine kinases. Several components of this pathway such as Ras and Raf are oncogenic in their constitutively active form. MAP kinases can translocate to the nucleus upon mitogenic stimulation and regulate growth-specific gene expression. Transcriptional factors c-Myc and C/EBPβ can be phosphorylated by MAP kinases in vitro and hence a spectrum of genes can be regulated by the MAP kinase pathway.

Nuclear responses to external signals can be achieved via the transcription factors or by nuclear receptors such as steroid receptors. In response to cytokines such as interferon α/β, the Jak/STAT pathway is activated to regulate the transcription of genes. The initial step is ligand-dependent dimerization of the receptors that brings the Janus kinases (Jaks) into close proximity. Jaks are constitutively associated with the receptor chain and are tyrosine phosphorylated upon receptor aggregation. The activation of Jak correlates with the tyrosine phosphorylation of the receptor components that recruit the signal transducers and activators of transcription (STATs) through their SH2 domains which, in turn, are phosphorylated at their carboxy-terminal tyrosine residue. Homo- or heterodimers of the STATs translocate to the nucleus where they interact with the promoter elements or combine with DNA binding motifs.

Phosphoinositide-3-kinase (PI3-kinase) is implicated as a mediator of biological responses such as DNA synthesis, glucose transport, cytoskeletal rearrangements, cell survival, oocyte maturation and receptor internalization. PI3-kinase phosphorylates the inositol ring of phophotidylinositol (PtdIns) to generate phophotidylinositol-3-phosphate, PtdIns(3)P and further phophotidylinositol-3,4-bisphosphate, PtdIns(3,4)$P_2$ and phophotidylinositol-3,4,5-trisphosphate, Ptd(3,4,5)$P_3$. Further, phophotidylinositol-3,4-bisphosphate is a substrate for phospholipase C which generates the second messengers Ptd(3,4,5)$P_3$ and diacylglycerol.

PI3-kinase consists of two subunits, p85α and p110α. The catalytic activity resides in the 110 kDa subunit while the 85 kDa subunit performs a regulatory role. As diagrammed in FIG. 12, PI3-kinase is activated by several molecules that include cytoplasmic Src-family kinases, receptors with intrinsic tyrosine kinase activity, focal adhesion kinase (FAK), Ras-GTP, Rho and others. The downstream targets of PI3-kinase include the protein kinase C family, p70-S6 kinase, glucose transporter GLUT4 (Hara et al., 1994, pp.7415–7419), serine/threonine kinase Akt/Rac.

Protein Phosphatases

Reversible protein phosphorylation is a critical component of the signal transduction mechanisms in eukaryotes. It is the basis for the control of many biological events triggered by extracellular effectors like hormones, mitogens, oncogenes, cytokines and neurotransmitters. Reversible protein phosphorylation catalyzed by the opposing and dynamic action of protein kinases and phosphatases, is a ubiquitous element of intracellular signal transduction pathways that regulate metabolism, gene expression, cell division, differentiation, development, contraction, transport, cell locomotion, and learning and memory. Abnormal changes in the activities of the protein kinases and phosphatases can lead to severe consequences including immunological defects and cancer.

Protein phosphatases can be classified into three groups according to their substrate specificity.

1. Serine/threonine phosphatases dephosphorylate serine (Ser) and threonine (Thr) residues in proteins and usually require a divalent metal ion to function. They are further divided into two classes: type-1 phosphatase (PP 1) preferentially dephosphorylates the β-subunit of phosphorylase kinase whereas the type-2 phophatases (PP2) preferentially dephosphorylate the α-subunit of phosphorylase kinase. PP2 can be further subdivided into spontaneously active (PP2A), $Ca^{+2}$- and calmodulin-dependent (PP2B) and $Mg^{+2}$-dependent (PP2C) classes. Okadaic acid, polyether fatty acid and a potent inhibitor of protein phosphatases is cell permeable and serves as a valuable tool to study the functions of protein phosphatases. It is a potent inhibitor of PP2A ($K_i$=0.2 nM) and PP1 ($K_i$=20 nM) and a less potent inhibitor of PP2B ($K_i$=μM).

2. Tyrosine phosphatases dephosphorylate tyrosine (Tyr) residues in proteins and share a conserved active-site sequence motif Cys-X5-Arg (X=any amino acid residue) [SEQ ID NO:1] and a Asp located in a surface loop. Protein tyrosine phosphatases (PTPs) are characterized by a signature sequence motif of 11 amino acid residues, (Ile/Val)-His-Cys-X-Ala-Gly-X-Gly-Arg-(Ser/Thr)-Gly [SEQ ID NO:2] that is found in most PTPs. The diversity within the PTPs arises from the variable N- or C-terminal sequences attached to the core catalytic domain.

3. Dual-specificity phosphatases dephosphorylate Ser/Thr residues in addition to Tyr residues in proteins. Their signature motif, His-Cys-X-X-Gly-X-X-Arg-(Ser/Thr) [SEQ ID NO:3] is analogous to PTPs but these phophatases display a restricted substrate specificity.

Cell Cycle and Role of PKCβ Isozymes in the A10 Vascular Smooth Muscle Cells.

The process of cellular proliferation in eukaryotes includes the division of a cell into two daughter cells. Cell division involves mitosis in which the nuclear membrane dissolves, the chromosomes condense and separate into two groups, and two nuclear membranes reassemble around the chromosomes. Finally, in the process of cytokinesis, the cell membrane contracts in the middle and two halves separate to form individual cells.

The phases of the cell cycle that occur prior to cell division start with the G1 phase. The S phase follows in which the chromosomes are replicated and the cell then enters the G2 phase where the preparation for mitosis (M phase) occurs. Cell cycle regulation predominantly occurs during the G1/S transition and the G2/M transition.

Vascular smooth muscle cells (VSMC) cultured in plasma-derived medium are unable to proliferate and are arrested in the G0 phase. These quiescent cells progress into the S phase upon addition of growth factors and begin DNA synthesis (Ross et al., 1978, pp.497–508). It has been demonstrated that PKCβI stimulated while PKCβII inhibited the G1/S transition. VSMC proliferation is accelerated when the inhibitory role of PKCβII on proliferation is disrupted. Further, the overexpression of PKCβI shortened the S phase while the overexpression of PKCβII prolonged the S phase suggesting a role for PKC βI and -βII in the entry of G2/M phase. The requirement for PKCβII for the G2/M phase transition of cell cycle has also been shown in HL60 cells.

Levels of Gene Regulation

All cells regulate gene expression in response to changes in the external environment. Nutritional and metabolic signals play an important role in controlling gene expression.

Levels of regulation in eukaryotes is shown in FIG. 13. The central dogma of biochemistry states that the genes are aligned on the chromosomes and are made of DNA which is transcribed into RNA, followed by translation into proteins. RNA also undergoes maturation by post-transcriptional modifications like the 5' methylation and capping, 3' polyadenylation, alternative or differential splicing according to tissue specificity and editing. The processing in eukaryotic mRNA occurs in both the nucleus and cytosol and involves a fine balance between transcriptional and posttranscription levels. The protein undergoes post-translational modification such as glycosylation, farsenylation and addition of signal peptides for maturation.

Post-transcriptional regulation of the mRNA stability establishes the steady state level of the transcript. Although the steady state level of any mRNA depends on both the rate of synthesis and degradation of the mRNA, abundance of many mRNAs is correlated with the longevity of the transcript.

The RNA transcript is initially synthesized as the heterogeneous nuclear RNA by the action of RNA polymerase II on genomic DNA, and is further processed into mature mRNA within the nucleus. It is then translocated into the cytoplasm where its fate is determined. The mature mRNA can undergo localization, degradation or be translated into the protein (see FIG. 14). Messenger RNA degradation in eukaryotic cells is a regulated process that represents a powerful means for controlling gene expression. mRNA decay is not a random process involving degradation by nucleases. Rather, it is a precise process orchestrated by cis elements coordinating the trans-acting factors in controlling gene expression.

The elements involved in the regulation of transcript stability are shown in FIG. 15. mRNAs can contain two or more separated stability determinants, each of which may be involved in a distinct decay pathway or a specific response to a regulatory factor. For instance, multiple elements within the interleukin-2 (IL-2) mRNA modulate its stability in a combinatorial manner. Although the 3'UTR with its AU-rich elements are primarily involved in regulating stability, the 5' UTR and its immediate coding region contain an element that confers c-jun $NH_2$-terminal kinase (JNK)-mediated stabilization.

1. 5' cap: The mRNA cap is important in preventing the degradation of transcripts. mRNAs without caps are fourfold less stable than capped mRNAs as observed in oocytes and cell-free in vitro decay reactions. Decapping could be a rate-limiting step in mammalian mRNA decay. The mRNA cap may be involved in the translational activity of the transcript that could then modulate its rate of degradation.

2. 5' untranslated region (5' UTR): The half-life of mRNAs is affected by its 5' UTR and its influence on translational regulation. The presence of a secondary structure, like a stem-loop, can inhibit translation. The ferritin mRNA contains an iron responsive element (IRE) in its 5' UTR that affects its translation. Ferritin is a major intracellular iron storage protein. Under low iron conditions, an iron responsive protein binds to the IRE and represses translation.

The 5'UTR of the long-lived *Escherichia coli* ompA transcript functions as an mRNA stabilizer that prolongs the cytoplasmic lifetime of mRNAs by hindering distinct mRNA pathways for mRNA degradation. Two domains of the 5'UTR are responsible in this stabilizing effect: the 5'-terminal stem loop and the single stranded RNA segment (ss2) that contains a ribosome binding site.

3. Premature stop codons: Nonsense codons lead to abrupt termination of translation. Another function attributed to some early premature stop codons is to decrease the levels of nuclear-associated transcripts, thereby reducing the steady state levels of mature mRNA available for translocation to the cytoplasm. This is also observed in phytohemaglutinnin mRNA whose stability is decreased by the presence of premature nonsense codons.

4. Coding region sequences: Sequences within the coding region can also play a role in determining the mRNA half-life. Stability determinants have been demonstrated within the coding regions of c-myc mRNA and c-fos is a rapidly inducible gene involved in immediate early response. It contains three stability determinants—one in the 3' UTR and two in the coding region. One of the coding-region determinants encodes the basic and leucine zipper regions and its structure specifies the instability of mRNA irrespective of the protein binding to it. Another example is that of c-myc mRNA coding region that influences the mRNA half-life via a C-terminal determinant containing a part of the helix-loop-helix and the entire leucine zipper motif (Ross, 1995, pp.423–450). The capsid protein L2 of the human papillomavirus (HPV) type 16 contains cis-acting inhibitory sequences in its coding region that act in an orientation dependent manner to reduce cytoplasmic and nuclear mRNA levels. In the case of *Synechococcus sp.* strain PCC 7972, the 5'UTR acts mutually with the coding-region stability determinant to regulate its stability.

Bernstein, P. L., D. J. Herrick, R. D. Prokipcak, and J. Ross. 1992. Control of c-myc mRNA half-life invitro by a protein capable of binding to a coding region stability determinant. Genes Dev. 6:642–654 demonstrated a protein binding within a c-myc coding region that affected its stability. Proteins that bind to mRNA coding region are implicated in determining the decay rate of the mRNA. Proteins binding to c-fos and c-myc coding region stability determinants have been described that influence the mRNA stability. A 70 kDa polysome-associated protein that binds to the c-myc coding region has been identified and purified (see, for example Prokipcak, R. D., D. J. Herrick, and J. Ross. 1994. Purification and properties of a protein that binds to the C-terminal coding region of human c-myc mRNA. J. Biol. Chem. 269:9261–9269) and serves to protect it from endonucleolytic attack. The urokinase-type plasminogen activator receptor (uPAR) mRNA stability is regulated by a 50-kDa protein binding to a 51-nucleotide fragment in the coding region.

In the case of the β-tubulin mRNA, destabilization is initiated by excess tubulin monomers encoded by the coding-region stability determinant. However, at present date, involvement of a protein in this autoregulation has not been demonstrated.

5. 3' untranslated region (3' UTR): The majority of research has focused on the stability determinants that lie in 3' UTR of the mRNAs. The best-characterized stability determinants are in the 3'UTR of the mRNAs for transferring receptor. The transferring receptor imports iron into cells. Post-transcriptional regulation is achieved through a iron responsive element (IRE) which functions by binding an iron regulatory protein (IRP). When intracellular iron concentration is abundant, the IRE-IRP complex does not form and the transferring receptor is unstable. When the concentrations of iron are low, the formation of the IRE-IRP complex stabilizes the transferring receptor. Another example is that of ribonucleotide reductase R2 mRNA which contains a cis-element in the 3' UTR that is regulated by the TGF-β family. Treatment with TGF-$β_1$, TGF-$β_2$, or TGF-$β_3$ stabilizes the ribonucleotide reductase R2 mRNA. The GAP-43 mRNA (GAP-43 is a neuronal protein) in undifferentiated PC12 cells contains pyrimidine-rich sequences in its 3'UTR that bind to two proteins and regulate its stability.

6. Adenosine-uridine (AU) rich sequences: AU-rich elements (AUREs or AREs) are found in the 3' UTR of mRNAs that encode proto-oncogenes, nuclear transcription factors and cytokines and represent the most common RNA destability determinants characterized in mammalian cells. The AUREs generally contain one or more copies of the AUUUA pentanucleotide and a high content of uridylate and sometimes adenylate residues. A nonamer with an AUUUA core, UUAUUUA(U/A)(U/A), is suggested to be a better indicator in predicting the destabilizing function of the AU-rich sequences. AUREs facilitate rapid deadenylation as the first step in mRNA degradation. The destabilizing activity of an AURE can be increased or decreased by interactions in cis with other sequences like a U-rich region or interactions with trans-acting regulatory factors like the AU-binding proteins (AUBPs). The AREs can be distinguished into three classes: Class I AUUUA-containing AREs direct the synchronous shortening of poly A tails to 30 to 60 nucleotides before mRNA decay; Class II AUUUA-containing AREs direct the asynchronous shortening of poly A tails, with intermediate fully deadenylated products; and a novel class of non-AUUUA ARE described in the c-jun proto-oncogene mRNA which are insensitive to blockage of their effects by the addition of transcription inhibitors.

7. 3' terminal stem loop structure: The histone gene transcripts are cell cycle regulated with large number of molecules present during the S phase and a dramatic decline at the end of the S phase. The histone mRNAs are not polyadenylated but the presence of a 3' terminal stem loop structure confers cell cycle regulation of transcript stability. A stem-looping binding protein and histone proteins themselves might be involved in the regulation process.

8. Poly(A) tail: The polyadenylated tail has multiple functions affecting nuclear processing of pre-mRNA, transport to the cytoplasm, translation, and cytoplasmic mRNA stability. The poly(A) tail via binding to the poly(A) binding proteins (PABPs), protects mRNAs from rapid or indiscriminate degradation. Polyadenylation can affect transcript stability in mammalian cells by the poly(A) addition site selection used during processing of hnRNA into mature mRNA as seen in the case of insulin-like growth factor I.

Post-transcriptional regulation of gene expression is a critical step in determination of steady state levels of the mRNA. The stability of mRNA can also be influenced by a variety of exogenous factors such as hormones, ions or nutrients (Ross, 1995, pp.423–450). The processing of mRNA involves cis elements present in the transcript that are recognized by specific RNA-binding proteins and participate in RNA masking, mRNA stabilization, and/or movement of mRNAs among different ribosome populations within the cell.

BRIEF SUMMARY OF THE INVENTION

Complications involved in cardiovascular tissue injury recovery are aggravated with episodes of acute hyperglycemia. Protein kinase C (PKC) has been implicated as a mediator of diabetes-induced vascular proliferation. Diabetic conditions, especially acute hyperglycemia, may provoke the excessive formation of atherosclerotic lesions that may ultimately lead to the formation of the fibrous plaques. This study elucidates molecular events occurring after initiation of the cell cycle in quiescent vascular smooth muscle cells following exposure to acute hyperglycemic conditions.

PKCβII is the predominant isoform detected in quiescent smooth muscle cells although these cells also express PKCα, -βI, -δ and -ε. Our previous studies indicate that PKCβI and PKCβII regulate the vascular smooth muscle cell cycle. In A10 cells (a clonal cell line of VSMC) transfected to overexpress PKCβII, DNA synthesis was attenuated. This suggested that PKCβII might function as a cell cycle mediator during G1/S phase transition in VSMC. It was demonstrated that PKCβII protein expression was decreased and the percentage of A10 cells entering the S phase was increased in VSMC in the presence of acute high extra-cellular glucose concentrations. Northern blot studies indicated that the steady-state levels of PKCβmRNA were decreased by high glucose. Based on these findings, it was hypothesized that the hyperglycemia-induced proliferation of VSMC may be related to the regulation of PKCβ gene expression by glucose.

BRIEF DESCRIPTION OF THE DRAWINGS

In FIG. 3A introns are represented by lines while the boxes represent exons. The approximate sizes of the introns and exons of the 3' end of PKCb gene are indicated. In FIG. 3B, the polyadenylation site contains the hexanucleotide AUUAAA. Splicing of the last common exon C4 to βIV5 exon produces the mature PKCβI mRNA whereas the PKCβII mRNA has the βIIV5 exon included. Both PKCβI mRNA and PKCβII mRNA have a common 3' untranslated region and poly(A) tail.

In FIG. 16A, A10 cells were synchronized by culturing the cells in DMEM containing 0.5% FBS for 48 hours. To re-initiate the cell cycle, A10 cells were incubated in DMEM with 10% FBS containing 5.5 mM glucose (control cells) or 25 mM glucose (hyperglycemic condition) for indicated periods up to 18 hours. Western blot analysis was carried out on cell lysates using anti-PKCβI as primary antibody. Proteins were detected using enhanced chemiluminescence (ECL, AMERSHAM) as described in methods. Densitometric scanning was used to quantify PKCβI bands from the blots. FIG. 16B depicts PKCβI protein levels in the presence of 25 mM glucose plotted as the percent of the total PKCβI levels present in the respective control (5.5 mM glucose) cells. Data are representative of at least 5 separate experiments.

In FIG. 17A, A10 cells were synchronized by culturing the cells in DMEM containing 0.5% FBS for 48 hours. To re-initiate the cell cycle, A10 cells were incubated in DMEM with 10% FBS containing 5.5 mM glucose (control cells) or 25 mM glucose (hyperglycemic condition) for indicated periods up to 18 hours. Western blot analysis was carried out on cell lysates using (a) anti-PKCβI and (b) anti-PKCβII as primary antibodies. Proteins were detected using enhanced chemiluminescence (ECL; AMERSHAM) as described in methods. Densitometric scanning was used to quantify PKCβI and PKCβII bands from the blots. FIG. 17B depicts PKCβI and PKCβII protein levels in the presence of 25 mM glucose plotted as the percent of the total PKCβI and PKCβII levels present in the respective control (5.5 mM glucose) cells. Data are representative of at least 5 separate experiments.

In FIG. 18A, total RNA was extracted from A10 cells that were synchronized in culture with DMEM containing 0.5% FBS for 48 hours, then re-initiated to proliferate with DMEM+10% FBS, and incubated for 15–18 hours in medium (DMEM+10% FBS) containing 5.5 mM glucose (lane 1), mM glucose (lane 2) or 25 mM mannitol (lane 3) as indicated. RNA (10 μg) was fractionated on 1.2% agarose-formaldehyde gel, 28S and 18S rRNA were visualized to ensure equal loads of RNA (lower panel), capillary transferred to Hybond membrane (AMERSHAM) and probed with a $^{32}$P-labeled PKCβ cDNA probe that would detect PKCβ(I+II) mRNA as described in methods. Following exposure to X-ray film, the autoradiogram was analyzed densitometrically. In FIG. 18B, a 6075% decrease in PKCβ(I+II) mRNA (3.5 Kb) was observed under high glucose conditions. Data is representative of an experiment repeated with similar results on at least 4 occasions.

In FIG. 22A, A10 cells were synchronized by maintaining them in DMEM+0.5% FBS for 48 hours, followed by re-initiation of cell proliferation in DMEM+10% FBS. Synchronized A10 cells were pre-treated with actinomycin D (5 μg/ml) for 30 minutes in DMEM+10% FBS. At time zero, glucose was added such that the medium contained 5.5 mM glucose (Con) or 25 mM glucose (Glc). Total RNA was extracted from 0 to 6 hours, and then 10 μg of RNA was fractionated on 1.2% agarose-formaldehyde gels, 28S and 18S rRNA were visualized to ensure equal loads of RNA (lower panel), capillary transferred to Hybond membrane (AMERSHAM), and probed with a $^{32}$P_labeled PKC, cDNA probe that detects PKCβ (I+II) mRNA as described in methods. Images of the 3.5 kb transcript were quantitated using Molecular Dynamics Phosphoimaging system and are representative of three individual experiments. FIG. 22B depicts PKCβ(I+II) mRNA levels, in the presence of 25 mM glucose plotted as the percent of the total PKCβ(I+II) mRNA levels present in the control (5.5 mM glucose) cells. A 60% decrease (* indicates significance at p<0.05) in PKCβ(I+II) mRNA is seen at 6 hours with glucose-treated cells.

FIG. 25. A schematic representation of the PKCβ as deduced from cDNA sequence analysis. The shaded blocks C1–C4 represent the conserved regions while V1–V5 blocks represent the variable regions. The regulatory and the catalytic domains are separated by V3, which serves as a hinge region. PKCβI and -βII, the alternatively spliced products of PKCβ pre-mRNA, diverge in their C-terminal sequence by 50 or 52 amino acids respectively. The enlarged area represents the genomic structure of the alternatively spliced V5 region. Introns are represented by lines and exons are represented by blocks. The arrows indicate the regions that correspond to the sense primer (the last common region (C4) for PKCβI and –βII) and antisense primer (to the βIV5 region) used for amplification of both PKCβI and -βII cDNAs simultaneously.

FIG. 27. PKC βII cDNA (350 bp) sequence [SEQ ID NO:8].

In FIG. 36A, the pβG-PKCβII minigene was stably transfected into A10 cells. 50 g/ml DRB in 95% ethanol was added to the plates and the 0-hour RNA sample was isolated. 25 mM glucose was added to the cells or the cells were maintained in 5.5 mM glucose. RNA samples were isolated at 1 hour, 2 hours, and 6 hours. 10 μg of total RNA was analyzed by Northern blotting. FIG. 36B depicts the mRNA levels remaining at various times after addition of DRB. Blot and graph represents an experiment repeated on 5 different occasions.

BRIEF DESCRIPTION OF THE SEQUENCES

Figure 1:
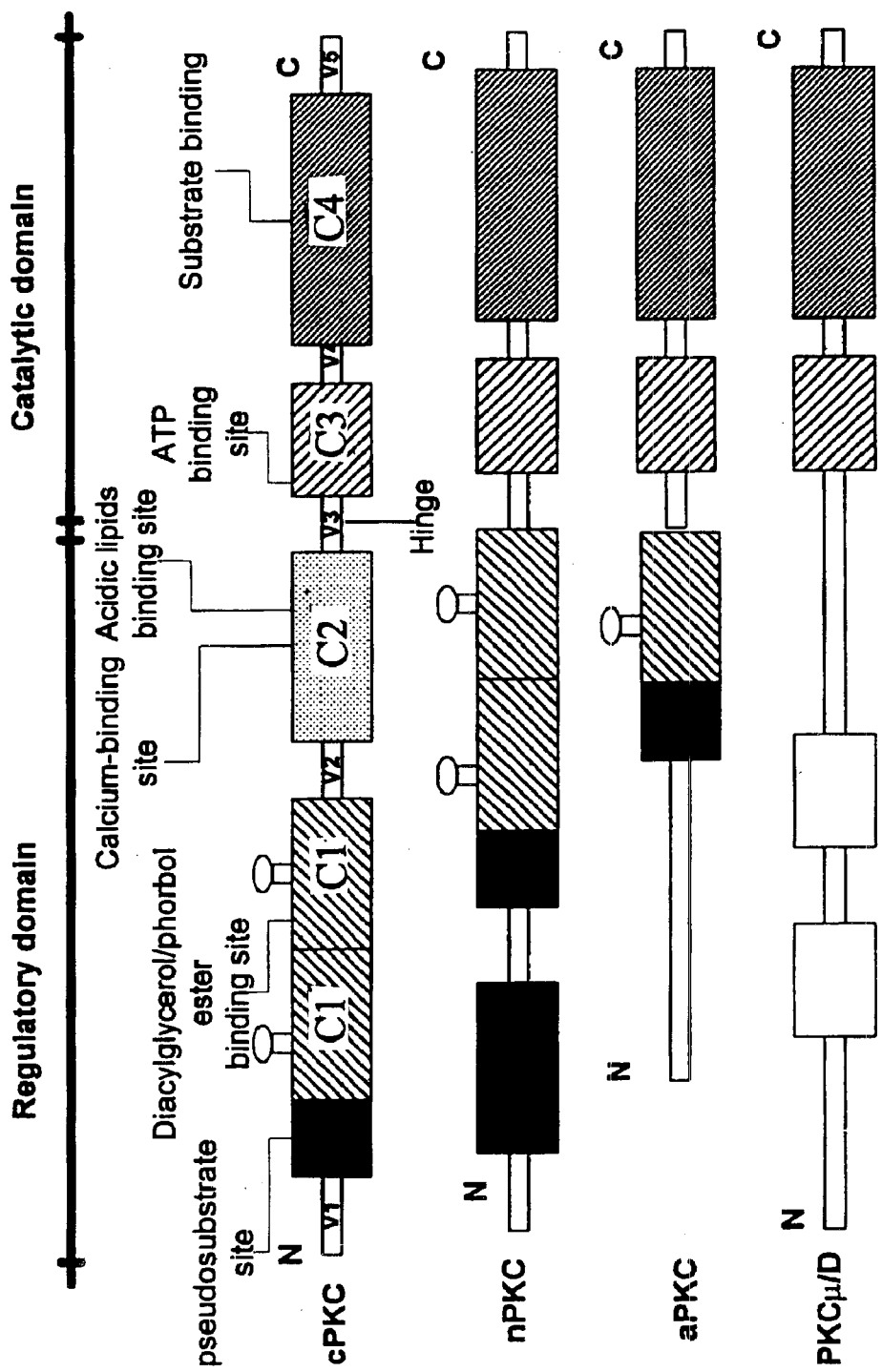
FIG. 1. Schematic representation of the PKC isozymes domain structure. V1 to V5 are the variable regions while C1 to C4 are the common (or conserved) regions. The regulatory domain comprises of the pseudosubstrate site, and one or two of the membrane-targeting motifs, namely C1 present in all PKCs and C2 present in cPKCs and nPKCs. The regulatory domain is separated from the catalytic domain by the hinge (or V3) region. The catalytic domain consists of the ATP-binding and substrate binding sites, the C3 and C4 regions respectively.
Figure 2:
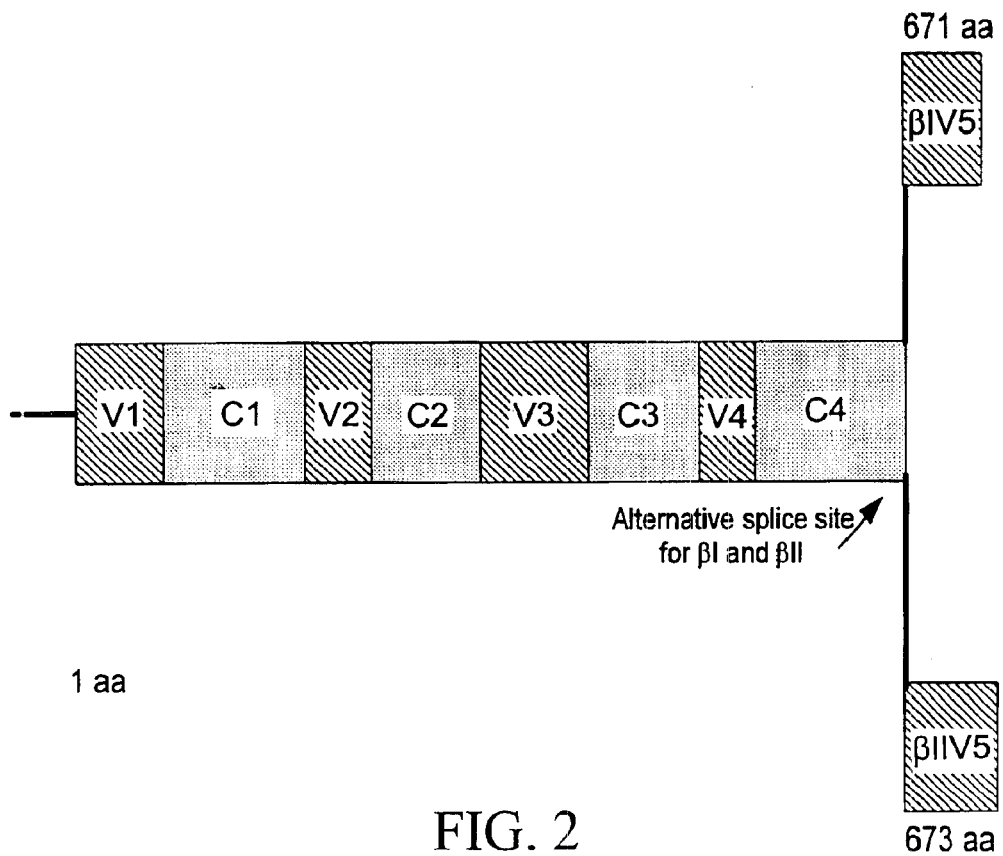
FIG. 2. A schematic representation of PKC, sequence as deduced from the cDNA analysis. The V5 region of alternative splicing for PKCβI and PKCβII is indicated. The resulting amino acids for PKCβI and PKCβII consist of 671 amino acids and 673 amino acids respectively.
Figure 4:
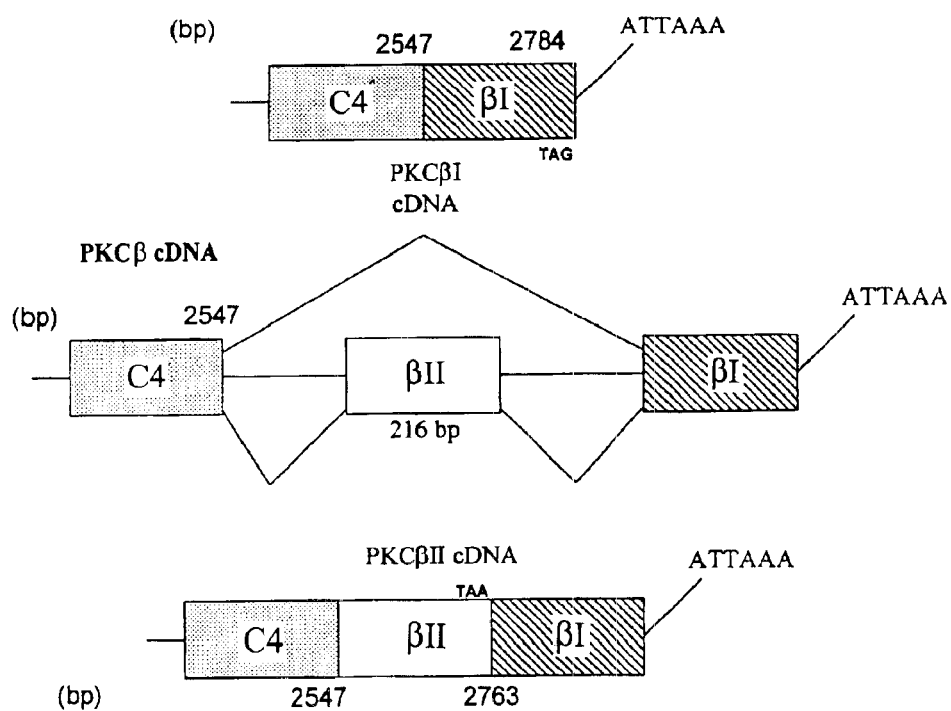
FIG. 4. PKCβII mRNA is generated via exon inclusion in the alternative splicing of PKCβ. The 5' end of PKCβ cDNA contains 684 nucleotides of untranslated sequence followed by ATG (initiation site) at 685 bp position in the C4 region. PKCβI mRNA is generated by splicing of the βI exon at position 2547. The PKCβII mRNA is generated via inclusion of a 216 bp exon at position 2547. This alternative splicing introduces a STOP codon (TAA) at position 2763 in PKCβII mRNA. The coding regions of PKCβI and PKCβII cDNA are followed by 504 nucleotides and 714 nucleotides, respectively in the 3'-untranslated region. The resulting proteins differ in their carboxyl terminal regions by 50–52 amino acid residues (One et al., 1987, pp 1116–1120).
Figure 3A:
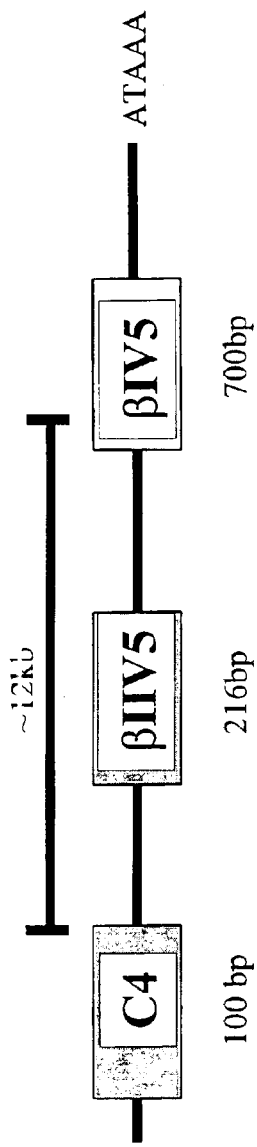
FIGS. 3A and 3B. Alternative splicing of PKCβ pre-mRNA.
Figure 3B:
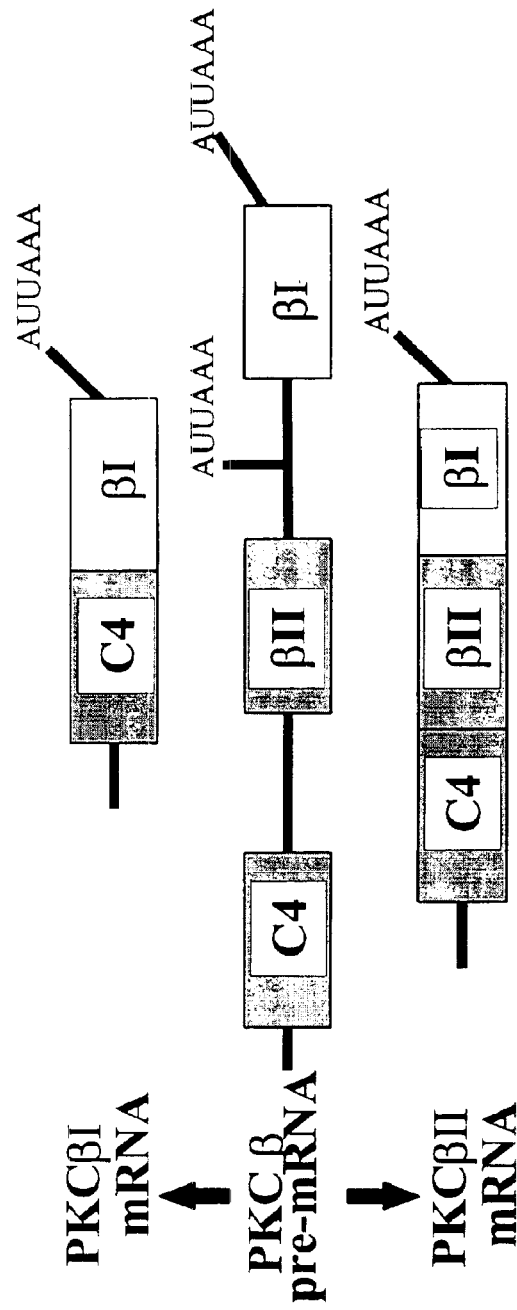

SEQ ID NO: 1 is the amino acid sequence of tyrosine phosphatase conserved active-site motif SEQ ID NO: 2 is the amino acid sequence of tyrosine phosphatase signature sequence motif.

SEQ ID NO: 3 is the amino acid sequence of dual-specificity phosphatase signature sequence motif.

SEQ ID NO: 4 is the nucleotide sequence of PKCβI and PKCβII upstream sense primer.

SEQ ID NO: 5 is the nucleotide sequence of PKCβI downstream anti-sense primer.

SEQ ID NO: 6 is the nucleotide sequence of β-globin sense primer.

SEQ ID NO: 7 is the nucleotide sequence of β-globin anti-sense primer.

SEQ ID NO: 8 is the nucleotide sequence of 350 basepairs of PKCβII cDNA.

SEQ ID NO: 9 is the nucleotide sequence of the metabolite responsive instability element within PKCβII cDNA.

SEQ ID NO: 10 is the nucleotide sequence of PKCβII mRNA.

SEQ ID NO: 11 is the partial nucleotide sequence of PKCβII mRNA.

SEQ ID NO: 12 is the partial nucleotide sequence of PKCβIII mRNA.

SEQ ID NO: 13 is the amino acid sequence of protein kinase ATP-binding motif.

DETAILED DISCLOSURE OF THE INVENTION

Regulatable vectors for gene expression are often not reliable since they can be "leaky". They usually consist of systems where the gene of interest is cloned downstream of a minimal viral promoter fused to copies of the tetracycline operator. The promoters used with these repressor sequences are, however, not totally repressed in many cells. By engineering a construct that is also regulated at the post-transcription level, full repression of such a promoter could be achieved in a wider variety of cells. We propose that by inserting instability sequences down-stream of an inserted cDNA, genes can be further regulated using high extracellular concentrations of glucose or non-metabolized analogues. Both Tet and Retroviral Tet Systems (CLONTECH) show promise for regulating transcription of genes in cells. The ecedysone-inducible expression system derived from *Drosophila* is also commercially available (INVITROGEN) and may have even lower basal activity in mammalian cells. Basal activity of the tetO.HCMC IE promoter is highly variable when tested in several cell lines. Although the promoter was repressed in HeLa and PC12 cells, basal levels were 10–30 fold higher in BHK cells. This high basal activity limits the use of the tetracycline-repressed promoter. If a construct could be engineered that was also regulated at the post-transcriptional level, full repression of such a promoter could be achieved in a wider variety of cells. There are several inducible promoters available; however, no one has developed a system to regulate gene expression at the post-transcriptional level. The post-transcriptional regulation of mRNA destabilization of a gene is another possibility for designing regulatable gene expression constructs. If the cDNA can be destabilized by a non-toxic nutrient or analogue, then expression can be stabilized when the analogue is withdrawn.

Protein kinase C (PKC) has been implicated as a mediator of diabetes-induced vascular proliferation. This study investigated the regulation of PKCβ gene expression following acute glucose exposure in human vascular smooth muscle cells and in A10 cells, a rat aortic smooth muscle cell line. Western blot analysis showed that PKCβII protein levels decreased with high glucose (25 mM) while PKCβI level were unaltered. PKCβ mRNA levels were depleted by 60–75% in hyperglycemic conditions. Quenching of PKCβ promoter activity by glucose suggested involvement of a carbohydrate response element in the 5' promoter region. Simultaneous cell cycle studies indicated an increase in the percentage of cells going into S phase in high glucose implying that quenching of PKCβ transcription may be related to cell cycle progression. It was demonstrated that glucose induced post-transcriptional destabilization of PKCβII message via a nuclease activity present in the cytosol. The specificity of glucose to post-transcriptionally destabilize PKCβII, but not the PKCβI, isoform was confirmed in both A10 cells and primary cultures from human aorta.

To further elucidate the intracellular signaling mechanisms, glucose analogs were used to study the pathways by which glucose acted to destabilize PKCβII mRNA. Glucose-induced destabilization of PKCβII mRNA is independent of the hexosamine or hexokinase pathways. Cycloheximide did not block destabilization of PKCβII mRNA by high glucose indicating that the process is independent of translation. Glucose may act via PKC signaling pathways and may be regulated by serine/threonine phosphorylation/dephosphorylation.

A heterologous chimeric minigene encoding PKCβII cDNA subcloned into the pβG expression vector comprising the coding sequences of β-globin genomic DNA and 3'UTR and polyadenylation site of bovine growth hormone cDNA was constructed. Half-life analysis indicated a rapid glucose-induced destabilization of β-globin mRNA in pβG-PKCβI transfected cells. Mobility shift analysis indicated the presence of a glucose-responsive instability element within the exon included in the mature PKCβII mRNA in VSMC. UV cross-linking analysis showed a small protein (~10–14 kDa) binding near a stem-loop structure within the PKCβII-specific exon. This is a novel finding of a instability element within the PKCβII mRNA coding region that is regulated by glucose in aorta smooth muscle cells.

| ABBREVIATIONS | |
|---|---|
| AoSMC | Aorta smooth muscle cells |
| aPKC | Atypical PKC |
| ARE | Adenosine-uridine rich element |
| $Ca^{+2}$ | Calcium |
| CAT | Chloramphenicol acetyltransferase |
| cDNA | Complementary DNA |
| ChoRE | Carbohydrate Response element |

-continued

| ABBREVIATIONS | |
|---|---|
| cPKC | Conventional PKC |
| CRE | cAMP-responsive element |
| CREB | cAMP-responsive element-binding protein |
| DAG | Diacyl glycerol |
| DMEM | Dulbecco's modified eagle's medium |
| DPBS | Dulbecco's phosphate-buffered saline |
| DRB | 5,6-dicholoro-1-β-D-ribofuranosylbenzimidazole |
| DTT | Dithiothreitol |
| EMSA | Electrophoretic mobility shift assays |
| ERK | Extracellular signal-regulated kinase |
| FBS | Fetal bovine serum |
| FFA | Free fatty acids |
| HEPES | N-2-hydroxyethylpiperazine-N'-2-ethanesulfonic acid |
| HPV | Human papillomavirus |
| IGF | Insulin-like growth factor |
| IL-2 | Interleukin-2 |
| $IP_3$ | Phosphotidylinositol 1,4,5-trisphosphate |
| IRE | Iron responsive element |
| IRP | Iron regulatory protein |
| JAK | Janus kinase |
| JNK | c-jun $NH_2$-terminal kinase |
| L-PK | L-pyruvate kinase |
| Lyso PC | Lysophosphophotidyl choline |
| MAPK | Mitogen-activated protein kinase |
| Mek | MAP kinase kinase |
| MOPS | 3-(N-morpholino)propanesuphonic acid |
| mRNA | Messenger RNA |
| NaCl | Sodium chloride |
| NGF | Nerve growth factor |
| nPKC | Novel PKC |
| oxLDL | Oxidized low density lipoprotein |
| PC | Phosphocholine |
| P13 kinase | Phosphoinositide-3-kinase |
| $PIP_2$ | Phosphotidylinositol 4,5-bisphosphate |
| PKC | Protein kinase C |
| $PLA_2$ | Phospholipase $A_2$ |
| PLC | Phospholipase C |
| PMSF | Phenylmethylsulfonyl fluoride |
| PNE | Post-nuclear extract |
| PP1 | Type-1 phosphatase |
| PP2 | Type-2 phosphatase |
| PPAR | Proliferating-activated receptor |
| PRK | PKC-related kinases |
| PS | Phosphatidyl serine |
| PTP | Protein tyrosine phosphatases |
| RACK | Receptor for activated PKC |
| RICK | Receptor for inactive PKC |
| Rsk | Ribosomal S6 kinase |
| RTK | Receptor tyrosine kinase |
| SmGM | Smooth muscle growth medium |
| STATs | Signal transducers and activators of transcription |
| TF | Transcriptional factors |
| TPA | 12-O-tetradecanoylphorbol-13-acetate |
| UPAR | Urokinase-type plasminogen activator receptor |
| UTR | Untranslated region |
| VSMC | Vascular smooth muscle cells |
| $Zn^{+2}$ | Zinc |

Materials and Methods

Cell Culture

The vascular smooth muscle cell line (A10, ATCC CRL 1476), derived from rat aorta, was grown in Dulbecco's modified Eagle's media (DMEM with 5.5 mM glucose) containing 10% fetal bovine serum (FBS) and 100 units penicillin G and 100 μg streptomycin sulfate/ml at 37C in a humidified 5% $CO_2$, 95% air atmosphere in either 6-well plates (for promoter studies, Western blot analysis, [$^3$H]-thymidine uptake assay) or 100-mm plates (for Northern blot analysis, RNA stability assay). Cells were grown to >90% confluency and media was changed every 4 days. Cell synchronization was achieved by serum deprivation (0.5% FBS) for 48 hours (see, for example, Ross, R., C. Nist, B. Kariya, M. J. Rivest, E. Raines, and J. Callis. 1978. Physiological quiescence in plasma-derived serum: Influence of platelet derived growth factor on cell growth in culture. J. Cell. Physiol. 97:497–508).

Primary cultured human aortic smooth muscle cells (AoSMC) (CLONETICS, San Diego, Calif.) were grown in SmGM (CLONETICS) medium containing 5.5 mM glucose, 5% FBS, 10 ng/ml human recombinant epidermal growth factor (hFGF), 390 ng/ml dexamethasone, 50μg/ml gentamicin, and 50 ng/ml amphotericin-B at 37° C. in a humidified 5% $CO_2$, 95% air atmosphere. Cells were grown to >90% confluency and medium was changed every 5 days.

Materials

The isotopes [α-$^{32}$P]dCTP and [α-$^{32}$P]UTP (specific activity 3000 Ci/mmol) were purchased from ICN Biochemicals. Oligo probe labeling kit (Prime-a-Gene) was purchased from Promega. Riboscribe T7 RNA Probe Synthesis kit and Amplisrcibe T7 Transcription kit were purchased from Epicenter Technologies. RNase A, RNase T1, heparin, RNase inhibitor were purchased from Sigma. All other biochemicals were purchased from the usual vendors as noted. Inhibitors for the signaling pathways were used as described in the results. Cycloheximide (20 mM), PD98059 (20 μM), Okadaic acid (20 nm), AG490 (5 μM), rapamycin (1 mM), herbimycin A (1 μM) and LY 294002 (20 μM) were obtained from Calbiochem. CGP41251 (5 μM) was a gift from Dr. Doriano Fabbro, CIBA-GEIGY (Basel, Switzerland).

Calcium-phosphate Transfections

For promoter studies, A10 cells were grown and synchronized in swell plates. Three hours prior to transfections, fresh medium (DMEM containing 10% fetal bovine serum) was substituted on A10 cells. pβG or pβG-PKCβII expression vectors were transfected with the calcium-phosphate-DNA precipitate. Following overnight incubation, calcium phosphate-DNA precipitate was washed off with 1×Dulbecco's phosphate buffered saline (DPBS) and replaced with fresh medium. For stably-transfected cell selection, 0.7 mg/ml G-418 was added to the media. It was changed every 4 days and 10–14 days later, the colonies were pooled and maintained in DMEM (10% FBS) with 0.2 mg/ml G-418.

mRNA Half-life Determination

A10 cells were pre-treated with actinomycin D (5 μg/μl) for about 30 minutes, followed by the addition of glucose (25 mM) to the glucose-treated plates. RNA samples were isolated from control (5.5 mM glucose) and glucose-treated (25 mM glucose) dishes at 0 h, 2 h, 4 h, or 6 h. Northern blot analysis was then performed on about 10 μg of the total RNA as described below.

In separate experiments, pβG-PKCβII stable transfectants were plated into 100 mm dishes. 5,6-dichloro-1-β-D-ribofuranosylbenzimidazole (DRB) (50 μg/ml) dissolved in 95% ethanol was added to the plates and the 0h RNA sample was isolated. Glucose (25 mM) was added to the glucose-treated plates. RNA samples were isolated from control (5.5 mM glucose) and glucose-treated (25 mM glucose) pβG-PKCβII plates at 2 h, 4 h, and 6 h. In a separate control, an equivalent amount of 95% ethanol was added.

Isolation of RNA and Northern Blot Analysis

Total cellular RNA was isolated from 100-mm plates using Tri-Reagent (Molecular Research Center, Inc.). RNA samples (10 ng) were prepared in formamide, formaldehyde and 1 ×3-(N-morpholino)propanesuphonic acid (MOPS), and fractionated on 1.2% agarose-formaldehyde gels. Ethidium bromide was added in the loading buffer for visualization and quantitation of 18S and 28S RNA. After fractionation, the integrity and loading of RNA was assessed under UV light (23,24). The size-fractionated RNA was then capillary transferred to Hybond membranes (AMERSHAM), and cross-linked to membranes by baking at 80° C. in a vacuum oven for 2 hours. Membranes were hybridized overnight at 42° C. with 2×10$^7$ cpm of the full length PKCβ cDNA probe or β-globin probe (labeled with [$^{32}$P] dCTP by nick translation as described (25)) per ml of hybridization buffer (5×, SSC, 5× Denhardt's solution, 0.5% (w/v) SDS, 50% (v/v) formamide). Membranes were washed with high stringency conditions (1×SSC, 0.1% SDS for 15 minutes at 42° C. followed by 0.11×SSC, 0.1% SDS for 15 minutes at 42° C.), and quantitated using Molecular Dynamics Phosphoimaging System. In experiments, where mentioned, membranes were exposed to X-ray film and the autoradiograms were quantitated densitometrically.

RNA Stability Assay

To prepare post-nuclear extracts (see, for example, Wager, R. E. and R. K. Assoian. 1990. A phorbol ester-regulated ribonuclease system controlling transforming growth factor B1 gene expression in hematopoietic cells. Mol. Cell. Biol. 10:5983–5990), synchronized A10 cells, re-initiated to proliferate with DMEM+10% FBS were treated with either 5.5 mM or 25 mM glucose for 2 h to 24 h, then washed and collected in ice-cold 1×DPBS. The cellular pellet was re-suspended in extract buffer containing 0.01M Tris-HCl, 0.15M NaCl, 0.5% Nonidet P-40, leupeptin (10 μg/ml) and aprotonin (10 μg/ml) incubated on ice for 10 minutes and carefully layered over extract buffer containing 24% sucrose. Samples were centrifuged over a sucrose gradient at 10,000×g for 20 minutes at 4° C. Post-nuclear extract was separated, stored on ice and aliquots taken for protein concentration using Bradford protein assay (see Bradford, M. M. 1976. A rapid and sensitive method for the quantitation of microgram quantites of protein utilizing the principle of protein-dye bindingno title. Anal. Biochem. 72:248–254). Total RNA (10 μg) from A10 cells, was incubated with 2.7% (vol/vol) of the post-nuclear extracts for 30 minutes at 4° C. in 50 μl (final volume) of extract buffer. When specifically noted, 50 mM EDTA was added to the reactions as a control to inhibit nuclease activity. The reactions were terminated by phenol-chloroform extraction, supplemented with 10 μg yeast tRNA as carrier and precipitated with ethanol. RNA was fractionated on 1.2% formaldehyde-agarose gels and Northern blot analysis was carried out with full length PKCβ cDNA probe. The assay and analyses was repeated at least three times with separate post-nuclear extracts to assess and confirm reproducibility.

Reverse Transcriptase-Polymerase Chain Reaction

Total RNA was isolated from control (5.5 mM glucose) or glucose-treated (25 mM glucose) A10 cells and 2 μg was used to synthesize first strand cDNA using on Oligo(dT) primer and Superscript II reverse transcriptase (LIFE TECHNOLOGIES Pre-amplification Kit). The upstream sense primer corresponded to the C4 kinase domain common to both PKCβI and PKCβII (5'CGTATATGCGGCCGCGTTGTGGGCCTGAAGGGG 3') [SEQ ID NO:4] and the downstream antisense primer was specific for PKCβI (5' GCATTCTAGTCGACAA-GAGTTTGTCAGTGGGAG 3') [SEQ ID NO:5] (Chalfant et al., 1995, pp.13326–13332). These primers detect inclusion of the PKCβII exon in the mature mRNA as well as PKCβI mRNA. Sense and antisense primers for β-actin (#5402-3) were obtained from Clonetech. PCR was performed using ampliTaq Gold DNA polymerase from PERKIN ELMER (#N808-0240) on 10% of the reverse transcriptase reaction product. Following 35 cycles of amplification in a BIOMETRA Trioblock thermocycler (PKCβI and -βII: 95° C., 30 sec; 64° C., 2 min for 35 cycles; and for β-actin: 94° C., 1 min; 58° C., 1 min; and 72° C., 3 min for 35 cycles), 25% of the PCR reaction was resolved on a 1.2% agarose gel. Bands were observed under UV light and photographed.

For the stability reporter system, β-globin primers were designed. The sense primer was (5' GCATCTGTCCAGT-GAGGAGAA 3') [SEQ ID NO:6] while the antisense primer for, β-globin was (5' AACCAGCACGTTGCCCAGGAG 3') [SEQ ID NO:7]. PCR was performed using ampliTaq Gold DNA polymerase from PERKIN ELMER (#N808-0240) on 10% of the reverse transcriptase reaction product. Following 25 cycles of amplification in a BIOMETRA Trioblock thermocycler (94° C., 1 min; 58° C., 1 min; and 72° C., 3 min for 25 cycles), 25% of the PCR reaction was resolved on a 1.2% agarose gel. Bands were observed under UV light and photographed. The expected size of the amplified produce was 320 bp.

Synthesis of pCR-blunt-PKCβII

Total RNA was isolated from A10 cells and 10 μg of the RNA was used in the RT-PCR reaction (as described above). The amplified products were separated on 1.2% agarose gel. The PKCβII-specific band of 404 bp was cut from the gel and purified using QIAquick gel extraction kit (Qiagen). The PKCβII cDNA was cloned into the vector pCRblunt (purchased from INVITROGEN, Inc.) and used in the sequencing reaction. By sequence analysis, it was confirmed that the PKCβII mRNA resulted from the inclusion of the 216 bp PKCβII specific exon via alternative splicing of the PKCβ pre-mRNA.

β-globin cDNA Probe Preparation

The pRSV-βG vector (obtained from N. P. Curthoys, Colo. State University) (Hansen et al., 1996, pp. F126–31) was restricted with HindIII and BglII to obtain a 507 bp fragment, which was purified from agarose gel using QIAquick gel extraction kit (Qiagen). 25 ng of the probe was labeled with [α-$^{32}$P]dCTP using Prime-a-Gene (Promega) to a specific activity of $10^9$ d.p.m.

Synthesis of pβG-PKCβII Chimeric Minigene

Figure 34:
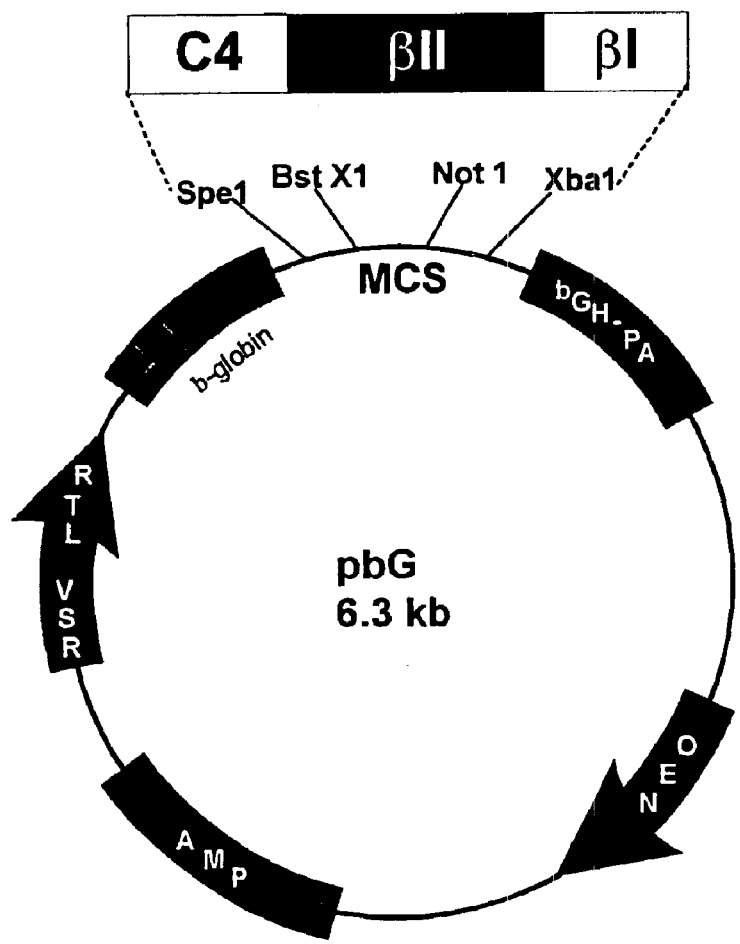
FIG. 34. The pβG-PKCβII chimeric minigene. The parent pβG vector (6.3 kb) contains a chimeric β-globin/growth hormone gene. The promoter derived from the Rous sarcoma virus long terminal repeat (RSV-LTR) is followed by the transcription start site, the coding sequence (open boxes), and two introns (closed boxes) from the rabbit P-globin genomic DNA. The multi-cloning site (MCS) contains four unique restriction sites into which the PKCβII cDNA was subcloned in frame with the β-globin coding region, at the Spe I and Xba I sites. The 3' untranslated region and polyadenylation site of the bovine growth hormone cDNA (bGH-pA) is maintained. It also contains genes that direct eukaryotic cell resistance to neomycin (Neo) and bacterial resistance to ampicillin (AMP).

The parent vector, pβG, was obtained from N. P. Curthoys (see Hansen W. R., Barsic-Tress N., Taylor L., and Curthoys N. P. The 3'-nontranslated region of rat renal glutaminase mRNA contains a pH-responsive stability element. [Journal Article] American Journal of Physiology. 271(1 Pt 2):F126–31, 1996 Jul), Colo. State University. The pβG contains the strong viral promoter derived from the long terminal repeat of the Rous sarcoma virus followed by the transcriptional start site, the 5'-nontranslated region, the entire coding sequence, and two introns from the rabbit cloning gene; a multicloning site containing four unique restriction sites; and the 3'-nontranslated region and polyadenylation site of the bovine growth hormone. PKCβII cDNA was cloned earlier into the pCR-Blunt vector (INVITROGEN) and to expedite the procedure, it was digested with SpeI and XbaI, extracted from the gel (Qiagen's QIAquick gel extraction kit) and purified. The PKCβII cDNA was subcloned in frame with the O-globin reading frame into the SpeI and Xba! sites of the multicloning region of pβG vector (FIG. 34). The 3'-nontranslated region and polyadenylation site of the bovine growth hormone were maintained in the resultant pβG-PKCβII minigene. The construct was verified by restriction mapping and dideoxynucleotide sequencing.

Transcription Vectors

The 404 bp PKCβII product was obtained by PCR amplification using sense primer to the upstream PKC, common C4 domain (5'CGTATATGCGGCCGCGTTGTGGGCCTGAAGGGG 3') [SEQ ID NO:4] and anti-sense primer to βIV5 domain (5' GCATTCTAGTCGACAAGAGTTTGTCAGTGGGAG 3') [SEQ ID NO:5] such that the exon-included PKCβII mRNA was amplified. This PKCβII cDNA piece was cloned into the pCR-Blunt vector (INVITROGEN) such that sense transcripts could be generated from the upstream T7 RNA polymerase promoter. A 410 bp β-globin segment cloned into the pCR-Blunt vector was used as a non-specific competitor probe.

In Vitro Transcription

The RNA probes were generated by consecutive restriction digestion of the pCR-Blunt-PKCβII vector. Probe A was the full length PKCβII insert linearized with BamHI; probe B was PKCβII linearized at 175 bp with BglII within PKCβII exon such that the PKCβI-specific exon was eliminated; probe C was linearized at 137 bp with HpaI which cuts within the PKCβII-specific exon was eliminated; probe D was linearized at 102 bp with SspI which cuts within the PKCβII-specific exon; probe E was linearized at 45 bp with FokI which cuts within the C4 exon. After digestion, the probes were purified and their sizes and linearity were confirmed on agarose gels and further used for in vitro transcription with Ampliscribe kit (Epicenter) for competitor unlabeled probes or with Riboscribe kit (Epicenter) for transcribing labeled RNA probes according to the manufacturer's instructions.

Cytoplasmic Extract (S100) Preparation for RNA Electrophoretic Mobility Shift Assay In brief, A10 cells incubated in 5.5 mM glucose (normal) or 25 mM glucose (high glucose) for 4 h were washed with 1×DPBS, scraped, collected and centrifuged at 3000 rpm for 10 min. The packed ells were re-suspended in hypotonic buffer (10 mM HEPES, pH7.9 at 4° C.; 1.5 mM $MgCl_2$; 10 mM KCl; 0.2 mM PMSF; 0.5 mM DTT; 10 μM leupeptin; 10 μM antipain), allowed to swell for 10 min on ice, and homogenized in a Dounce homogenizer with 60 strokes using a type B pestle. The nuclei was pelleted by centrifuging at 3300×g for 15 min, and the cytoplasmic extract was mixed with 0.11 vol of cytoplasmic buffer (0.3M HEPES, pH7.9 at 4° C.; 1.4M KCl; 0.03M $MgCl_2$). After centrifugation for 1 h in Beckman type 50 rotor at 40,000 rpm, the supernatant was aliquoted, frozen in liquid nitrogen and stored at −80° C. An aliquot was used to determine the protein concentrations using the Bradford method (Bradford, M. M. 1976. A rapid and sensitive method for the quantitation of microgram quantites of protein utilizing the principle of protein-dye bindingno title. Anal. Biochem. 72:248–254) for protein assay.

RNA Electrophoretic Mobility Shift Assay (EMSA)

With modifications to methods described by Brewer, G. and J. Ross. (1989. Regulation of c-myc mRNA stability in vitro by a labile destabilizer with an essential nucleic acid component. Mol Cell Biol 9:1996–2006; Amara, F. M., J. Sun, and J. A. Wright. 1996. Defining a Novel cis-Element in the 3'-Untranslated Region of Mammalian Ribonucleotide Reductase Component R2 mRNA. The Journal of Biological Chemistry 271, No. 33:20126–20131) and Amara, F. M., G. M. Smith, T. I. Kushak, T. L. Takeuchi, and J. A. Wright (1996. A cis-trans interaction at the 3'-untranslated region of ribonucleotide reductase mRNA is regulated by TGF-01, TGF-162 and TGF-β3. Biochemical and Biophysical Research Communications 228 (2): 347–351) cytoplasmic extracts from A10 cells (normal and high glucose) containing 3 μg protein were incubated with 3 μg yeast tRNA, 10 units of RNase inhibitor in a final volume of 10 μl RNA shift buffer (12 mM HEPES, pH7.9, 10 mM KCl, 10% glycerol, 5 mM EDTA, 5 mM DTT, 5 mM MgCl$_2$) for 10 min at room temperature. 100 to 300 fold excess specific cold competitors or 100-fold excess non-specific cold competitor were added to the binding-reactions and incubated for 5 min at room temperature. $^{32}$P labeled RNA probes A, B, C or D (described above) to a specific activity of ~1×10$^6$/μg were added and incubated for 20 min at room temperature. 100 U of RNaseT1 was added and further incubated for 15 min at room temperature, followed by the addition of 5 mg/ml heparin to reduce nonspecific binding, for 10 min on ice. Samples were separated on a 10% polyacrylamide gel in 0.5×TBE buffer. Gels were dried and exposed to Molecular Dynamics Phoshoimaging Screen.

UV Cross-linking of RNA-protein Complexes

RNA-protein binding reactions were carried out as described above for the RNA EMSA. Following heparin addition, the samples were transferred to a 96-well plate, irradiated for 10 min in Stratalinker (Stratagene) on ice. Laemmli's buffer was added to the sample which was then boiled for 5 min and electrophoresed in a 10% SDS-polyacrylamide gel. Gels were dried and exposed to Molecular Dynamics Phoshoimaging Screen.

Results

PKCβII Protein Levels Decreased when A10 Cells were Exposed to 25 mM Glucose

Figure 16A:
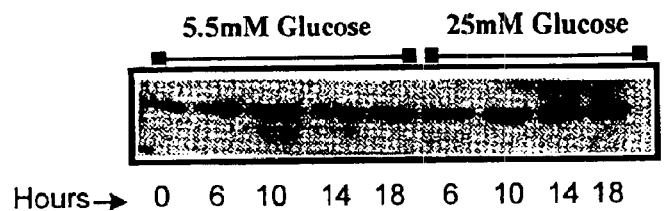
FIGS. 16A and 16B. PKCβI protein levels remain unaltered in the presence of high glucose.
Figure 16B:
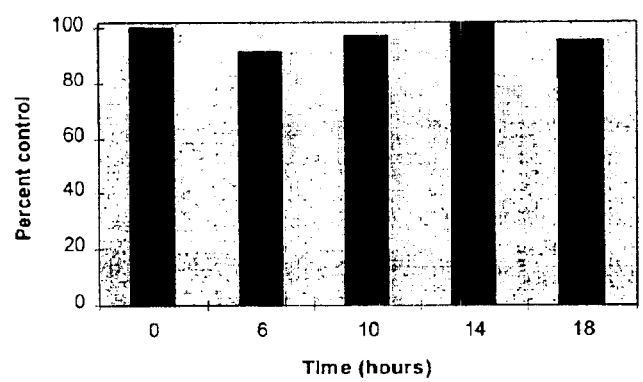
Figure 17A:
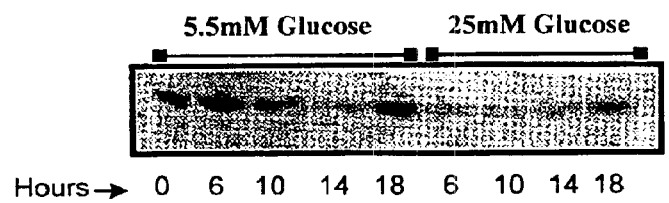
FIGS. 17A and 17B. PKCβII protein levels decreased by 55% in the presence of glucose.
Figure 17B:
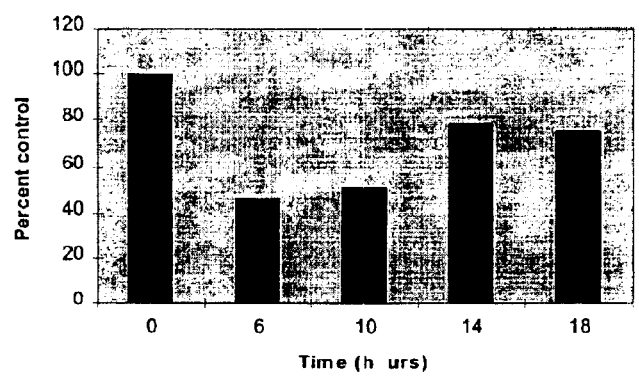

To better understand the biochemical mechanism underlying the acute effects of high glucose exposure on PKCβ expression in aortic vascular smooth muscle cells, protein levels of PKCβI and βII were determined in synchronized A10 cells. Cell growth synchronization was achieved by serum deprivation for 48 hours as described in methods, and following synchronization, medium on A10 cells was replaced with DMEM containing 10% FBS to re-initiate cell proliferation and incubated with high (25 mM) or normal (5.5 mM) glucose. Over a twenty-four hour period, protein was extracted at various time points from cells re-initiated by serum addition to proliferate. It appeared that as cells progressed through the cell cycle, the expression of PKCβII appeared to be cell cycle associated, with highest levels of protein expression observed at 6 and 18 hours and lowest levels occurring at 14 hours. PKCβII protein levels in cells treated with high glucose decreased by 55% within first 6 hours and remained low following 14 hours of continuous high glucose treatment and began to increase at 18 hours (FIGS. 17A and 17B). No significant changes in PKCβI protein levels were detected between high and normal glucose (FIGS. 16A and 16B). To check the specificity of high glucose to down-regulate PKCβII, western blot analysis was repeated using primary antibodies to PKCα and PKCϵ. Again, no significant changes in PKCα or -ϵ protein levels were detected between high and normal glucose treatments (data not shown). Thus, the down-regulation by acute glucose appeared specific for the PKCβII isoform and did not affect the other PKC isozymes.

Hyperglycemic Conditions Markedly Reduce PKCβ(I+II) mRNA in A10 Cells

Figure 18A:
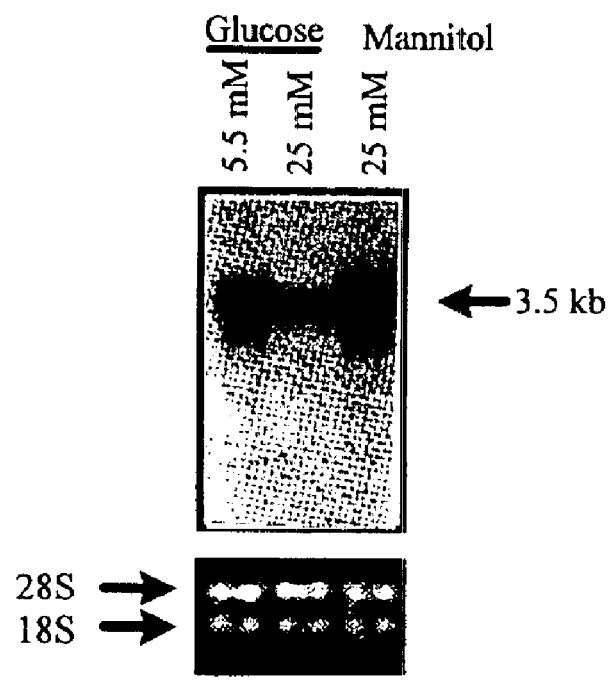
FIGS. 18A and 18B. Down regulation of PKCβ(I+II) mRNA by glucose.
Figure 18B:
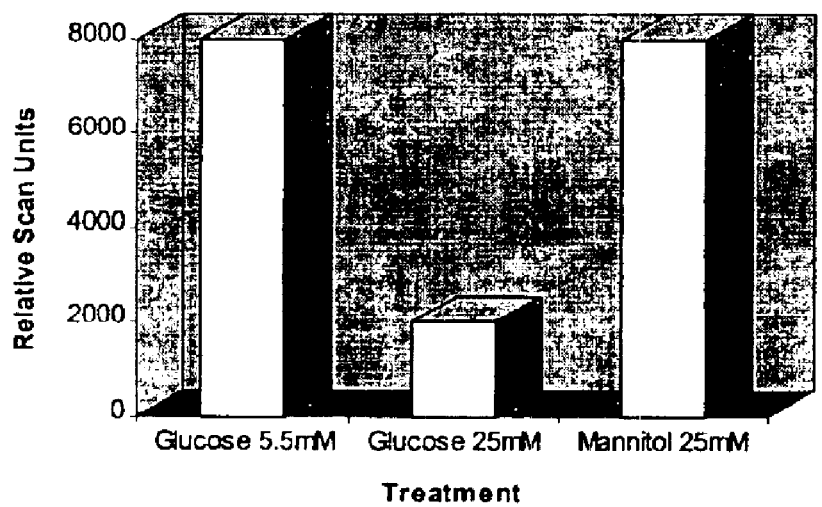

To determine the acute effects of hyperglycemia on PKCβ gene expression, steady state levels of PKCβ mRNA were examined in synchronized A10 cells (by serum deprivation for 48 hours as described in methods) that were re-initiated to proliferate by changing the medium to DMEM containing 10% FBS and incubated for 15–18 hours with either high (25 mM) or normal (5.5 mM) glucose. Cells incubated with 25 mM mannitol were used as osmotic controls. Total RNA was extracted and the mRNA transcript levels were detected using a full length PKCβ cDNA probe which would cross-hybridize with both PKCβI and PKCβII mRNAs. As shown in FIG. 18B, a 60–75% decrease in PKCβ(I+II) mRNA levels were observed in cells treated overnight with high glucose (25 mM). The mRNA levels in the control cells (5.5 mM glucose) and osmotic control cells (mannitol-treated) remained unchanged. This suggested that high glucose down-regulated PKCβ(I+II) gene expression. Since protein analysis following high glucose exposure indicated a decrease only in PKCβII levels, it was assumed that the northern blot analysis reflected a down-regulation of PKCβI mRNA while PKCβI mRNA remained unaltered. Since PKCβII is the product of PKCβ mRNA alternatively splicing, the possibility existed that transcriptional as well as post-transcriptional controls were altered by high glucose.

Glucose Quenches PKCβ Promoter Activity

Figure 19:
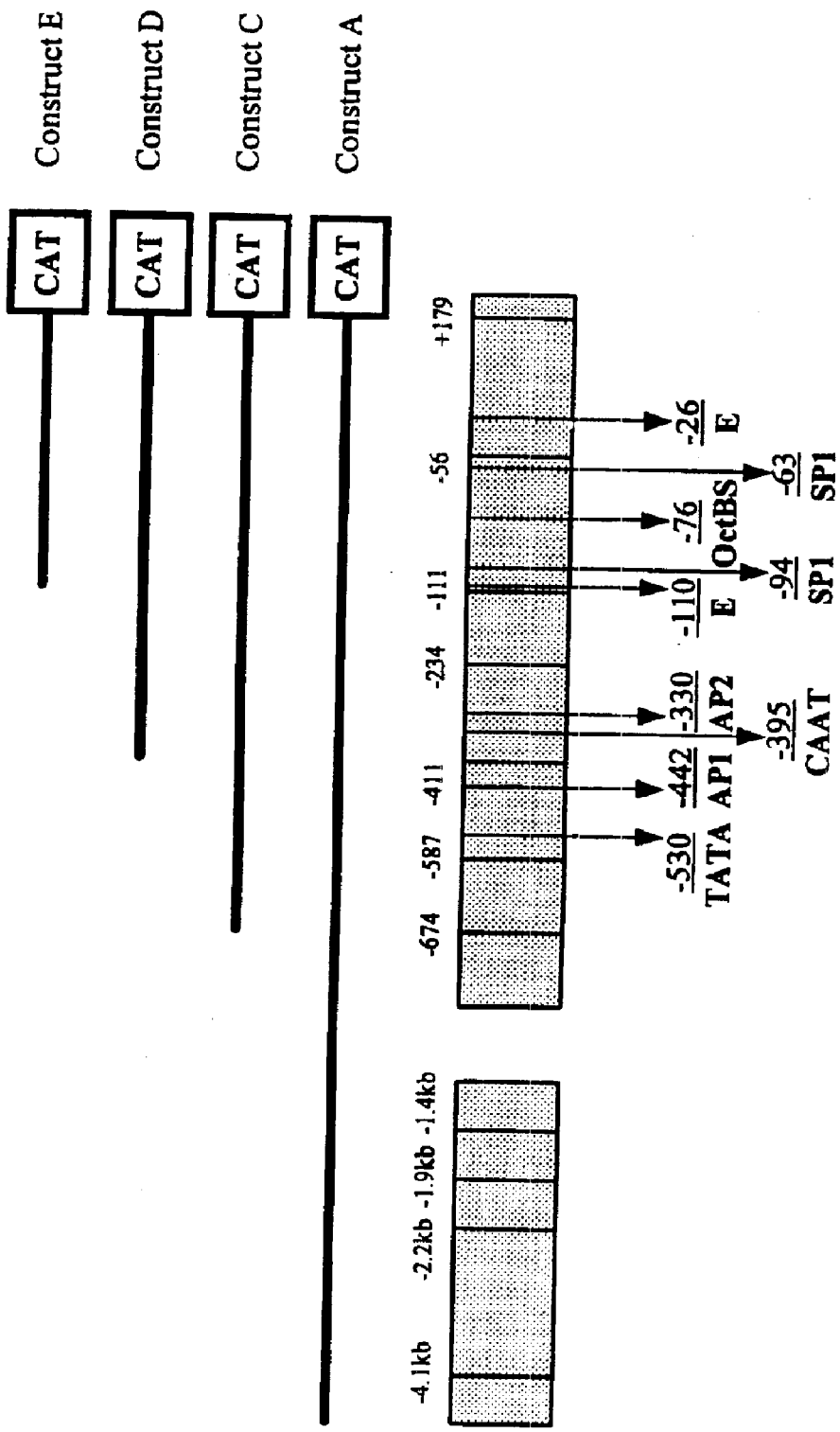
FIG. 19. Map of PKCβ promoter and lengths of deletion constructs. 5' deletion mutants of PKCβ gene cloned in the PKCβ-CAT plasmid were obtained from Dr. S. Ohno (Yokohama College of Medicine). The positions of cis-acting regulatory elements on the promoter region of PKC, gene are indicated. Construct A (−4.1 kb to +179 CAT), construct C (−674 to +179 CAT), construct D (−411 to +179 CAT) and construct E (−234 to +179 CAT) were transiently transfected into synchronized A10 cells.
Figure 20:
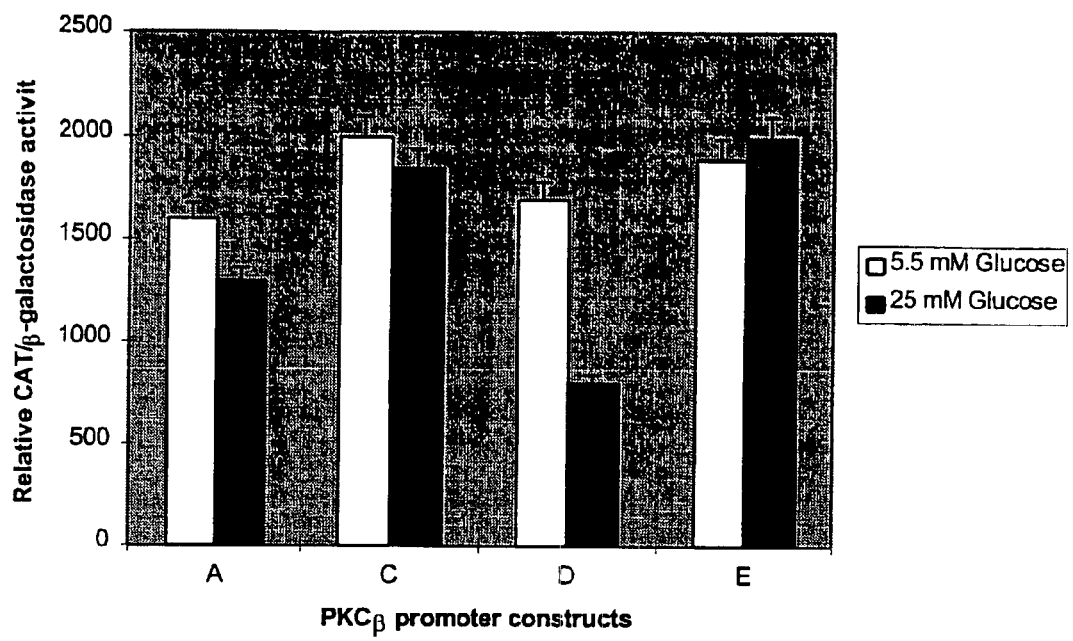
FIG. 20. Effect of high glucose on PKC, deletion constructs. Constructs A, C, D, and E as designated above, were transiently transfected into A10 cells synchronized for 48 hours in DMEM+0.5% FBS, re-initiated to proliferated in DMEM+10% FBS, using calcium phosphate-DNA precipitate along with β-galactosidase (1 μg) to normalize transfection efficiency. After overnight transfection, the cells were washed with DPBS and placed in fresh medium (DMEM+10% FBS) containing either 5.5 mM or 25 mM glucose. Cells were extracted after 6 hours and relative CAT/1-galactosidase activity was measured in control (5.5 mM glucose) and glucose (25 mM)-treated cells. Construct D showed maximum quenching of PKCβ promoter activity. This graph represents relative CAT/β-galactosidase activity for 3 individual experiments preformed in duplicate.

Our studies indicated that PKCβII protein levels "cycled" with synchronized A10 cells during a 24 hour period post re-initiation of the cell cycle with serum (Yamamoto et al., 1998, pp.349–358). We chose first to systematically study the effect of high glucose on PKCβ promoter activity in synchronized A10 cells. Glucose may be exerting its effect on PKCβ gene expression through a response element located in the common promoter upstream of the transcription start site as reported with L-PK and S14 gene expression in hepatocytes. Since PKCβ is a low copy gene, nuclear run-on assays were not a practical approach to examine transcriptional regulation. Hence, the PKCβ-CAT expression plasmids cloned by Dr. Ohno (Yokohama College of Medicine) (Niino, Y., S., S. Ohno, and K. Suzuki. 1992. Positive and negative regulation of the transcription of the human protein kinase C β gene. J. Biol. Chem. 267:6158–6163) were used to study transcriptional regulation of PKCβ gene expression by glucose. PKCβ promoter constructs with successive deletions of the 5' region cloned in front of a promoterless chloramphenicol acetyltransferase (CAT) as the reporter gene were transiently transfected into A10 cells (FIG. 19). pSV-β-Galactosidase was co-transfected with the CAT constructs to normalize the efficiency of transfection. Simultaneous positive and negative controls were carried out as described previously.

Figure 5:
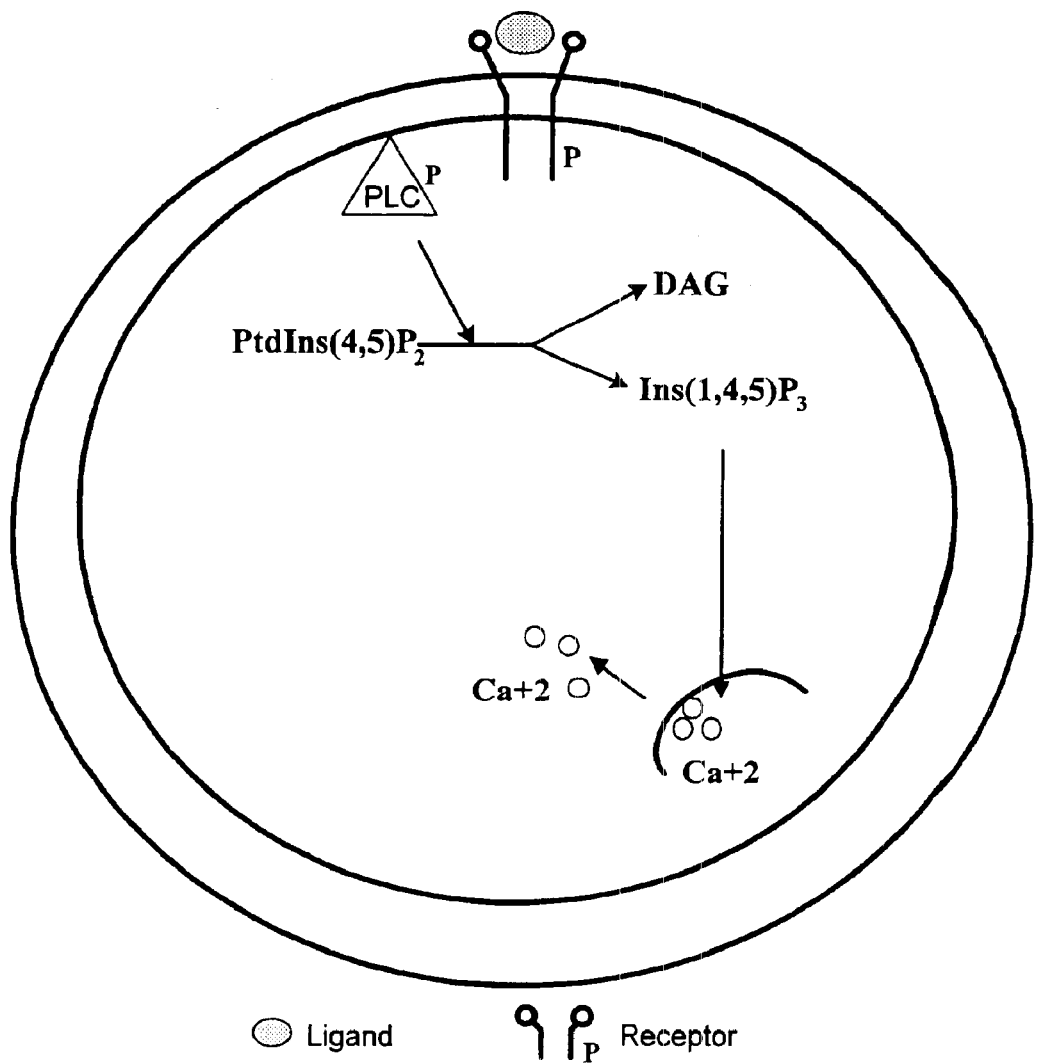
FIG. 5. Generation of PKC activators. Ligand binding to the receptor activates phospholipase C (PLC) which generates diacylglycerol (DAG) and $Ca^{+2}$. $PtdIns(4,5)P_2$: phosphotidylintositol 4,5-bisphosphate; $PtdIns(1,4,5)P_3$: phosphotidylintositol 1,4,5-trisphosphate.
Figure 6:
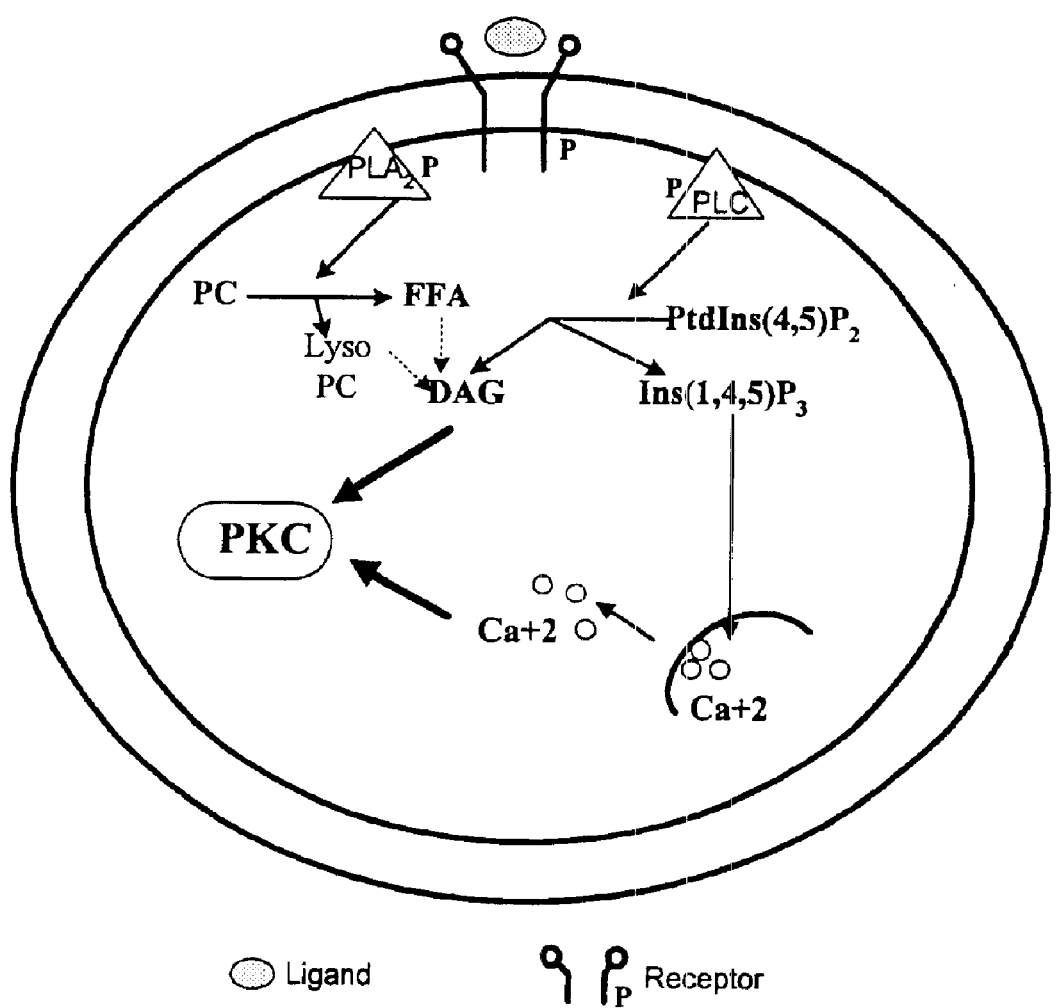
FIG. 6. Activation of PKC by diacylglycerol and $Ca^{+2}$. Ligand binding to the receptor activates phospholipase C (PLC) which hydrolyses phosphotidylintositol 4,5-bisphosphate $(PtdIns(4,5)P_2)$ to diacylglycerol (DAG) and $Ca^{+2}$. Phospholipase $A_2$ ($PLA_2$) is also activated which hydrolyses phosphocholine (PC) to lysophosphotidylcholine (Lyso PC) and free fatty acids (FFA). This results in increased levels of DAG thereby prolonging PKC activation for sustained cellular responses.
Figure 7:
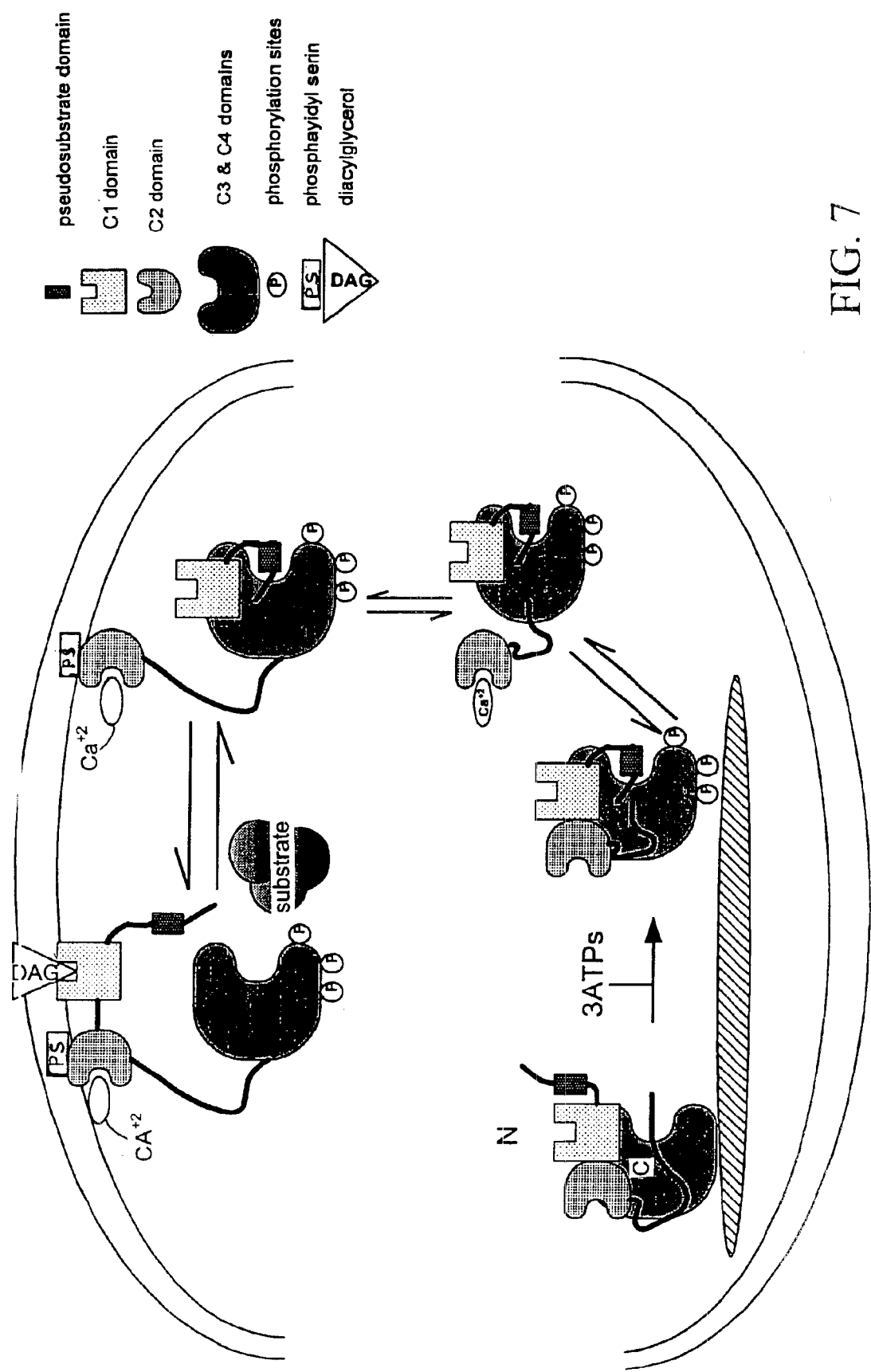
FIG. 7. Model for activation of PKC. Newly synthesized PKC is bound to the cytoskeletal. Upon phosphorylation, it translocates towards the membrane but is still inactive due to the pseudosubstrate binding. Diacylglycerol, $Ca^{+2}$ and phophotidylserine activate PKC which binds to the membrane via its C1 and C2 domains and is released from the pseudosubstrate inhibition.
Figure 8:
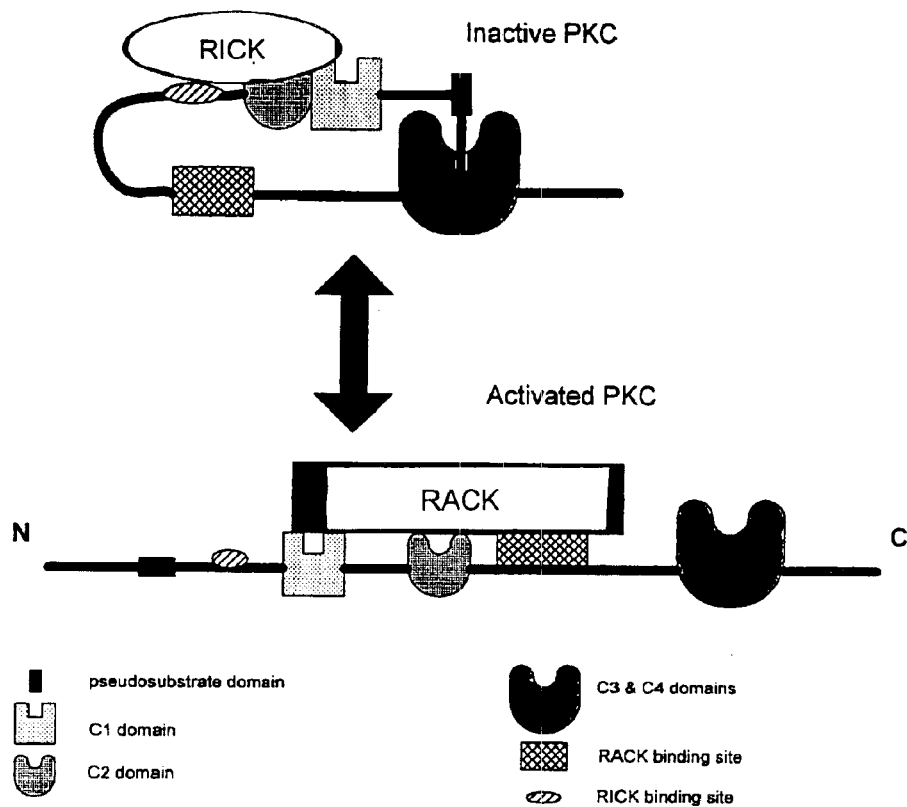
FIG. 8. Localization of PKC isozymes by anchoring proteins. Both active and inactive PKC isozymes are localized to their specific intracellular sites due to their binding to the specific anchoring molecules. Receptors for inactive C-kinase (RICKs) bind to the inactive PKC isozymes in the cell cytoskeleton in a phosphotidylserine-dependent manner. Receptors for active C-kinase (RACKs) bind to the activated PKC isozymes in a selective and saturable manner at a site distinct from the substrate-binding site.
Figure 9:
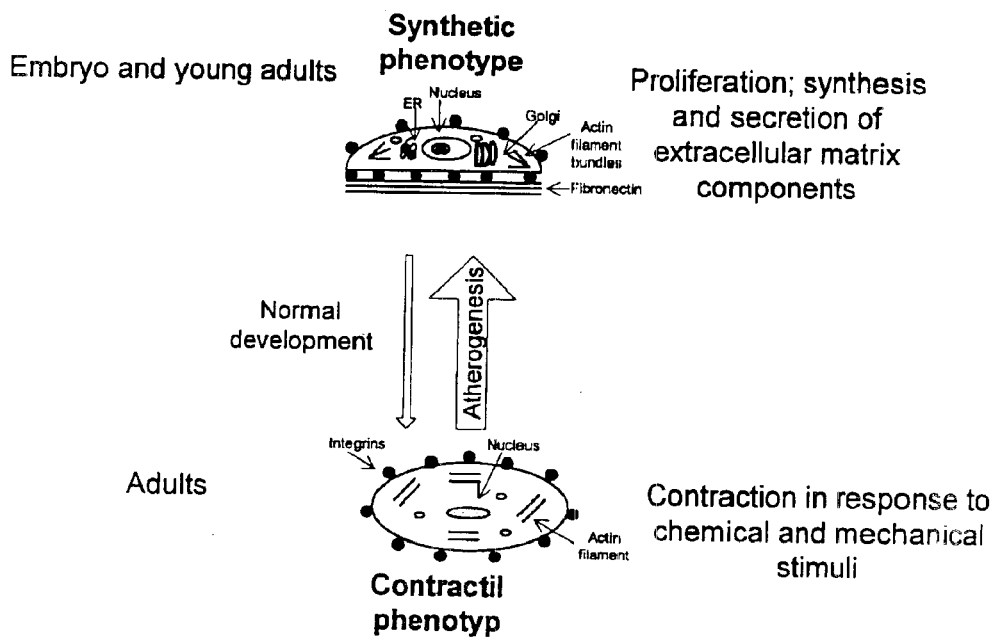
FIG. 9. Arterial smooth muscle cell phenotypes. In the contractile phenotype, the smooth muscle cells show a heterochromatic nucleus and abundant actin and myosin filaments. In the process of atherogenesis, the smooth muscle cell structure modifies to a synthetic phenotype that has a euchromatic nucleus, prominent ER and golgi complex and a decrease in the content of myofilaments. Cells in the synthetic phenotype produce extracellular matrix components that aid in proliferation.
Figure 10:
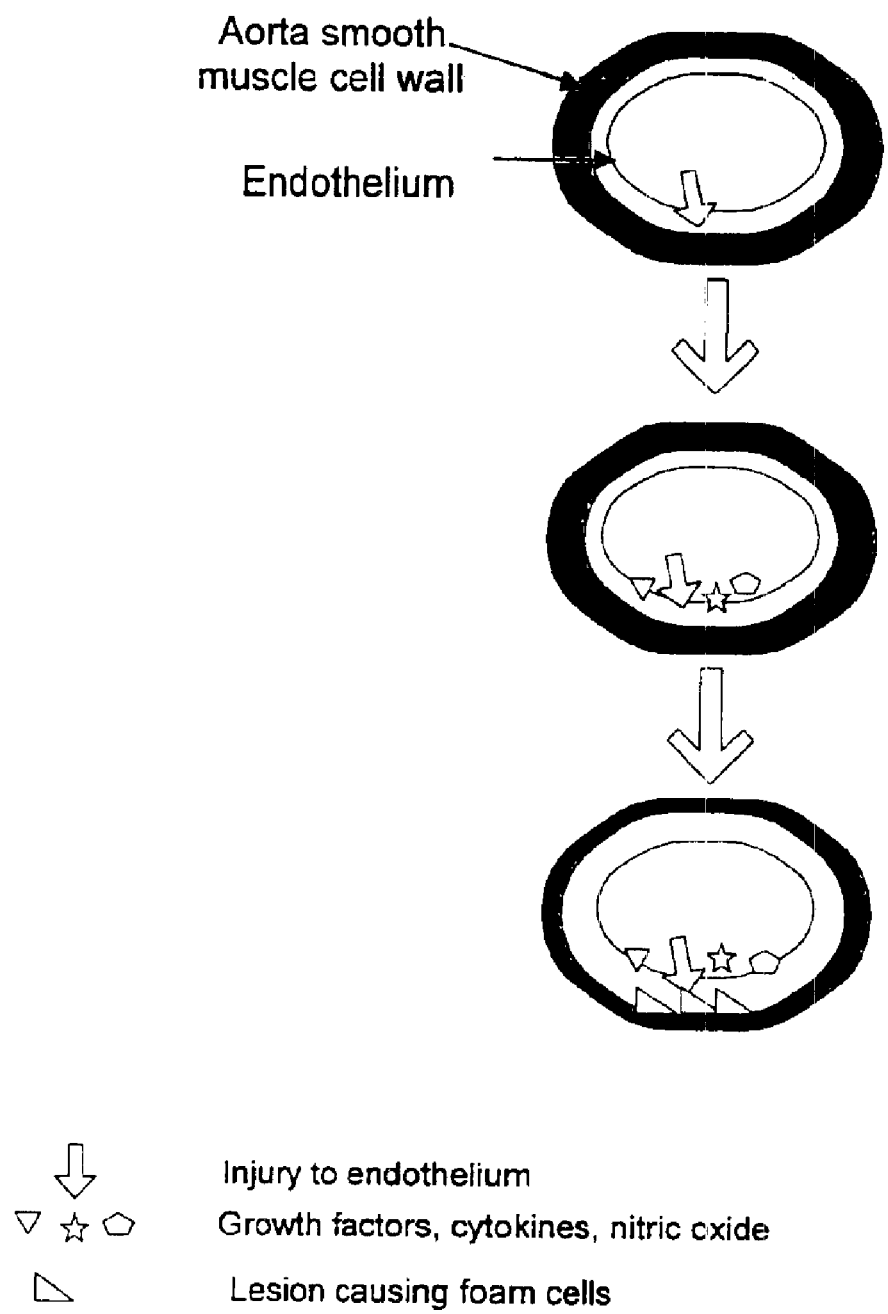
FIG. 10. Representation of the response-to-injury hypothesis of atherosclerosis proposed by Ross. Exposure to agents like oxidized LDL, toxins and viruses causes an injury to the endothelium and results in the release of growth factors, cytokines and nitric oxide. The smooth muscle cells migrate from the media to the arterial intima where they proliferate and deposit extracellular matrix components thereby forming a lesion.

Transcriptional repression of PKCβ promoter by transcription factors in response to high glucose was anticipated. However, in A10 cells incubated with high glucose (25 mM(for six hours, a moderate decrease or quenching in the PKCβ promoter activity of constructs A (−4.1 kb to +179CAT), C (−674 to +179CAT) and D (−411 to +179CAT) was observed (FIG. 5). Construct E (−234 to +179CAT) showed no quenching with glucose indicating that a putative carbohydrate response element had been deleted. Construct E contains the basal response elements required for promoter activity and was not affected by glucose concentrations. Thus construct D contained the elements involved in maximum quenching of promoter activity, presumably within a 177 bp region which was deleted in construct E. In parallel experiments, a control with 100 nM TPA increased the promoter activity ten-fold in all constructs. This confirmed the response of PKCβ basal promoter element with phorbol esters.

Figure 21:
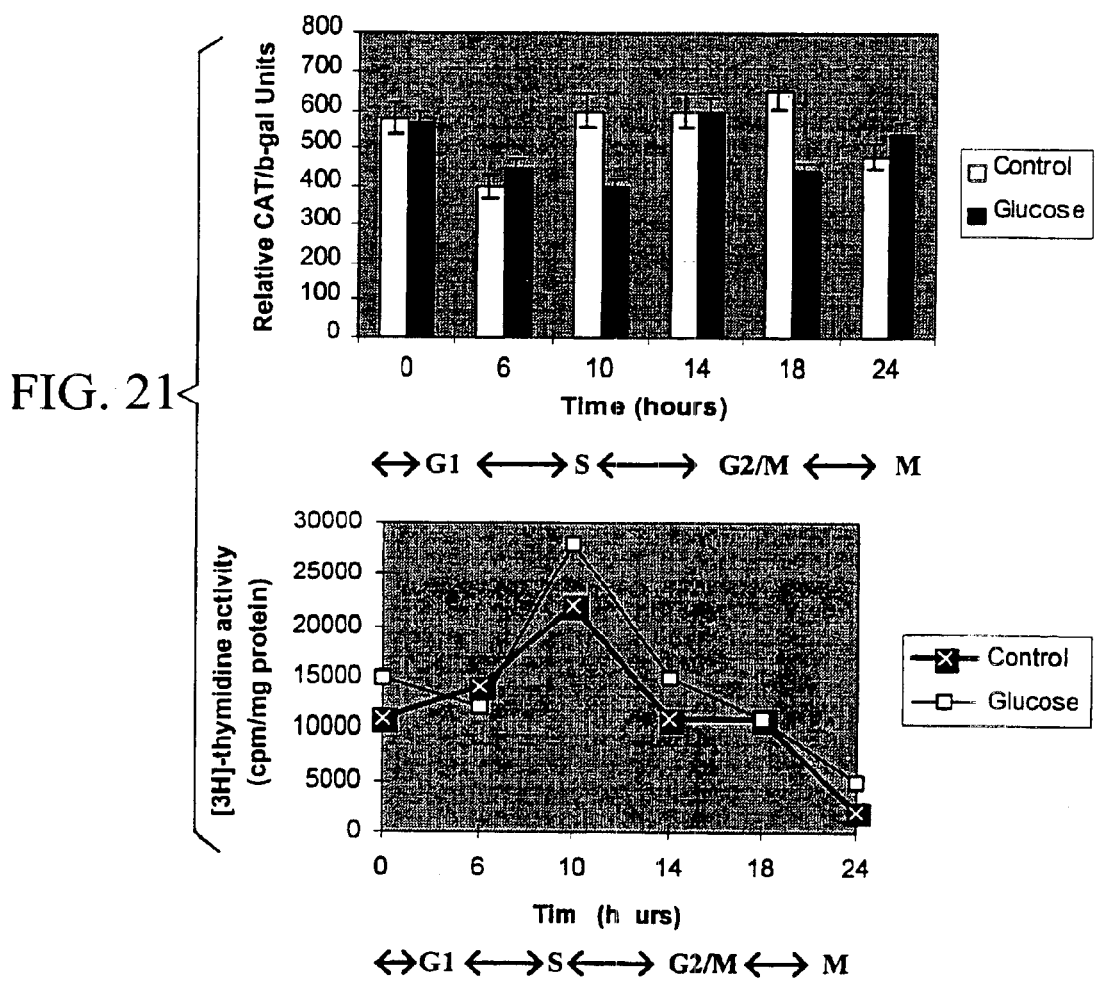
FIG. 21. Construct D quenches PKCβ promoter activity at 10 h post-synchronization corresponding to S phase. Construct D, as described in FIG. 19, was transiently co-transfected with β-galactosidase into synchronized A10 cells. Promoter activity in control (5.5 mM glucose) and glucose (25 mM)-treated cells following 6–24 hours of treatment was calculated as relative CAT/β-galactosidase units. Maximum quenching by high glucose of PKCβ promoter construct D (−411/+179CAT) was observed at 10 hours which is the peak of S phase as determined by $^3$[H]-thymidine uptake studies as described in the description. Error bars indicate ±S.E.M. Data shown is the mean of ±SE for triplicate determinations of an experiment that was repeated on three separate occasions with similar results. (* indicates significance at p<0.05).

In the case of transcriptional repression, DNA binding is inhibited by repressors blocking the binding site for a factor or forming a non-DNA-binding protein—protein complex resulting in inhibition of transcription. The reduction in promoter activity observed here, however, did not account for the dramatic down-regulating effect of glucose on total PKCβ mRNA. If glucose effects were mediated exclusively at the transcriptional level, total repression would have occurred. The reduction in promoter activity observed here is most likely explained as a quenching effect that involves interfering with transcriptional activation by a DNA-bound factor. An example of transcriptional quenching is illustrated by the yeast factor GAL80, which inhibits gene activation by the positively acting GAL4 protein in the regulation of galactose in yeast. Since the extent of quenching of the PKCβ promoter by glucose varied depending on the time points examined, the results suggested that as cells progress through the cell cycle, high glucose regulation of PKCβ gene expression may be cell cycle mediated. Simultaneous cell cycle studies and promoter activity of construct D (−411 to +179 CAT) in high glucose were determined. The results demonstrated an increase in the percentage of cells going into S phase in high glucose implying that quenching of PKCβ transcription may be related to cell cycle progression (FIG. 21).

PKCβ mRNA is Destabilized by Glucose

Figure 22A:
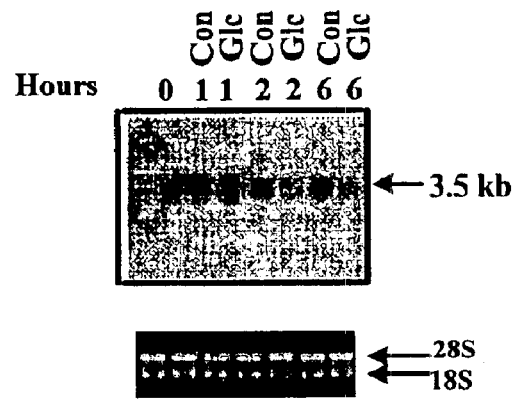
FIGS. 22A and 22B. Northern blot analysis of PKCβII mRNA in A10 cells treated with actinomycin D in the presence or absence of high glucose.
Figure 22B:
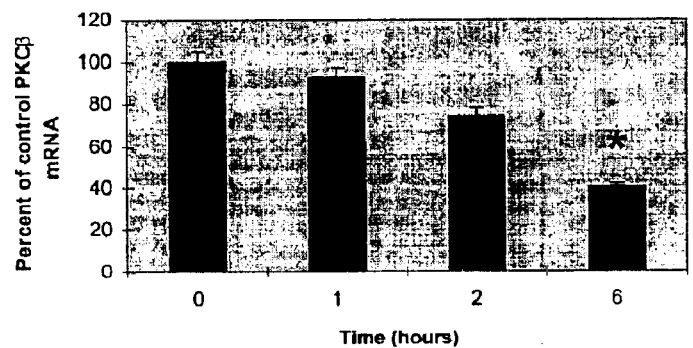

Since the quenching of PKCβ promoter activity by acute high glucose did not account for the 60–75% reduction in PKCβ mRNA levels as observed by northern blot analysis (FIGS. 18A and 18B), the major effect of glucose may be exerted post-transcriptionally. However, high glucose also diminished PKCβII protein levels, suggesting that high glucose could affect the stability of the PKCβII transcript at the post-transcriptional level. Northern blot analysis of PKCβ(I+II) mRNA level (see methods) was performed on total RNA from synchronized A10 cells. Upon re-initiation of proliferation by DMEM+10% FBS, A10 cells were pre-treated with actinomycin D for 30 minutes followed by incubation with normal or high glucose. The mRNA levels were detected using the full-length PKCβII cDNA probe which recognizes both PKCβI and PKCβII mRNA. A10 cells exposed to high glucose showed a decrease in PKCβ (I+II) mRNA levels within 2 hours of treatment (FIG. 22B) and levels further decreased to 60% of control by 6 hours. Thus, the results suggested that post-transcriptional destabilization of PKCβII mRNA by glucose was also occurring.

In Vitro Assay for mRNA Destabilization

Figure 23:
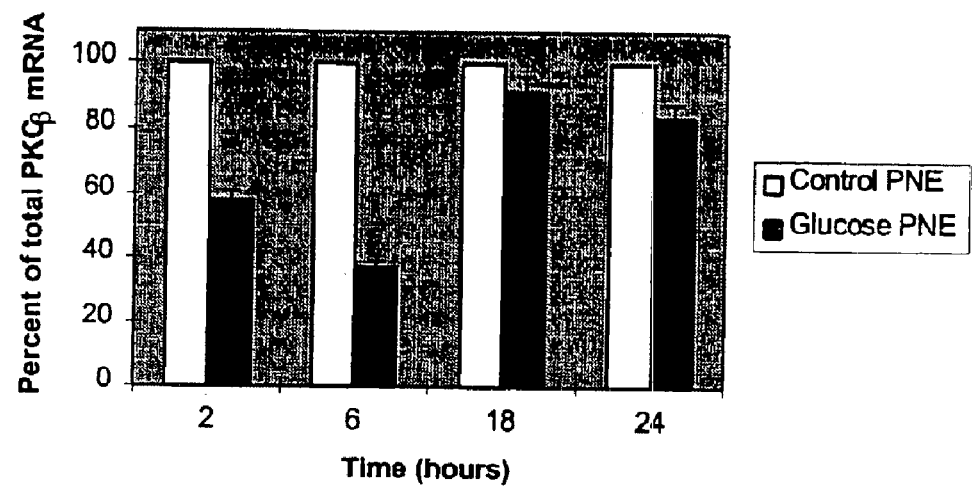
FIG. 23. In vitro assay for RNA stability. Post-nuclear extracts were prepared form A10 cells treated with either 5.5 mM glucose (control cells) or 25 mM glucose (glucose-treated cells) for 2, 6, 18, or 24 hours. Total RNA (previously extracted from synchronized A10 cells) was incubated for 30 minutes at 4° C. with 2.7% (vol/vol) post-nuclear extracts from control (5.5 mM glucose) or 25 mM glucose-treated A10 cells in a 50/1 total reaction volume. Northern blot analysis for PKCβ(I+II) mRNA was then performed on the RNA as described in methods. Images of the 3.5 kb bands were quantitated by phosphoimaging and are representative of four individual experiments with similar results. The graph shows the total PKC(β1+II) mRNA levels remaining after incubation with post-nuclear extracts from glucose-treated cells plotted as a percent of the total PKC(βI+II) mRNA in the respective control incubations with post-nuclear extracts from cells treated with 5.5 mM glucose. Protein concentrations of control (5.5 mM glucose) post-nuclear extracts (control PNE) and 25 mM glucose-treated post-nuclear extracts (glucose PNE) at 2 hours were 2.5 mg/ml and 2.23 mg/ml respectively; at 6 hours, protein levels were 1.34 mg/ml and 1.34 mg/ml respectively; at 18 hours, levels were 1.3 mg/ml and 1.25 mg/ml respectively; and at 24 hours, levels were 1.22 mg/ml and 1.27 mg/ml.
Figure 24:
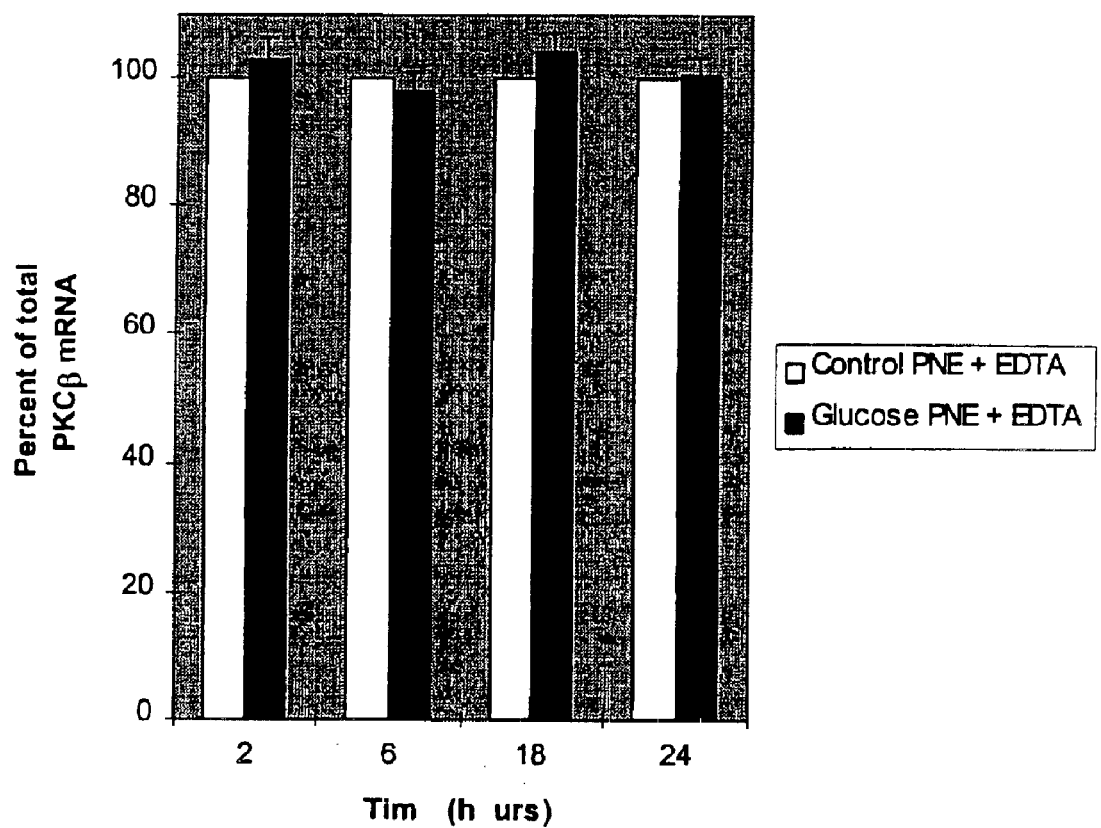
FIG. 24. In vitro assay for RNA stability in the presence of EDTA. No degradation of total RNA by glucose-treated post-nuclear extract was observed when 50 mM EDTA was added to the reaction mix as described above. Similar results were obtained in three separate experiments.

To assess the involvement of a nuclease activity in the destabilization of PKCβ mRNA by glucose, an in vitro RNA stability assay was performed (see, for example, Wager, R. E. and R. K. Assoian. 1990. A phorbol ester-regulated ribonuclease system controlling transforming growth factor B1 gene expression in hematopoietic cells. Mol. Cell. Biol. 10:5983–5990). A10cells incubated with 5.5 mM or 25 mM glucose for 2 h, 6 h, 18 h and 24 h were used to prepare control post-nuclear extracts (control PNE) or glucose-treated post-nuclear extracts (glucose PNE). Total RNA isolated from untreated A10 cells was incubated with 2.7% (vol/vol) post-nuclear extracts or glucose-treated post-nuclear extracts from A10 cells in 501 total volume of extract buffer. As a positive control, RNA incubated without post-nuclear extracts was used. A reaction with no RNA served as the negative control. Since involvement of divalent cations is a feature of some ribonucleases that regulate mammalian RNA turnover, EDTA was added to post-nuclear extracts to distinguish nuclease activity from cyclizing RNases and acid lysosomal RNase. Northern blot analysis was then performed to detect non-degraded PKCβ(I+II) mRNA. Incubation of RNA with post-nuclear extracts from synchronized A10 cells treated with 25 mM glucose for 2 hours and 6 hours showed 45% and 65% decreases, respectively, in PKCβ(I+II) RNA levels while incubation for 18 hours and 24 hours showed 8% and 12% decreases, respectively, in PKCβ(I+II) RNA levels (FIG. 23). No degradation of RNA was observed in the presence of EDTA, either in the control or high glucose treated post-nuclear extracts (FIG. 24). These results indicate the activation of a divalent cation-dependent nuclease activity by high glucose. The destabilization of PKCβ(I+II) mRNA by glucose accounted for a significant down-regulation of PKCβII expression although these observations suggested that destabilization of PKCβII mRNA occurred as an early event in the regulation of mRNA processing by high glucose.

Specificity of mRNA Destabilization by Glucose

Figures 26A, 26B:
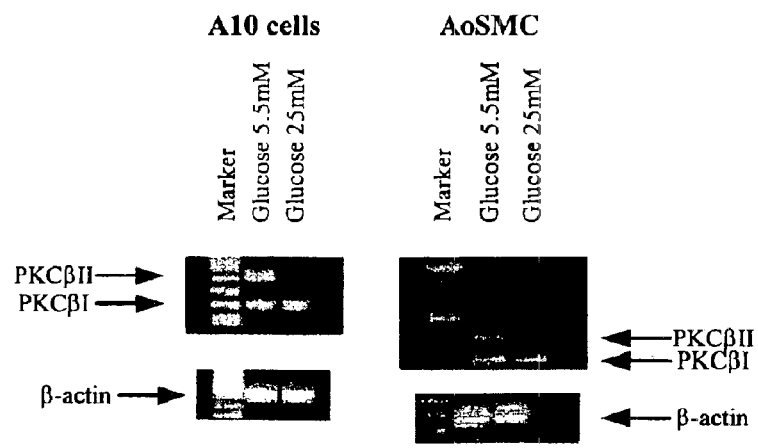
FIGS. 26A and 26B. High glucose destabilizes PKCβII mRNA. RT-PCR was performed on total RNA isolated from A10 cells synchronized by serum starvation for 48 hours or from primary cultures of AoSMC from humans synchronized by serum starvation for 72 hours. Cells were re-initiated to proliferate by serum introduction to the basal medium and incubated with 5.5 mM glucose (control) or 25 mM glucose (glucose-treated) for 4 hours. The first strand cDNA synthesized was amplified using a sense primer to the common, C4, domain and antisense primer to the PKCβI exon. The PCR product size was 187 bp for PKCβI; 404 bp for PKCβII and 550 bp for β-actin. PKCβII mRNA was decreased >95% by 25 mM glucose treatment while PKCβI mRNA remained unchanged. No change was observed in the β-actin PCR products both in 5.5 mM and 25 mM glucose treated cells. Results are representative of an experiment repeated on five occasions.

Since a full length PKCβ cDNA probe was used for analysis of PKCβ(I+II) RNA levels by the northern blot analysis, RT-PCR was performed on total RNA from A10 cells to determine the specificity of high glucose to down-regulate PKCβII mRNA rather than PKCβII mRNA. Previously, it had been demonstrated that mature PKCβI mRNA results from differential processing resulting in PKCβII exon inclusion into PKCβI mRNA transcript (Chalfant et al., 1995, pp.13326–13332; Ono et al., 1987, pp.1116–1120). Thus, the PKCβII transcript contains the PKCβI exon with the poly A tail and a common 3' untranslated region (FIG. 25). Inclusion of the alternatively spliced exon encodes a stop codon such that the PKCβI exon facilitates poly-adenylation but the exon is not translated, thereby generating PKCβII protein. Primers were designed for the upstream common kinase region (C4) (—sense primer) and the PKCβI exon (—antisense primer) for simultaneous amplification of both PKCβI and -βII messages by RT-PCR. In control A10 cells (5.5 mM glucose), both PKCβI and PKCβII PCR products were detected. Although, this assay is semi-quantitative, the ration of PKCβII to PKCβI mRNA was about 2 to 1. In glucose-treated (25 mM) A10 cells, PKCβII PCR product decreased >90% while PKCβI mRNA levels did not show any significant change. β-actin mRNA levels remained constant in both control and glucose-treated A10 cells (FIG. 26). Thus, PKCβII mRNA was specifically destabilized in response to 25 mM glucose.

To extend the physiological relevance of the down-regulation of PKCβII by high glucose, we repeated the RT-PCR described above using primary cultured aortic smooth muscle cells from humans (AoSMC CC2571, CLONETICS Normal Human Cell System). In high glucose medium (25 mM glucose), AoSMC showed a >95% decrease in PKCβII mRNA while PKCβI mRNA was not significantly affected. β-actin mRNA levels remained the same in both control (5.5 mM glucose) and glucose-treated (25 mM glucose) AoSMC (FIG. 26). Since cells from human primary culture responded in the same manner, the A10 cells proved to be a reliable model for studying the effects of high glucose on PKCβ gene expression in vascular smooth muscle cells.

Figure 28:
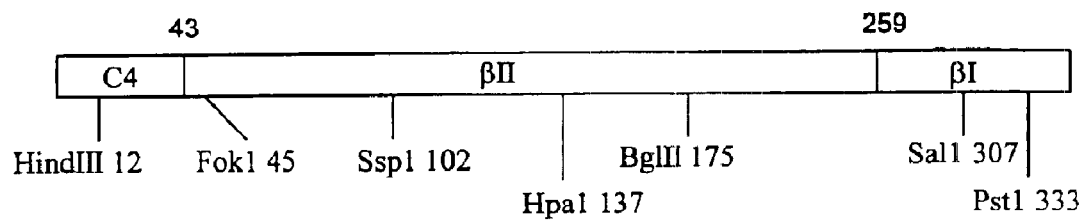
FIG. 28. PKC βII cDNA (350 bp) restriction sites map.

PKCβII mRNA is Generated Via Exon Inclusion of the Alternatively Spliced PKCβ Pre-mRNA in VSMC To verify that the amplified product was PKCβII cDNA, the 404 bp band corresponding to the PKCβII cDNA was excised from the gel and cloned into the pCR-blunt vector. Dideoxy sequencing and restriction digestion confirmed that the mature PKCβII mRNA was a result of a 216 bp exon inclusion via alternative splicing of the PKCβmRNA. The sequence for up to 350 bp is shown in FIG. 27 while the restriction sites map is depicted in FIG. 28.

PKCβII mRNA Was Destabilized When AoSMC Cells Were Incubated With 25 mM Glucose

Figure 29:
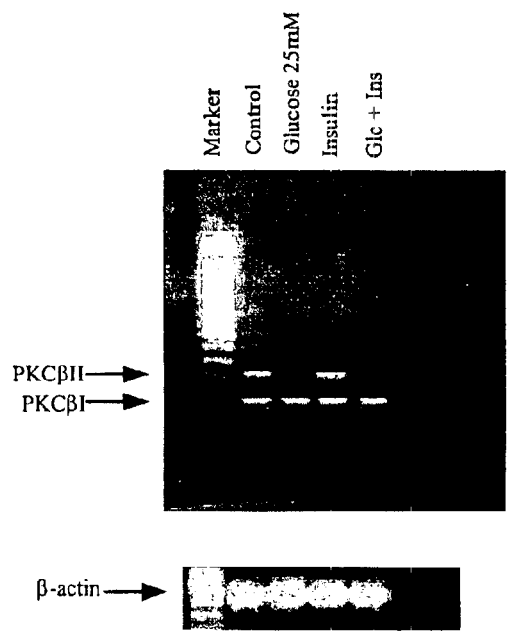
FIG. 29. Effect of glucose and insulin on PKCβII mRNA in aorta smooth muscle cells. RT-PCR was performed on total RNA isolated from primary cultures of AoSMC from humans incubated with 5.5 mM glucose (control), 25 mM glucose (glucose-treated), 100 nM insulin or mM glucose +100 nM insulin for 4 hours. The first strand cDNA synthesized was amplified using a sense primer to the common, C4, domain and antisense primer to the PKCβI exon. The PCR product size was 187 bp for PKCβI; 404 by for PKCβII and 550 bp for β-actin. In control cells (lane 1), bother PKCβI and -βII mRNA were detected; PKCβII mRNA was decreased >95% by 25 mM glucose treatment while PKCβI mRNA remained unchanged (lane 2); 100 nM insulin (lane 3) did not significantly affect either PKCβI or -βII mRNA; 25 mM glucose +100 nM insulin (lane 4) PKCβII mRNA was decreased by 60%. No change was observed in the β-actin PCR products both in 5.5 mM and 25 mM glucose treated cells. Results are representative of an experiment repeated on five occasions.

Insulin activates PKC and regulates the activity of glucose transporters (GLUT4) which are essential for regulated glucose uptake in quiescent smooth muscle cells. Since efficient transport into muscle cells is critical for glucose metabolism, we determined if insulin affected the stability of PKCβ isozymes by high glucose. AoSMC were synchronized by serum starvation ad described in methods and upon re-initiation of the cell cycle with SmGM containing 5% FBS, were treated with either 5.5 mM glucose (normal glucose), 25 mM glucose (high glucose), 100 nM insulin or 25 mM glucose +100 nM insulin for 4 hours. Total RNA was isolated and products quantified as percent PKCβII present in the total PKC(βI+βII) mRNA. Insulin did not destabilize PKCβI or PKCβII mRNA (FIG. 29) but in the presence of high glucose and insulin, PKCβII mRNA was diminished by 60%. Thus insulin-stimulated PKC activation and glucose uptake was not associated with high glucose-induced destabilization of PKCβII mRNA. Insulin enables glucose uptake by the cells and results in the metabolism of glucose at a higher rate. This suggested that the buildup of free glucose in the cytosol may be essential for the destabilization of PKCβI mRNA by high glucose.

Metabolism of Glucose to Glucosamine is Not Required

Figure 30:
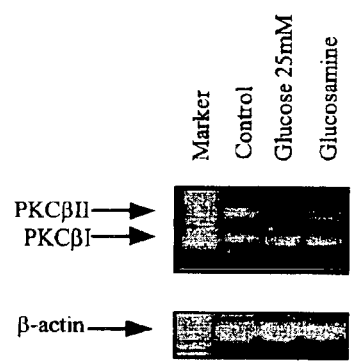
FIG. 30. Glucosamine does not affect PKCβII mRNA stability. RT-PCR was performed on total RNA isolated from synchronized A10 cells incubated with 5.5 mM glucose (control), 25 mM glucose (glucose-treated) or 10 mM glucosamine for 4 hours. The first strand cDNA synthesized was amplified using a sense primer to the common, C4, domain and antisense primer to the PKCβI exon. The PCR product size was 187 bp for PKCβI; 404 bp for PKCβII and 550 bp for β-actin. Glucosamine did not destabilize PKCβI or -βII mRNA.

Glucosamine, a metabolite of glucose and a product of the hexosamine pathway, has been implicated in the regulation of transforming growth factor-α gene expression in VSMC (Sayeski et al., 1996, pp.15237–15243; McClain et al., 1992, pp.8150–8154.) and other transcriptionally regulated genes. Although, glucosamine effects were primarily associated with transcriptional regulation, we investigated whether glucose also mediated its regulation of the PKCβII transcript stability via glucosamine. Synchronized A10 cells were treated with 5.5 mM glucose (normal glucose), 25 mM glucose or glucosamine (10 mM in the presence of 5.5 mM glucose) for 4 hours prior to RNA isolation and analysis (FIG. 30). Glucosamine did not affect either PKCβI or –βII mRNA. Thus, further metabolism of glucose by the hexosamine biosynthetic pathway was not involved in the destabilization of PKCβII transcript by glucose.

Glucose Analogs Mimic Its Effect

Figure 31:
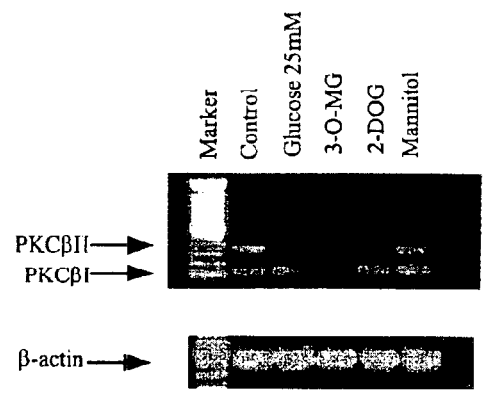
FIG. 31. Effect of glucose metabolites on PKCβI mRNA stability. Synchronized A10 cells upon re-initiation of the cell cycle by DMEM containing 10% FBS were treated with 5.5 mM glucose (lane 1, control), 25 mM glucose (lane 2, glucose), 25 mM 2-deoxyglucose (lane 3, 2-DOG), 25 mM 3-O-methylglucose (lane 4,3-O-MG) or 5.5 mM glucose +19.5 mM mannitol (lane 5) for 4 hours. Total RNA was extracted and 2 μg of RNA was used to perform RT-PCR analysis. The first strand cDNA synthesized was amplified using a sense primer to the common, C4, domain and antisense primer to the PKCβI exon. The PCR product size was 187 bp for PKCβI; 404 bp for PKCβII and 550 bp for β-actin. 2-DOG and 3-O-MG destabilized PKCβII mRNA while mannitol, the osmotic control did not.

To further explore whether glucose is required to be metabolized in order to down-regulate PKCβII mRNA, we studied the effects of glucose analogs on PKCβII and -βII mRNA levels. A10 cells were synchronized by serum starvation as described supra and upon re-initiation of the cell cycle with DMEM containing 10% FBS, were treated with 5.5 mM glucose (normal glucose), 25 mM glucose, 25 mM 2-deoxyglucose, 25 mM 3-O- methylglucose or 5.5 mM glucose +19.5 mM mannitol (osmotic control) for 4 hours. 2-deoxyglucose (2-DOG), is transported into the cell and phosphorylated to 2-deoxyglucose-phosphate but cannon be metabolized further (See, for example, Patel, N. A., C. E. Chalfant, M. Yamamoto, J. E. Watson, D. C. Eichler, and D. R. Cooper. 1999. Acute hyperglycemia regulates transcription and post-transcriptional stability of PKCβII mRNA in vascular smooth muscle cells. FASEB J. 13). As seen in FIG. 31, 2-DOG (25 mM) destabilized PKCβII mRNA.

This suggested that the metabolism of glucose beyond the glucokinase step is not required for the down-regulation of PKCβII mRNA. Nest, we studied 3-O-methylglucose (3-O-MG), an analog which can be transported into cell but not metabolized further. 3-O-Methylglucose (25 mM) also destabilized PKCβII mRNA and, to a lesser extent, PKCβI mRNA. These results suggested that further metabolism by the hexose mono-phosphate shunt was not involved. Furthermore, glucose need not be phosphorylated to bring about its effect, thereby eliminating the regulation by hexokinase in PKCβII gene expression. The levels of PKCβI and -βII mRNA remained unchanged with mannitol treatment, the osmotic control.

Figure 32:
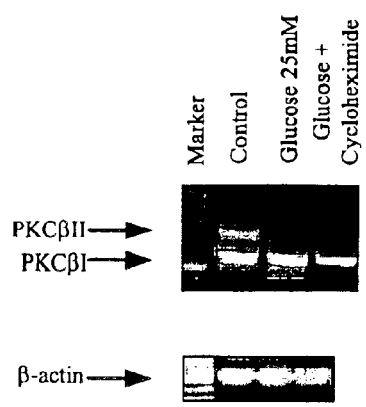
FIG. 32. Effect of cycloheximide on glucose-induced PKCβII destabilization. Synchronized A10 cells upon re-initiation of the cell cycle with DMEM containing 10% FBS were pre-incubated for 30 minutes with 20 mM cycloheximide followed by the addition of glucose. Total RNA was isolated and RT-PCR was performed on 2 μg of RNA. The first strand cDNA synthesized was amplified using a sense primer to the common, C4, domain and antisense primer to the PKCβI exon. The PCR product size was 187 bp for PKCI; 404 bp for PKCβII and 550 bp for β-actin. Lane 1:5.5 mM glucose, control cells; lane 2:25 mM glucose and lane 3:25 mM glucose +cycloheximide. Cycloheximide did not block the ability of glucose to destabilize PKCβII mRNA.

New Protein Synthesis is Not Required for Destabilization of PKCβII mRNA by Glucose Even though glucose effects on PKCβII destabilization were detected in 2 hours, it was still possible that a new protein was expressed in response to glucose. To investigate this, synchronized A10 cells (achieved by serum starvation as described in methods) upon re-initiation of the cell cycle with DMEM containing 10% FBS, were treated with 5.5 mM glucose (normal glucose), 25 mM glucose, or pre-incubated with 20 mM cycloheximide for 30 min followed by the addition of 25 mM glucose. High glucose destabilized PKCβII mRNA in the presence of cycloheximide indicating that glucose did not signal the synthesis of a new protein but likely activated a protein already present in the cytosol (Table 5) (FIG. 32).

An inhibitor of translation such as cycloheximide induces a rapid stabilization of the message (Ross, 1995, pp.423–450). Since cycloheximide did not alter the glucose-induced destabilization by glucose, it suggests that this process is independent of translation.

Kinase Inhibitors Implicate a PKC-dependent Pathway

Inhibitors of various kinases were used to elucidate the cascade of events involved in the glucose-mediated destabilization of PKCβII mRNA. The choice of concentrations used and the incubation times were based on previous observations. Phosphatidylinositol 3-kinase (PI 3-kinase) is a mediator of transmitting signals from upstream activators to downstream targets like PKC family (Palmer et al., 1995a, pp.22412–22416), p70-S6 kinase (Chung et al., 1994, pp.71–75), glucose transporter GLUT4 (Hara et al., 1994, pp.7415–7519), serine/threonine kinase Akt/Rac (Franke et al., 1998, Ridley et al., 1992, pp.401–410). To determine the possible involvement of PI 3-kinase, synchronized A10 cells were pre-incubated for 30 minutes with LY 294002 (20 μM), a specific inhibitor of PI 3-kinase prior to high glucose indicating the possible involvement of a PI 3-kinase-dependent downstream kinase pathway (Table 5).

TABLE 5

Effect of Inhibitors of several signaling pathways.

| INHIBITOR | TARGET | N VALUE | PERCENT OF PKCβII mRNA POST-GLUCOSE TREATMENT |
|---|---|---|---|
| None (5.5 mM glucose control) | NA | 6 | 100% |
| None + Glucose (25 mM) | NA | 6 | 5% |
| Glucose + Cyclohexi-mide (20 mM) | Protein synthesis | 5 | 10% |
| Glucose + LY 294002 (20 μM) | PI 3-kinase | 6 | 90% |
| Glucose + CG 41251 (5 μM) | PKC isozymes | 5 | 100% |
| Glucose + PD 98059 (20 μM) | MEK | 5 | 5% |
| Glucose + AG-490 (5 μM) | JAK | 5 | 5% |
| Glucose + Rapamycin (1 μM) | p70/85 S6 kinase | 5 | 5% |
| Glucose + Herbimycin A (1 μM) | Tyrosinc kinase | 5 | 90% |

Figure 11:
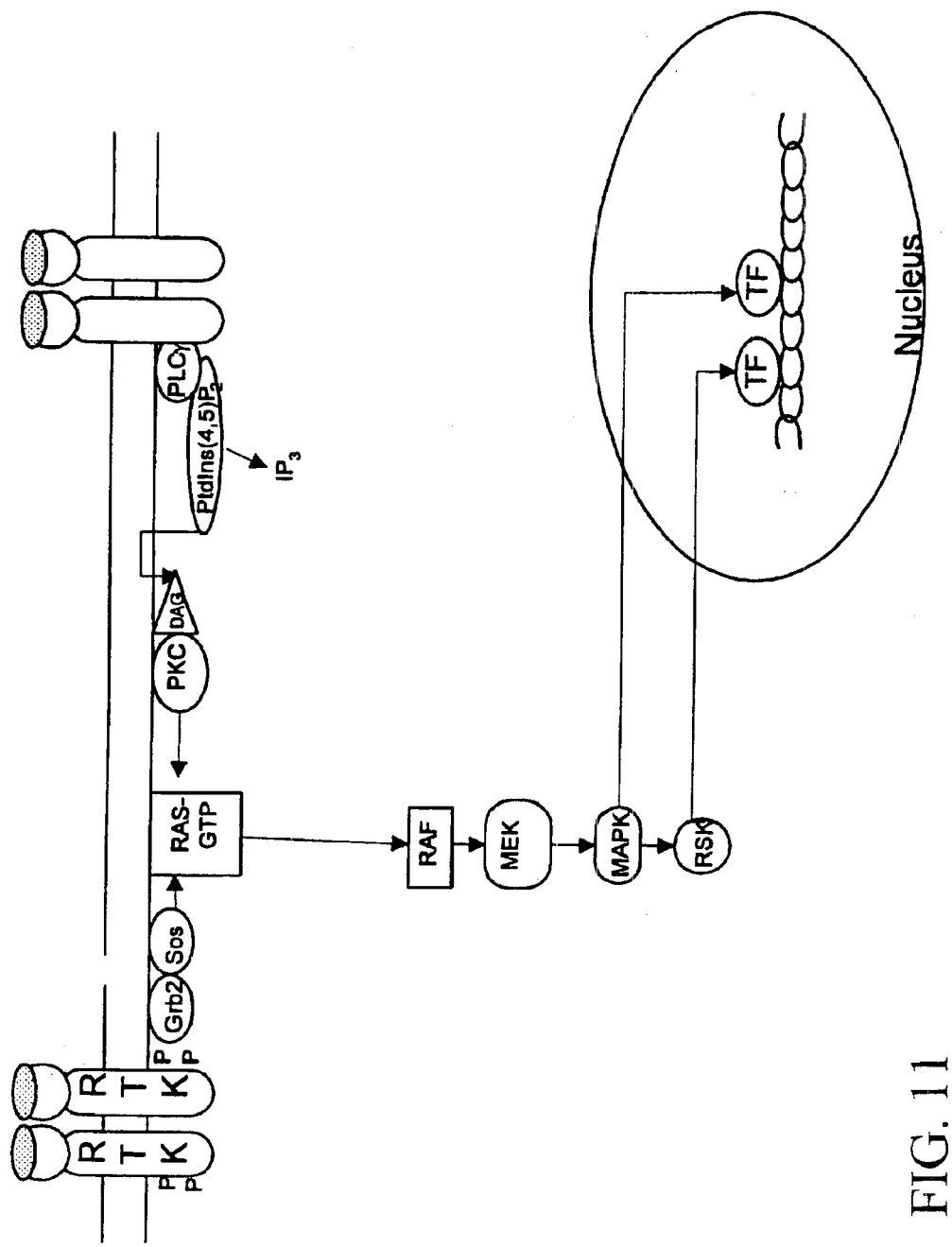
FIG. 11. The MAP kinase pathway transduces the signal from the membrane to the nucleus. Receptor tyrosine kinase (RTK) phosphorylation upon ligand binding activates Sos-Grb2 which further activates Ras. PKC is also an activator of Ras. The downstream target of Ras is Raf which can activate Mek. Mek phosphorylates MAP kinase which together with its target, ribosomal S6 kinase (Rsk) can translocate to the nucleus and activate transcriptional factors (TF) to regulate gene expression.
Figure 12:
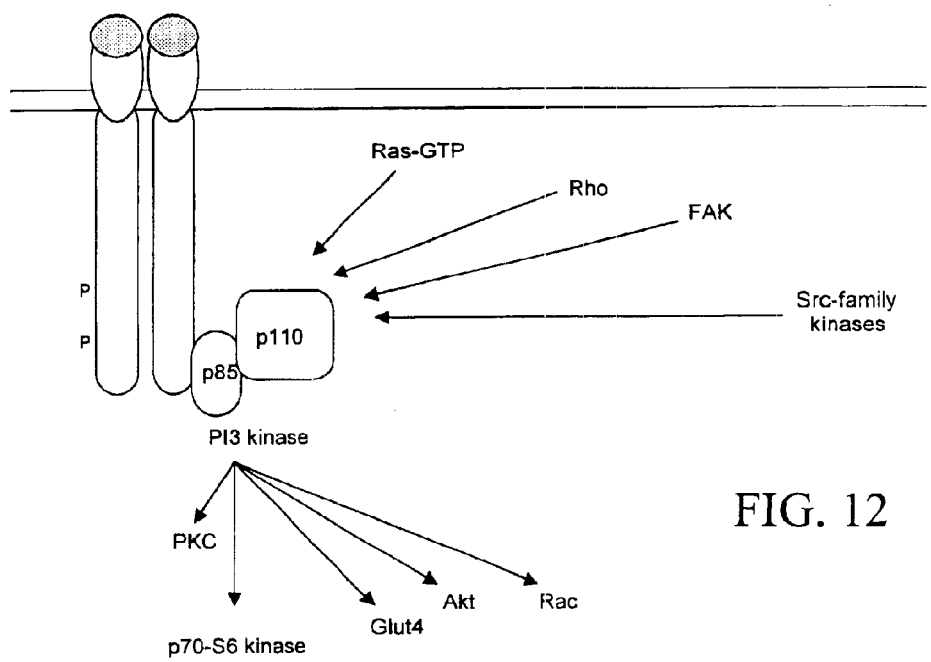
FIG. 12. The role of phosphoinositide 3-kinase (PI3 kinase) in signal transduction. Growth factor receptors with intrinsic tyrosine kinase activity recruit and activate P13 kinase. The upstream activators and downstream targets of P13 kinase are shown.
Figure 14:
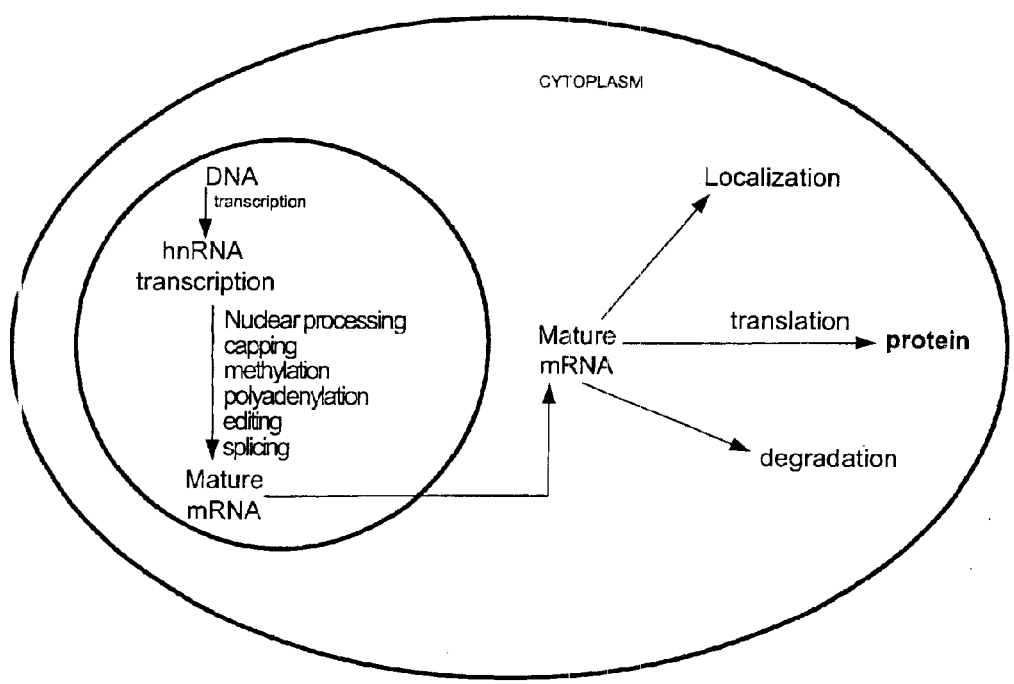
FIG. 14. The fate of mRNA in mammalian cells. RNA polymerase II synthesizes the heteronuclear RNA (hnRNA) transcript form the genomic DNA that undergoes post-transcriptional modifications before the mature mRNA is translocated into the cytoplasm. According to the cellular signals, the mRNA is either translated to protein or it can undergo degradation. Localization of mRNA to free, cytoskeletal-bound or membrane-bound polysomes also takes place in the cytoplasm.
Figure 13:
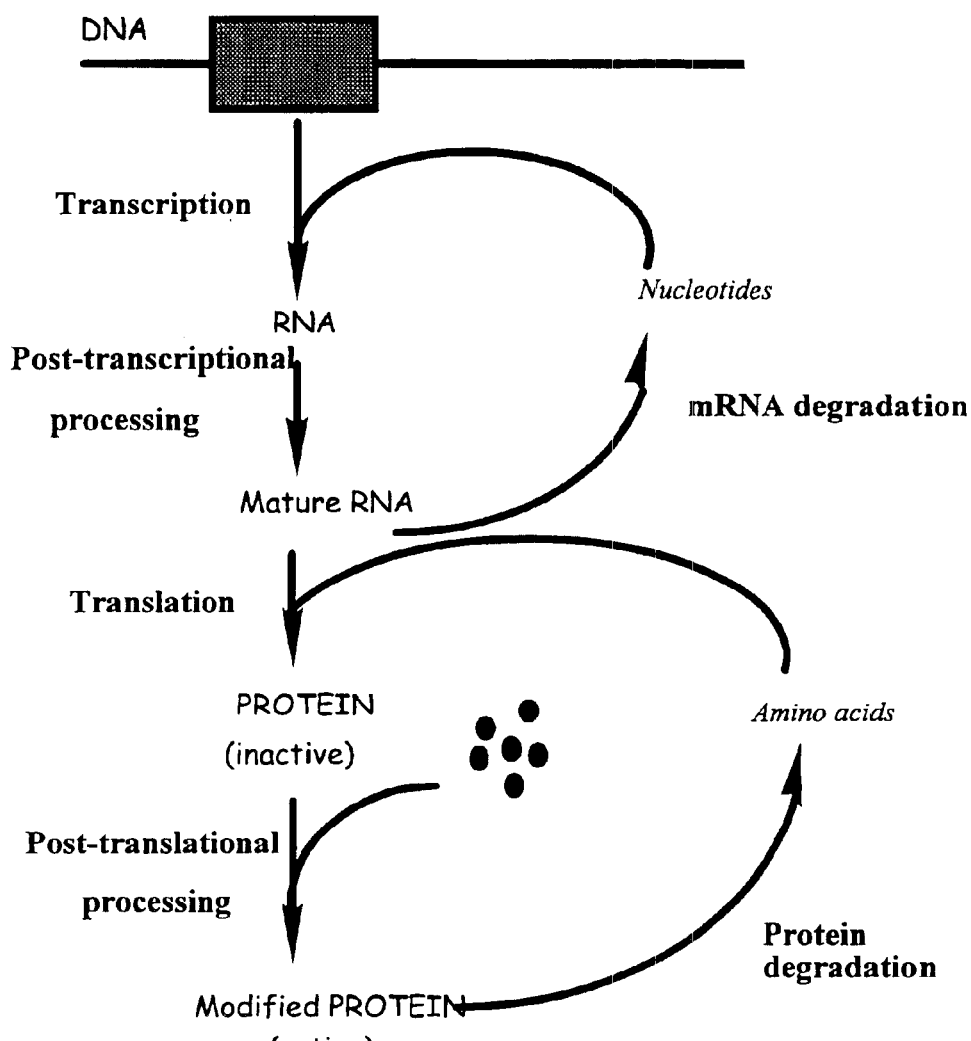
FIG. 13. Levels of eukaryotic gene regulation. DNA is transcribed to RNA which upon post-transcriptional modification is translated to proteins. The pool of nucleotides and amino acid is refurbished by mRNA and protein degradation, respectively.
Figure 15:
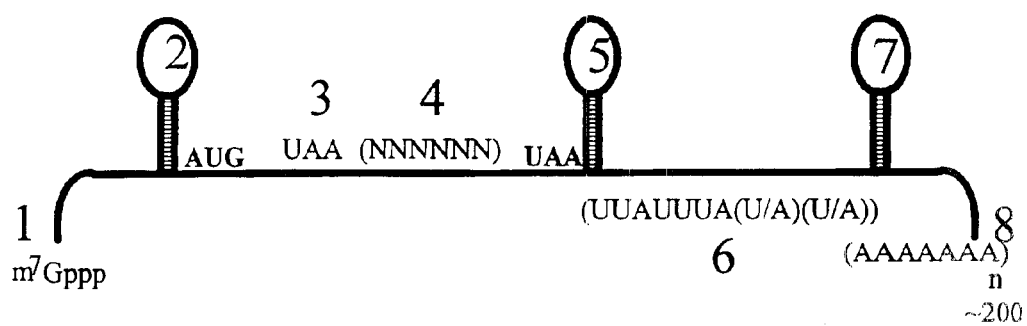
FIG. 15. Representation of the structural elements involved in regulating mRNA stability. The cis-elements to which trans-acting factors bind to modulate the half-life of the mRNA are depicted.
Figure 33:
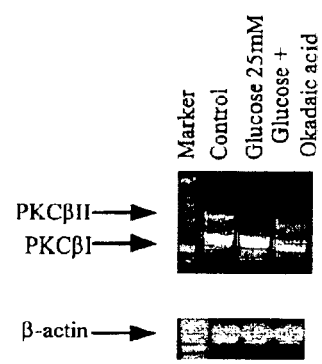
FIG. 33. RT-PCR analysis of PKCβI and -βII mRNA after okadaic acid treatment. Synchronized A10 cells upon re-initiation of the cell cycle with DMEM containing 10% FBS were pre-incubated for 30 minutes with 20 nM okadaic acid followed by the addition of glucose. Total RNA was isolated and RT-PCR was performed on 2 μg of RNA. The first strand cDNA synthesized was amplified using a sense primer to the common, C4, domain and antisense primer to the PKCβI exon. The PCR product size was 187 bp for PKCβI; 404 bp for PKCβII and 550 bp for β-actin. Lane 1:5.5 mM glucose, control cells; lane 2:25 mM glucose and lane 3:25 mM glucose+okadaic acid. Okadaic acid interfered with the ability of glucose to destabilize PKCβII.

To further target downstream pathways involved in PKCβII destabilization by high glucose, synchronize A10 cells were pre-incubated with CG 41251 (5 μM), a PKC inhibitor, PD 98059(20 μM), a MAP kinase kinase (MEK) inhibitor, AG-490 (5 μM), a Janus kinase (JAK) inhibitor, Rapamycin (1 μM), inhibitor of p70/85 S6 kinase signaling pathway or herbimycin A (1 μM), a tyrosine kinase inhibitor. Following re-initiation of the cell cycle with DMEM containing 10% FBS, inhibitors were added to synchronized A10 cells 30 minutes prior to the addition of 5.5 mM glucose (control) or 25 mM glucose (glucose-treated) or 25 mM glucose in addition to the inhibitors. The PKC inhibitor CGP 41251, blocked the action of glucose on PKCβII mRNA destabilization. Hence, PKC could phosphorylate the components involved directly or the process involved protein kinases that require phosphorylation by PKC. Results also indicated the potential involvement of a tyrosine kinase-dependent pathway since herbimycin also prevented PKCβII mRNA destabilization by high glucose. The process was unlikely to be dependent of the MAPK cascade, JAK kinase or p70/85 S6 kinase pathways (FIG. 11) since their putative inhibitors did not block the effects of high glucose.
Involvement of a Reversible Phophorylation Process Extracellular effectors regulate a large number of biological processes by protein phosphorylation-dephosphorylation as an important component of signal transduction cascades. Regulation of cellular functions like gene expression, cell proliferation and differentiation is controlled by a balance between protein kinases (that phosphorylate the substrate) and protein phosphatases (that dephosphorylate) (Jia, 1997, pp.17–26; Barford, 1996, pp.407–412). To further test if phosphatases played a role in this process, okadaic acid (20 nM), a potent inhibitor of protein phosphatase PP-2A and PP-1 was added to synchronized A10 cells 30 minutes prior to the addition of either 5.5 mM of 25 mM glucose. Okadaic acid interfered with ability of glucose to destabilize PKCβII mRNA indicating that the process may be regulated by phosphorylation/dephosphorylation (FIG. 33).

Expression of a pβG-PKCβII Stability Reporter System

To demonstrate whether PKCβII specific exon encoded crucial elements that could confer instability in response to high glucose to other genes, a heterologous chimeric minigene was established. The 404 bp PKCβII cDNA amplified by RT-PCR, using the sense primer to the upstream PKCβ common C4 domain and the antisense primer to the βIV5 domain, resulted from the 216 bp βIIV5 exon inclusion. This PKCβII cDNA was cloned into the pβg vector (kindly provided by N. P. Curthoys, Colo. State University) that encodes a chimeric β-globin/growth hormone mRNA (see FIG. 34). The β-globin coding sequence within the parent pβG vector was followed by a multi-cloning site containing four unique restriction sites, into which the PKCβII cDNA was subcloned in frame at the SpeI and XbaI sites thereby maintaining the 3'UTR and poly(A) tail of the growth hormone.

Figure 35A:
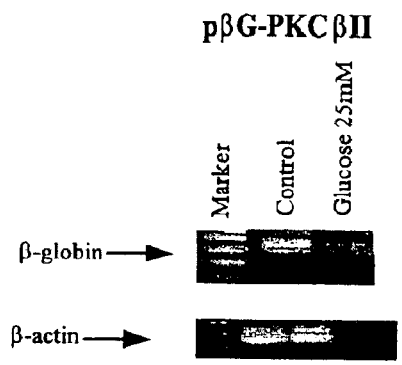
FIGS. 35A and 35B. The pβG-PKCβII chimeric minigene is destabilized by high glucose. The parent vector pβG and pβG-PKCβII minigene were transfected into human aorta smooth muscle cells. Following acute exposure of three hours with high glucose, total RNA was extracted. RT-PCR was then performed on 2 μg of RNA using sense and antisense primers for the β-globin coding region. PCR results for pβG-PKCβII minigene and pβG vector are shown in FIGS. 35A and 35B, respectively.
Figure 35B:
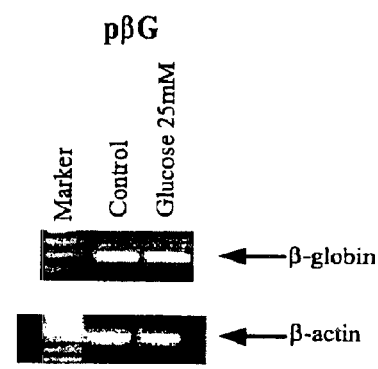

The resulting chimeric minigene pβG-PKCβII was transiently transfected into human aorta smooth muscle cells. The parent vector, pβG, produced a β-globin mRNA whose levels remained unaltered by glucose concentrations as determined by RT-PCR analysis (FIGS. 35A and 35B). Following acute exposure of 3 hours with high glucose (25 mM), an 80% decrease in β-globin mRNA in the AoSMC cells transfected with pβG-PKCβII minigene as compared to incubation with normal (5.5 mM) glucose was observed. As demonstrated by the RT-PCR analysis, FIGS. 35A and 35B, the levels of β-actin mRNA remained constant in both control and glucose-treated AoSMC and A10 cells transfected with pβG-PKCβII stability reporter system. Thus, the introduction of the PKCβII cDNA in a reporter system was sufficient for its down-regulation by exogenous high glucose.

Acute Exposure to High Glucose Destabilizes pβG-PKCβII Minigene

Figure 36A:
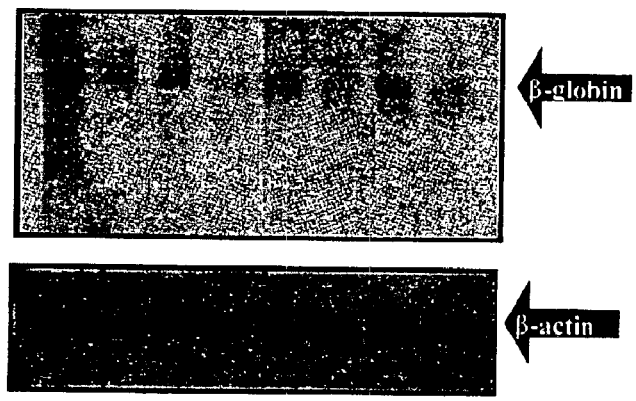
FIGS. 36A and 36B. Half-life analysis of pβG-PKCβII mRNA.
Figure 36B:
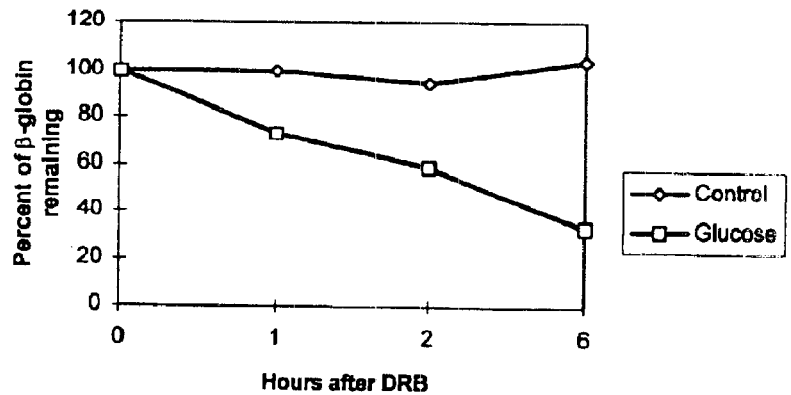
Figure 37:
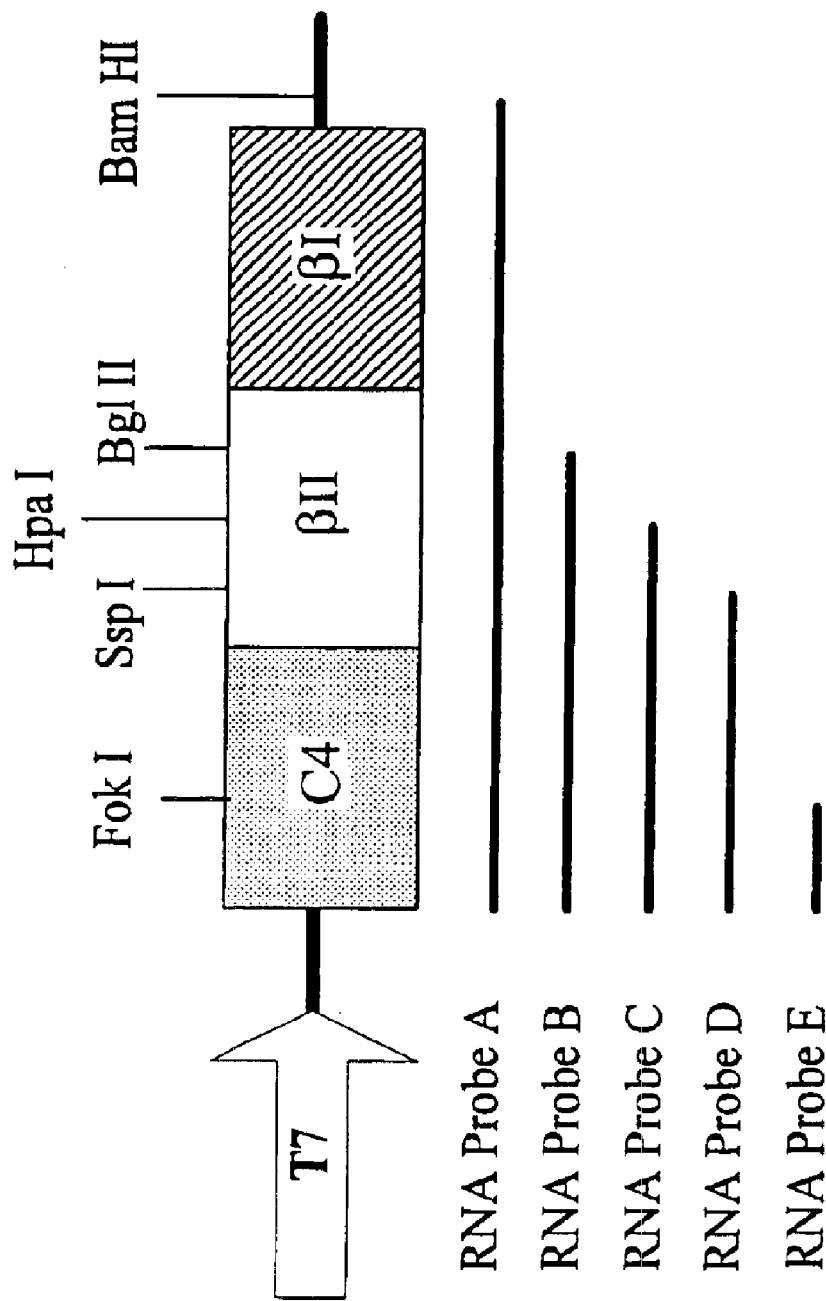
FIG. 37. Schematic of the RNA probes used for the RNA EMSAs. RNA probes A to E and the restriction enzyme cleavage sites used for their generation by T7 RNA polymerase are indicated. Probe A represents the 404 bp PKCβII exon included mRNA and was prepared by linearization with BamH I. Probe B was linearized at 175 bp with Bgl II, probe C was linearized at 137 bp with Hpa I, probe D was linearized at 102 bp with Ssp I while probe E was linearized at 45 bp with Fok I.

To further characterize the instability element, half-life determinations were carried out in the presence of 5,6-dichloro-1-β-D-ribofuranosylbenzimidazole (DRB) to inhibit transcription via RNA polymerase II. A10 cells stably transfected with the pβG-PKCβII stability reporter system and the parent vector, pβG were incubated with DRB and incubated with normal or high (5.5 mM or 25 mM) glucose over a period of 6 hours. Northern blot analysis indicated that the β-globin mRNA of pβG-PKCβII transfected A10 was destabilized within the first 6 hours by high glucose exposure. No changes in the β-actin mRNA levels were observed between normal and high glucose as seen in FIGS. 36A and 36B. In the presence of 25 mM glucose it appears that the mRNA destabilization involves shortening of the mRNA presumably via deadenylation.

Figure 38:
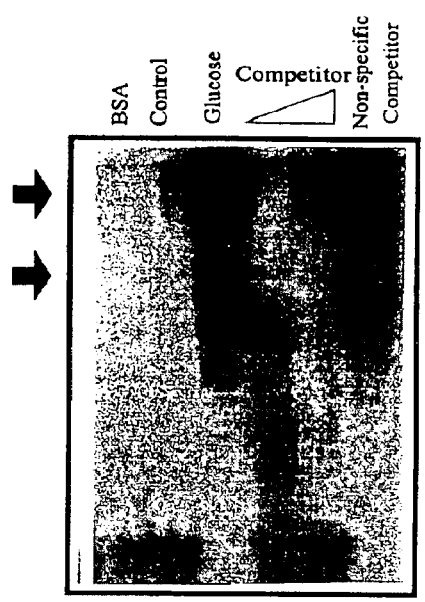
FIG. 38. RNA electrophoretic mobility shift assay using full length PKCβII mRNA probe. $^{32}$P labeled RNA probe A was incubated with 3 μg of cytoplasmic extracts from control cells or glucose-treated cells. The complexes were separated on a 10% polyacrylamide gel, dried and exposed to a Molecular Dynamics Phosphoimaging Screen. RNA-protein binding complexes were observed (black arrows) with glucose-treated A10 cells which was competed out by specific excess unlabeled competitors. Non-specific competitor did not compete for the binding. No binding was observed with BSA. The experiment is representative of results obtained on five separate occasions.
Figure 39:
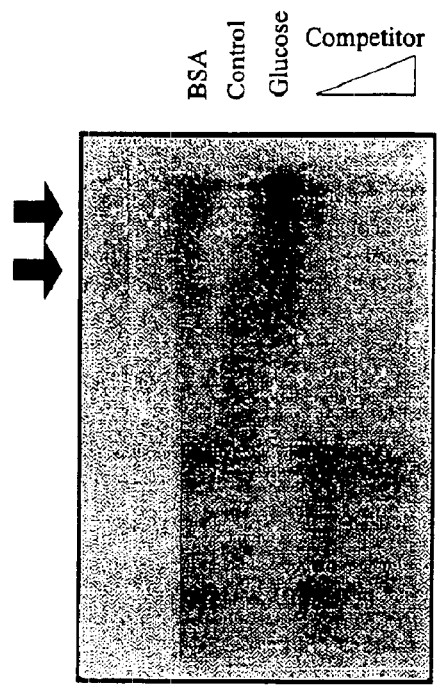
FIG. 39. A cytosolic factor binds to a glucose-regulated element present in the PKCβII coding region. $^{32}$P labeled RNA probes B were incubated with 3 μg of cytoplasmic extracts from control cells or glucose-treated cells. The complexes were separated on a 10% polyacrylamide gel, dried and exposed to a Molecular Dynamics Phosphoimaging Screen. RNA-protein binding complexes were observed (black arrows) with glucose-treated A10 cells using probe B, which was competed out by specific excess unlabeled competitors. No binding was observed with BSA. The experiment is representative of results obtained on five separate occasions.

Cytoplasmic Extracts from Glucose-treated A10 Cells Contain a Protein that Binds to the PKCβII mRNA Causing Its Destabilization Our earlier work with RNA stability assays, had indicated that a nuclease activity involved in PKCβII mRNA destabilization, was present in the cytosolic extract of glucose-treated A10 cells. To ascertain if cytoplasmic extracts from glucose-treated A10 cells contain trans-acting factors which could bind to the cis-elements of PKCβII mRNA, an in vitro transcription vector was produced by cloning PKCβII cDNA into the pCR-Blunt vector (INVITROGEN), upstream of a T7 promoter (FIG. 38). A full length transcript of PKCβII cDNA was in vitro transcribed as described in methods and used in the band shift assays. RNA-protein complex was observed when the labeled RNA probes were incubated with cytoplasmic extracts of glucose-treated A10 cells, binding reaction carried out as described in methods. No complex formation was observed with the control cytoplasmic extracts as shown in (FIG. 39).

To determine if this RNA-protein complex showed specific binding, excess cold competitor RNA probes were added. Binding was eliminated by the specific RNA probes while the non-specific RNA probe did not compete for protein binding.

Glucose-regulated Instability Element is Present within the PKCβII Exon

To further target the site of sequences involved in the glucose-induced destabilization of PKCβII mRNA, restriction digestion of the PKCβI transcript cloned into pCR-blunt vector was performed to generate deletion constructs as described in FIG. 38. RNA gel shift analyses were carried out with probes B, C, D or E incubated with glucose-treated or control cytoplasmic extracts from A10 cells.

RNA-protein binding was observed in glucose-treated cytoplasmic extracts from A10 cells using probe B (FIG. 39) which was linearized at 175 bp with BglII within PKCβII exon such that the PKCβI -specific exon was eliminated. This RNA-protein binding was competed out with excess of the cold RNA probe B.

Figure 40:
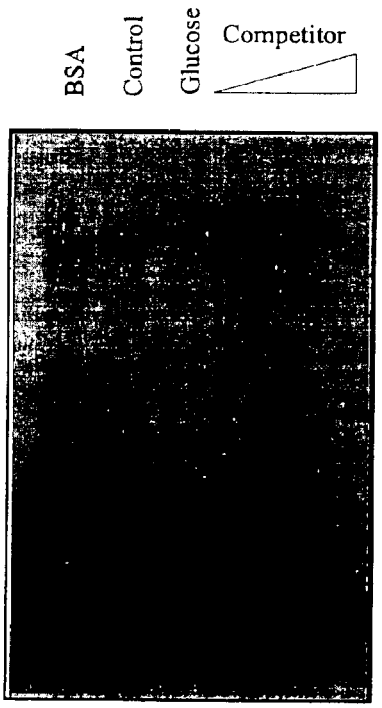
FIG. 40. No RNA protein binding observed using RNA probe C.

No complex formation was observed with RNA probes C (which was linearized at 137 bp with HpaI which cut within the PKCβII-specific exon) incubated with cytoplasmic extracts from A10 cells (FIG. 40). Probes D (linearized at 102 bp with SspI which cut within the PKCβII-specific exon) and E (linearized at 45 bp with FokI which cut within the C4 exon) did not show complex formation (data not shown).

This indicated that the putative glucose-regulated instability element was deleted in probes C, D and E, and hence the sequence with protein-mRNA binding activity may lie between the BglII site (at position 175) and HpaI site (at position 137) within the PKCβ-specific coding region.

UV Cross-linking Detected Associate of Proteins

Figure 41:
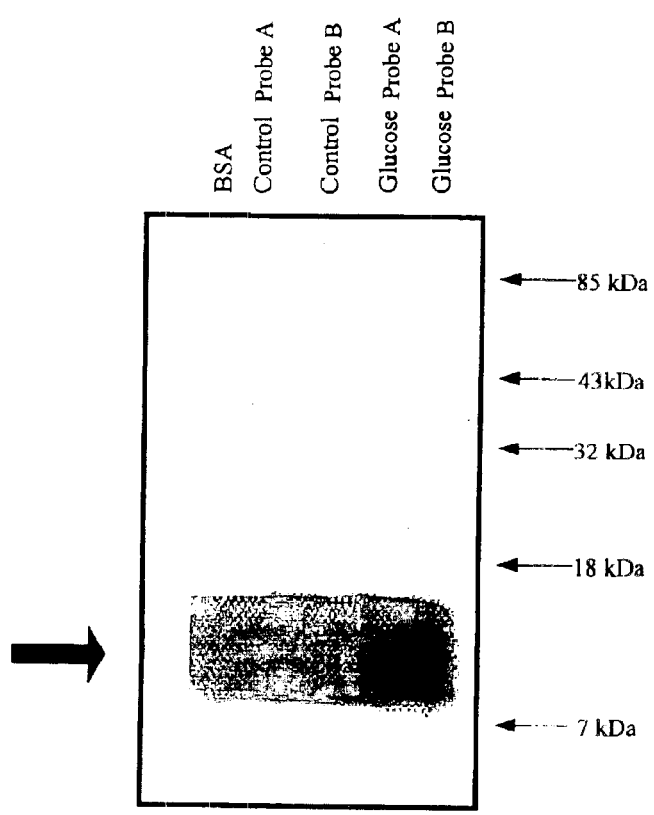
FIG. 41. UV cross-linking analysis of the RNA-protein binding complex. $^{32}$P labeled RNA probes A and B were incubated with 3 μg cytoplasmic extracts from control cells or glucose-treated A10 cells. The unbound RNA was digested with RNase T1 and then exposed to UV radiation. The proteins were resolved by electrophoresis on a SDS-polyacrylamide gel. Gels were dried and exposed to Molecular Dynamics Phosphoimaging Screen. A 10–14 kDa protein was observed to bind to probes A and B in glucose-treated extracts. The experiment is representative of results obtained on five separate occasions.

To provide an insight to the proteins that bind to the PKCβII mRNA in response to high glucose exposure, ultraviolet cross-linking experiments were performed using probes A and B that demonstrated specific binding. The binding reaction was set up as described for the RNA shift assays and subjected to UV light to generate covalent bonds between RNA and the associated proteins. The samples were digested with RNase A and separated by SDS-polyacrylamide gel electrophoresis. A small (~10–14 kD) protein-RNA binding complex was observed (FIG. 41) in glucose-treated cytoplasmic extracts from A10 cells.

Discussion

In this study, several molecular mechanisms by which glucose may regulate PKCβI and -βII gene expression in VSMC were investigated. The elucidation of this regulatory phenomenon is essential since the depletion of PKCβII levels in response to acute hyperglycemia can accelerate cellular proliferation, which may be directly involved in the development of occlusive atherosclerotic lesions. This may occur in addition to the well studied phenomenon of PKCβII activation associated with chronic exposure (10 days to 4 months) of hyperglycemia.

Glucose regulation of PKCβ gene expression in VSMC may occur at transcriptional, post-transcriptional, translational, or post-translational levels. The potential sites of regulation included repression of transcription, improper nuclear export of PKCβII mRNA, post-transcriptional mRNA destabilization, decreased translation or multiple effects culminating in decreased PKCβII protein levels. PKCβII protein levels declined sharply by 6 hours of high glucose exposure while PKCβI protein levels did not change significantly between high and normal glucose conditions. Since protein levels often reflect the amount of mRNA transcribed, steady state levels of PKCβ mRNA were determined. A decrease in PKCβ(I+II) mRNA levels observed in A10 cells exposed to high glucose was likely due to the down-regulation of PKCβgene expression.

Since PKCβI and PKCβII share a common DNA promoter, transcriptional processing of PKCβ in VSMC was examined to determine if high glucose down-regulated PKCβ gene expression by repressing promoter activity. Transactivating factors, which interact on the cis-elements located in the common promoter region of PKCβ gene, could positively or negatively regulate the PKCβ pre-mRNA splicing in response to high glucose. It was possible that glucose affected transactivators to preferentially process PKCβ pre-mRNA splicing to PKCβ mature mRNA. Transcriptional processing of PKCβII in VSMC was first examined to determine if high glucose down-regulated PKCβII mRNA levels by repressing promoter activity. Hyperglycemic conditions, however, only quenched activities of PKCβ promoter constructs rather than repress promoter activity. An example is quenching exerted by the yeast factor GAL80, which inhibits gene activation by the positively acting GALA protein in the galactose regulation of yeast.

This transcriptional effect accounted for only a fraction of the effect of glucose on PKCβI and PKCβII protein levels. Although promoter activities of construct A(–4.1 kb to +179CAT) and construct C(–674 to +179CAT) were decreased by high glucose, promoter activity of construct D (–411 to +179CAT) showed maximum quenching in high glucose. Construct E showed no quenching by high glucose indicating that a potential carbohydrate response element was deleted. Quenching involves the inhibitor interfering with the ability of the activator's activation domain to stimulate transcription. Quenching of transcriptional activity accounted for only a fraction of the effect of high glucose on PKCβI and PKCβII protein levels.

Various positive and negative regulatory cis-elements have been identified on the PKC f gene. TATA box (–530) and CAAT box (–395) are found in the reverse order upstream from the transcription start site, with TATA box position towards 5' end. The distant positions of TATA box and CAAT box from the transcription start site indicated involvement of other regulatory elements for promoter activity. Other cis-acting regulatory elements including octomer binding motif, $AP_1$, $AP_2$, SP1 binding sites and E boxes were also identified. The 5' region is also rich in CG bases. Construct E, containing –111 to +43 sequence, was sufficient for basal promoter activity indicating that neither the TATA box nor CAAT box is essential for promoter activity. One possibility of quenching of promoter activity may be through the $AP_1$ binding site, which has been shown to act as a repressor (Benbow et al, 1997, pp.519–526), present at –442 bases upstream of transcription start site. However, construct D (–411 to +179) in which the $AP_1$ binding site has been deleted, showed maximum quenching in the presence of high glucose indicating that some other mechanism is probably involved in the quenching of PKCβ promoter by glucose.

It is possible that glucose may be exerting its quenching effect through a response element located upstream of the transcription start site. First, a carbohydrate response element (ChoRE) that mediates its action via glucose is known. Second, the consensus sequence, 5' CACGTG 3', has been described in the promoter region of a number of glucose responsive genes including L-PK and S-14 in hepatocytes. Third, CACGTG motif is also the core-binding site for the c-Myc family of transcription factors. Fourth, multimers of the ChoREs of either L-PK or S-14 genes can function independently to support the glucose response. Fifth, multiple copies of CACGTG motif are found in the region upstream of the transcription initiation site of the PKCβ promoter region at positions –318 and –226 with one or two mismatches.

It is therefore likely that glucose plays a role as a quencher of positively acting regulatory factors by binding to or otherwise activating a ChoRE. Construct D contains a ChoRE motif in proximity to the CAAT box and $AP_2$ binding site (TATA box and $AP_1$ binding site have been deleted). The ability of a bound trans-acting factor to stimulate transcription via its activation domain could be inhibited by quenching of the activation domain by glucose which can either bind to trans-acting factors without binding to DNA or bind to a site adjacent to the trans-acting factor (Latchman., 1995, pp.239–278). This may be a possible explanation for the quenching of PKCβ promoter observed in the presence of high glucose.

Since the extent of quenching of the PKCβ promoter activity by high glucose varied at different times, simultaneous cell cycle progression studies were performed. Results indicated that PKCβII levels "cycled" with synchronized A10 cells during the 24 hour period of re-initiation of cell proliferation by serum addition. In the presence of high glucose, PKC16 promoter activity was down regulated at 14 hours (S phase) compared to the up-regulation of promoter activity following G1 phase in normal glucose. Simultaneous [$^3$H]-thymidine uptake studies indicated an increase in the percentage of cells going through S phase following high glucose exposure. A possible explanation for this effect is that PKCβII may function as a "gate-keeper" for DNA synthesis, with increased PKCβII levels attenuating DNA synthesis in VSMC. In the presence of high glucose, the down-regulation of PKCβII allows for more cells to enter S phase. This increased rate of DNA synthesis accounts for the acceleration of proliferation of VSMC. Thus, in hyperglycemic conditions, the down regulation of PKCβII coincides with increased proliferation of VSMC as shown here.

We further investigated whether high glucose affected the post-transcriptional processing of PKCβ transcripts since quenching of PKCβ promoter activity, however, did not fully explain the reduction in PKCβ mRNA levels. A10 cells exposed to high glucose showed a decrease in PKCβ(I+II) mRNA stability within 2 hours in the presence of actinomycin D (an inhibitor of RNA polymerases), indicating an increase in message degradation was also occurring.

Further, the in vitro stability assay demonstrated the induction or activation by glucose of a nuclease activity involved in the destabilization of PKCβII mRNA. This divalent cation-dependent nuclease activity was distinct from cyclizing RNases and acid lysosomal RNase since its activity was inhibited by EDTA. Although it was not possible to exclude the presence of potential lysosomal RNase in the reaction completely, the functional role for this enzyme was eliminated by the observation that the degradation of the transcript required divalent cations. This requirement of divalent cations is the hallmark of ribonucleases that regulate mammalian mRNA turnover.

To confirm that glucose specifically destabilized the PKCβII mRNA isoform, RT-PCR was performed with primers that amplified both PKCβI and PKCβII mRNA simultaneously. High glucose destabilized PKCβII mRNA while PKCβI mRNA was not affected significantly. Since the mature PKCβII mRNA is generated by exon inclusion and both PKCβI and PKCβII transcripts contain the PKCβI exon and share a common 3'UTR, the destabilizing elements appear to be introduced within the PKCβII exon or be introduced around the 5' splice site between the exons. Although stability determinants have been described within the mRNA coding regions of genes like c-myc is the first report of an instability element present within an exon that is regulated by glucose. This is a novel observation since the destabilization elements regulated by glucose occur within the PKCβII exon rather than in the 3'UTR of PKCβII mRNA.

The studies were extended to human aortic smooth muscle cells (AoSMC) and it was demonstrated that glucose induced PKCβII destabilization in primary human cell cultures. The combined effects of high glucose on transcriptional quenching of the PKCβ promoter and specific destabilization of the PKCβII transcript account for the 60–75% reduction of PKCβmRNA levels observed under steady state conditions in rat and human proliferating aortic smooth muscle cells. The human primary cultures further underscore the physiological relevance of acute high glucose effects on vascular smooth muscle cell proliferation.

In other studies, we used CGP53353 a PKCβII-specific inhibitor, to demonstrate that CGP53353 inhibits glucose-stimulated rat VSMC proliferation (Yamamoto et al., 1998b, pp.205–216). These studies confirmed that PKCβII attenuates cell proliferation and predicts that cells expressing PKCβII are more differentiated and less likely to undergo apoptosis. This could provide an explanation towards the observation that vascular smooth muscle cells overexpressing PKCβII are found in the microvasculature of diabetic rats subjected to untreated hyperglycemia for 2 to 4 months.

Here, we studied the effects of high glucose on PKCβI and PKCβII mRNA on synchronized VSMC during the first cell cycle post-synchronization and demonstrated that glucose-induced destabilization of PKCβII mRNA occurs during the course of the cell cycle. Also, instead of PKCβII, the PKCβ2 nomenclature has been used on occasions which would imply that PKCβI was the isoform increased by hyperglycemia.

In none of these studies reflected in the prior art were PKCβ mRNA levels examined within acute glucose exposure. Our present studies examined the regulation exerted by acute glucose exposure on the PKCβ gene and have shown that glucose acted both transcriptionally and post-transcriptionally, with the latter effect accounting for the majority of the down-regulation of PKCβII mRNA.

It was crucial to investigate the mode of glucose action and elucidate potential pathways involved in glucose-induced destabilization of PKCβII mRNA in VSMC. Insulin regulates the alternative splicing of PKCβII mRNA in rat skeletal muscle cells and hence it was essential to investigate the involvement of insulin signaling in the post-transcriptional regulation of PKCβII mRNA by glucose in VSMC. In human aorta smooth muscle cells, glucose destabilizes PKCβII mRNA and not PKCβI mRNA, while insulin did not destabilize PKCβI or -βII mRNA. This implies that the destabilization of PKCβII mRNA by glucose is distinct from the regulation of insulin-induced alternative splicing of PKCβII mRNA. Since insulin enables the uptake of glucose for efficient metabolism in the cell, the implication is that buildup of free glucose in the cytosol may be essential for glucose-induced destabilization of PKCβI mRNA.

Studies with the PKC inhibitor showed that a PKC-dependent pathway may be associated with the destabilization of PKCβII mRNA by high glucose. Insulin is known to activate PKC in VSMC. The finding that insulin did not destabilize PKCβII mRNA suggests that a different activation mechanism may be involved. The PKC inhibitor used here, CGP41251, is not specific for a single PKC isoform. This could imply the presence of a cross-talk between PKC isoforms similar to that between PKCα and PKCδ. They demonstrated that activated PKCα up-regulated the steady-state levels of PKCδ mRNA, which caused an increase in the PKCδ protein level. Protein kinase C is a mediator of signal transduction pathways that alter gene expression. Activation through a PKC-dependent pathway, of transcription factor like AP-1 can be altered by tumor-promoting phorbol esters like 12-O-tetradecanoylphorbol-13-acetate (TPA). For instance, PKC activation by TPA destabilizes PKCδ mRNA via a PKC-dependent pathway in A20 cells.

Using glucose analogs, we showed that glucose need not be metabolized further by glucokinase nor activate the hexose mono-phosphate shunt or the hexosamine biosynthetic pathway. Glucose could destabilize PKCβII mRNA in VSMC without any modification even though it is predominantly present as glucose-6-phosphate in the cell.

Cycloheximide did not block destabilization of PKCβII mRNA by high glucose indicating that de novo protein synthesis is not required. Further, it is known that mRNA half life is linked to translation. Inhibition of translation by cycloheximide results in stabilization of mRNA. Since cycloheximide does not interfere with glucose-induced destabilization of PKCβII mRNA, it suggests that the regulation is independent from translation.

Okadaic acid inhibited the destabilization thereby implying that serine/threonine phosphatases like PP-2A and PP-1 are involved in regulating the process. An inhibitor of PI3-kinase blocked the destabilization of PKCβII mRNA by high glucose implying the involvement of a downstream target of PI3-kinase such as PKC. Further, the lack of effect of inhibitors for the MAPK cascade, JAK kinase or p70/85 S6 kinase suggest that these pathways are not involved in high glucose-induced PKCβII mRNA destabilization in VSMC.

Since acute hyperglycemia destabilized PKCβII mRNA and PKCβI mRNA levels remaining unaltered, it was possible that the putative glucose-responsive instability element resided within the exon encoding PKCβII mRNA. The PKCβII cDNA was cloned into the pCR-blunt vector and its sequence was determined. Restriction digestion and sequencing confirmed that the mature PKCβII mRNA was generated by inclusion of the 216 bp exon.

A heterologous stability reporter system was established in vascular smooth muscle cells to demonstrate that PKCβII exon contains a instability element regulated by high glucose. The chimeric pβG-PKCβII minigene comprises of the parent pβG vector into which the PKCβII cDNA was subcloned in frame with the β-globin exon into the multi-cloning site. pβG vector is a chimera a β-globin/growth hormone such that the multi-cloning site is followed by the 3'UTR and polyadenylation site of the bovine growth hormone. This parent vector was an appropriate choice since the 3'UTR and poly (A) tail, which are common to both PKCβI and -βII mRNA, are eliminated as the determinants of stability. β-globin mRNA was destabilized by acute hyperglycemia in the pβG-PKCβII stably transfected human aorta smooth muscle cells while the β-globin mRNA in the pβG stable transfectants were not affected by extra-cellular high glucose concentrations. This has two implications: (i) the PKCβII cDNA contains a glucose-responsive instability element within its exon; and (ii) the 3'UTR and poly(A) tail—the common determinants of mRNA stability, are not involved in glucose-mediated destabilization of PKCβII mRNA in VSMC. This chimeric gene contains the PKCβII cDNA (404 bp exon) subcloned in frame with the β-globin. The introns and other 3' flanking sequences of PKCβII mRNA are not present. These sequences could play an important role in secondary structure and could contain stability determinants that act mutually to influence the mRNA stability. These sequences are omitted in the chimeric minigene (pβG-PKCβII), and hence a lesser extent of destabilization is observed. It may be possible that the PKCβII exon that is not translated (due to the introduction of a STOP codon) in the mature PKCβII mRNA could act as a longer 3'UTR thereby affecting its stability.

Half-life analysis of the β-globin mRNA in the pβG-PKCβII stable transfectants, using DRB, indicated that glucose destabilized β-globin mRNA within 2 hours of exposure. DRB was preferred as the inhibitor of transcription by polymerase II since actinomycin D was reported to inhibit translation and inhibit mRNA degradation in some instances. This rapid destabilizing effect of acute hyperglycemic further strengthens the hypothesis that the glucose effect is conferred by the instability element present within the PKCβII exon.

Although chimeric mRNAs provide valuable information regarding the sequences affecting the stability of the mRNA, truncated chimeric mRNAs may give misleading information regarding mRNA stability since factors such as translation rate, secondary structure, and intracellular localization may influence their stability. Further, more than one stability determinant may be present in the mRNA which could be regulate its turnover. Hence, to identify the instability elements in PKCβII mRNA regulated by high glucose in VSMC, in vitro binding interactions between RNA and proteins present in the cytosol were observed by RNA mobility shift assays. Cytoplasmic extracts from glucose-treated A10 cells were incubated with varying lengths of in vitro transcribed PKCβII labeled probes. A region between 175 bp and 137 bp in PKCβII cDNA was identified to contain an element that bound to a protein present in the cytoplasm of glucose-treated A10 cells. This region containing the 38 nucleotides corresponds to positions 2127 bp and 2165 bp of the PKCβII cDNA and occurs within the PKCβII coding region. Interestingly, its position is immediately before the STOP codon of the PKCβII exon. This binding site was in close proximity to a stem-loop structure in the PKCβII mRNA. Premature stop codons affect mRNA stability as observed in phytohemaglutinnin mRNA whose stability is decreased by the presence of premature nonsense codons.

Elimination of RNA-binding by competitor probes demonstrated the specificity of the interaction by the instability element without altering the native RNA. Using UV cross-linking, a 10–14 kD protein was identified as binding to probes A and B. The function of this protein could be similar to that of an endoribonuclease as in the case of transferrin receptor or apolipoprotein or an accessory protein aiding in the endoribonucleatic cleavage. For example, recently Canete-Soler et at (Canete-Soler, R., M. L. Schwartz, Y. Hua, and W. W. Schlaepfer.

1998. Characterization of ribonucleoprotein complexes and their binding sites on the neurofilament light subunit mRNA. J. Biol. Chem. 273:12655–12661) described a stability region present within a 68-nt sequence, localized between the 3'UTR and the 3'-coding region of the neurofilament NF-L, that serves as the binding site for a unique ribonucleoprotein complex.

Glucose plays an important regulatory role in the expression of PKCβII in VSMC. Acute high glucose could exert regulatory effects through a putative carbohydrate response element located upstream of the PKCβ transcription start site and through glucose-induced post-transcriptional destabilization of PKCβII massage via a nuclease activity present in the cytosol. In this case, the rate of mRNA degradation plays an important role in establishing levels of gene expression. Although hormones, growth factors and ions are known to induce changes in mRNA stability, here we determined that PKCβII mRNA levels are regulated primarily by mRNA destabilization in response to glucose, a cellular nutrient. This multi-level regulation of gene expression by glucose suggests that PKCβII may play a pivotal role in vascular smooth muscle cell function.

The physiological implications in diabetic patients that suffer from frequent episodes of acute hyperglycemia are profound. Acute hyperglycemia down-regulates PKCβII levels which results in accelerated proliferation of vascular smooth muscle cells and ultimately leading to increased risk of developing atherosclerosis.

In conclusion, this investigation provides molecular insight into the mechanisms involved in the destabilization of PKCβII by high glucose in vascular smooth muscle cells. To our knowledge, this is the first report of identification of instability element present within the PKCβII coding region that is regulated by acute high glucose exposure. The ability of glucose, an important cellular nutrient, to influence mRNA turn-over within acute exposure in vascular SMC further emphasizes its role in regulation of gene expression.

CONCLUSION

Detailed description of the invention: The BII-exon should destabilize a cDNA insert in the presence of high extracellular glucose. For our initial studies, the PBglobin (pBG) vector (obtained from Norman P. Curthoys, Colo. State University) was used (2). The chimeric pBG-BII plasmid was constructed by inserting the PKCBII exon and flanking regions as shown below into the vector at a multicloning site. The vector was created by inserting the PvuII-Bgl II fragment of pSVB10, the protions of the first three exons and the two introns of the rabbit B-globin gene, into the HindII site of the pRc/RSV vector. The B-globin genomic sequence extends from 9 bp upstream of the transcription initiation site to the translation stop codon.

pBG contains a strong viral promoter derived from the long terminal repeat of the *Rouse sarcoma* virus followed by genomic DNA containing the transcriptional start site, the 3' nontranslated region, the full coding sequence and two introns of the rabbit B-globin gene, a MCS with four restriction sites, and the 3' nontranslated region and polyadenylation site of the bovine growth hormone gene. Other chimeric constructs will also be tested such as CAT and luciferase to validate the effect of the BII exon (3). The minimal region of the sequence will be used in tetracycline repressor construct systems (4). The chimeric reporter constructs are tested in a number of cell types. We have found that glucose destabilizes PKCBII mRNA in L6 rat skeletal muscle cells, rat aortic cells, PC12 cells, and other tumerigenic and normal cell lines will also be tested for the ability of glucose to destabilize to chimeric construct.

To further define the minimal boundaries of the cis-elements, a portion of the 3' region of the PKCBII mRNA as diagrammed above was obtained as a 404 bp insert containing the entire 216 bp BII exon and 3' and 5' sequences from the flanking common and BI exon (4). This insert will be restricted be deletion mutagenesis to further limit the amount of mRNA necessary for destabilizing genes of interest.

The cis-acting elements destabilizing mRNA in response to high extracellular glucose were identified by several criteria in the exon encoding the C-terminal 52 amino acids for PKCBII and are shown in FIG. 25. The PKCBII-specific exon is inserted into mature mRNA via alternative splicing of pre-mRNA. The elements inserted may form stem-loop structures providing the secondary structure recognized by destabilizing endonuclese-protein complexes that break A-T bonds (1).

Analysis of PKCBII exon sequences reveals multiple potential cis-acting elements that may be involved in the destabilization of the PKCBII sequence. These elements may form stem-loop structures that are recognized by putative carbohydrate response-acting factors to target the sequence for decay by cytosolic endonucleases (1).

FIG. 28 sets forth an exemplary sequence.

Throughout this specification a variety of references have been cited, each of which is herein incorporated in its respective entirety.

The many features and advantages of the invention are apparent from the detailed specification and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be restored to, falling within the scope of the invention. While the foregoing invention has been described in detail by way of illustration and example of preferred embodiments, numerous modifications, substitutions, and alterations are possible without departing from the scope of the invention defined in the following claims.

What is claimed is:

1. A construct for post-transcriptional control of expression of a gene encoding a protein, wherein said construct comprises a polynucleotide encoding said protein and a polynucleotide encoding a carbohydrate responsive mRNA instability element, wherein said polynucleotide encoding said carbohydrate responsive mRNA instability element comprises the nucleotide sequence of SEQ ID NO:9, and wherein post-transcriptional stability of said carbohydrate responsive mRNA instability element is controlled by said carbohydrate or an analogue thereof.

2. The construct of claim 1, wherein said carbohydrate comprises glucose, 3-O-methylglucose, 2-deoxyglucose, or a combination of any of the foregoing.

3. The construct of claim 1, wherein said carbohydrate comprises glucose.

4. The construct of claim 1, wherein said construct is a plasmid.

5. The construct of claim 1, wherein said construct is a virus.

6. The construct of claim 1, wherein said construct is a retrovirus.

7. The construct of claim 1, wherein said construct is a naked DNA sequence.

8. The construct of claim 1, wherein said protein comprises β-globin.

9. A method of screening for mutations of a carbohydrate responsive mRNA instability element, said method comprising:

obtaining a DNA sample from a subject, wherein said DNA sample comprises the nucleotide sequence of SEQ ID NO:9 or a mutation of said nucleotide sequence;

sequencing said DNA sample; and detecting mutations within said nucleotide sequence.

10. A replicable vector comprising a construct, wherein said construct comprises a polynucleotide encoding a protein and a polynucleotide encoding a carbohydrate responsive mRNA instability element, wherein said polynucleotide encoding said carbohydrate responsive mRNA instability element comprises the sequence of SEQ ID NO:9, and wherein post-transcriptional stability of said carbohydrate responsive mRNA instability element is controlled by said carbohydrate or an analogue thereof.

11. The replicable vector of claim 10, wherein said protein comprises β-globin.

12. A recombinant cell comprising a construct, wherein said construct comprises a polynucleotide encoding a protein and a polynucleotide encoding a carbohydrate responsive mRNA instability element, wherein said polynucleotide encoding said carbohydrate responsive mRNA instability element comprises the nucleotide sequence of SEQ ID NO:9, and wherein post-transcriptional stability of said carbohydrate responsive mRNA instability element is controlled by said carbohydrate or an analogue thereof.

13. The recombinant cell of claim 12, wherein said protein comprises β-globin.

* * * * *

UNITED STATES PATENT AND TRADEMARK OFFICE
CERTIFICATE OF CORRECTION

PATENT NO. : 6,852,529 B1
DATED : February 8, 2005
INVENTOR(S) : Denise R. Cooper and Niketa A. Patel It is certified that error appears in the above-identified patent and that said Letters Patent is hereby corrected as shown below:

Title page, Item [54] and Column 1, line 1,
Title, "GLOUCOSE" should read -- GLUCOSE --.

Title page,
Item [57], ABSTRACT,
Lines 2-3, "ploynucleotide" should read -- polynucleotide --.

Column 1,
Line 10, "are 110 covalently" should read -- are covalently --.
Line 52, "NF-KB" should read -- NFκB --.

Column 2,
Line 34, "–η and –θ are" should read -- –η, and –θ and are --.
Line 38, "γ/t" should read -- λ/ι --.

Column 3,
Line 57, "PKC13" should read -- PKCβ --.
Line 59, "C u or PKD" should read -- C $\mu$ or --.

Column 4,
Line 43, "PKC13" should read -- PKCβ --.
Line 56, "nRNA and" should read -- mRNA and --.
Line 57, "cRNA that" should read -- mRNA that --.

Column 5,
Line 18, "PKC, is" should read -- PKCβ is --.
Line 34, "442" should read -- –442 --.
Line 41, "C 0 gene" should read -- C β gene --.

Column 6,
Line 51, "Element (ChORE)" should read -- Element (ChoRE) --.

Column 9,
Line 2, "isozymes and 4 are" should read -- isozymes –β and –δ are --.
Line 21, "24 ours" should read -- 24 hours --.

Column 15,
Line 42, "PKC, sequence" should read -- PKCβ sequence --.

UNITED STATES PATENT AND TRADEMARK OFFICE
CERTIFICATE OF CORRECTION

PATENT NO.    : 6,852,529 B1
DATED         : February 8, 2005
INVENTOR(S)   : Denise R. Cooper and Niketa A. Patel It is certified that error appears in the above-identified patent and that said Letters Patent is hereby corrected as shown below:

Column 17,
Line 56, "(lane 1), mM" should read -- (lane 1), 25 mM --.
Line 64, "6075% decrease" should read -- 60–75% decrease --.

Column 18,
Line 5, "PKC," should read -- PKCβ --.
Line 10, "PKC," should read -- PKCβ --.
Line 20, "CAT/l -galactosidase" should read -- CAT/β-galactosidase --.
Line 54, "$^{32}$P_labeled PKC," should read -- $^{32}$P-labeled PKCβ --.

Column 19,
Line 4, "50/1 total" should read -- 50µl total --.
Line 66, "or mM glucose" should read -- or 25 mM glucose --.

Column 20,
Line 25, "PKCβI" should read -- PKCβII --.

Column 21,
Line 5, "P-globin" should read -- β-globin --.
Line 24, "50 g/ml DRB" should read -- 50 µg/ml DRB --.

Column 23,
Lines 48-49, "pβG-PKCβI" should read -- pβG-PKCβII --.

Column 25,
Line 30, "swell plates" should read -- 6-well plates --.
Line 63, "(10 ng)" should read -- (10 µg) --.

Column 27,
Line 58, "O-globin" should read -- β-globin --.
Line 59, "Xba!" should read -- XbaI --.
Line 67, "PKC," should read -- PKCβ --.

Column 28,
Lines 62-63, "TGF-01, TGF-162" should read -- TGF-β1, TGF-β2 --.

Column 30,
Line 10, "PKCβI" should read -- PKCβII --.

UNITED STATES PATENT AND TRADEMARK OFFICE
CERTIFICATE OF CORRECTION

PATENT NO. : 6,852,529 B1
DATED : February 8, 2005
INVENTOR(S) : Denise R. Cooper and Niketa A. Patel It is certified that error appears in the above-identified patent and that said Letters Patent is hereby corrected as shown below:

Column 31,
Line 51, "in 50l total" should read -- in 50µl total --.

Column 32,
Line 13, "rather than PKCβII" should read -- rather than PKCβI --.
Line 14, "PKCβI" should read -- PKCβII --.

Column 33,
Line 15, "PKCβI" should read -- PKCβII --.
Line 36, "on PKCβII and" should read -- on PKCβI and --.

Column 37,
Line 45, "PKCβII" should read -- PKCβ --.
Line 67, "PKC f gene" should read -- PKCβ gene --.

Column 38,
Line 54, "PKC 16" should read -- PKCβ --.

Column 40,
Line 62, "p70185" should read -- p70/85 --.

Column 41,
Line 36, "PKCβII" should read -- PKCβI --.

Signed and Sealed this

Twenty-third Day of August, 2005

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Tyrosine phosphatase conserved active-site
      motif
<220> FEATURE:
<221> NAME/KEY: MISC_FEATURE
<222> LOCATION: (2)..(6)
<223> OTHER INFORMATION: Xaa = any amino acid residue

<400> SEQUENCE: 1

Cys Xaa Xaa Xaa Xaa Xaa Arg
1               5

<210> SEQ ID NO 2
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Tyrosine phosphatase signature sequence motif
<220> FEATURE:
<221> NAME/KEY: MISC_FEATURE
<222> LOCATION: (1)..(1)
<223> OTHER INFORMATION: Xaa = Ile or Val
<220> FEATURE:
<221> NAME/KEY: MISC_FEATURE
<222> LOCATION: (4)..(4)
<223> OTHER INFORMATION: Xaa = any amino acid residue
```

```
<220> FEATURE:
<221> NAME/KEY: MISC_FEATURE
<222> LOCATION: (7)..(7)
<223> OTHER INFORMATION: Xaa = any amino acid residue
<220> FEATURE:
<221> NAME/KEY: MISC_FEATURE
<222> LOCATION: (10)..(10)
<223> OTHER INFORMATION: Xaa = Ser or Thr

<400> SEQUENCE: 2

Xaa His Cys Xaa Ala Gly Xaa Gly Arg Xaa Gly
1               5                   10

<210> SEQ ID NO 3
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Dual-specificity phosphatase signature sequence
      motif
<220> FEATURE:
<221> NAME/KEY: MISC_FEATURE
<222> LOCATION: (3)..(4)
<223> OTHER INFORMATION: Xaa = any amino acid residue
<220> FEATURE:
<221> NAME/KEY: MISC_FEATURE
<222> LOCATION: (6)..(7)
<223> OTHER INFORMATION: Xaa = any amino acid residue
<220> FEATURE:
<221> NAME/KEY: MISC_FEATURE
<222> LOCATION: (9)..(9)
<223> OTHER INFORMATION: Xaa = Ser or Thr

<400> SEQUENCE: 3

His Cys Xaa Xaa Gly Xaa Xaa Arg Xaa
1               5

<210> SEQ ID NO 4
<211> LENGTH: 33
<212> TYPE: DNA
<213> ORGANISM: Artificial Sequence
<220> FEATURE:
<223> OTHER INFORMATION: PKC-Beta-I and PKC-Beta-II upstream sense
      primer

<400> SEQUENCE: 4
cgtatatgcg gccgcgttgt gggcctgaag ggg                               33

<210> SEQ ID NO 5
<211> LENGTH: 33
<212> TYPE: DNA
<213> ORGANISM: Artificial Sequence
<220> FEATURE:
<223> OTHER INFORMATION: PKC-Beta-I downstream antisense primer

<400> SEQUENCE: 5
gcattctagt cgacaagagt ttgtcagtgg gag                               33

<210> SEQ ID NO 6
<211> LENGTH: 21
<212> TYPE: DNA
<213> ORGANISM: Artificial Sequence
<220> FEATURE:
<223> OTHER INFORMATION: Beta-globin sense primer

<400> SEQUENCE: 6
gcatctgtcc agtgaggaga a                                            21
```

<210> SEQ ID NO 7
<211> LENGTH: 21
<212> TYPE: DNA
<213> ORGANISM: Artificial Sequence
<220> FEATURE:
<223> OTHER INFORMATION: Beta-globin antisense primer

<400> SEQUENCE: 7
aaccagcacg ttgcccagga g                                          21

<210> SEQ ID NO 8
<211> LENGTH: 351
<212> TYPE: DNA
<213> ORGANISM: Homo sapiens

<400> SEQUENCE: 8
ttttaaacca aaagcttttt gggcgaaacg ctgaaacttc gaccggtttt tcacccgcca    60
tccaccagtc ctaacacctc cgaccaggaa gtcatcagga atattgacca atcagaattc   120
gaaggatttc ctttgttaac tctgaatttt taaaacccga agtcaagagc tagtagatct   180
gtagacctcc gtccttcatt tctgtcattc aagctcacag ctatcatgag agacaagcga   240
gacacctcca acttcgacaa aagttcacca ggcagcctgt ggaactgact cccactgaca   300
aactctgtcg actagaatgc cctgaattct gcagatatcc atcacactgc g           351

<210> SEQ ID NO 9
<211> LENGTH: 39
<212> TYPE: DNA
<213> ORGANISM: Homo sapiens

<400> SEQUENCE: 9
taactctgaa ttttaaaac ccgaagtcaa gagctagta                          39

<210> SEQ ID NO 10
<211> LENGTH: 300
<212> TYPE: RNA
<213> ORGANISM: Homo sapiens

<400> SEQUENCE: 10
uuuuaaacca aaagcuuuuu gggcgaaacg cugaaacuuc gaccgguuuu ucacccgcca    60
uccaccaguc cuaacaccuc cgaccaggaa gucaucagga auauugacca aucagaauuc   120
gaaggauuuc cuuuguuaac ucugaauuuu uaaaacccga agucaagagc uaguagaucu   180
guagaccucc guccuucauu ucugucauuc aagcucacag cuaucaugag agacaagcga   240
gacaccucca acuucgacaa aaguucacca ggcagccugu ggaacugacu cccacugaca   300

<210> SEQ ID NO 11
<211> LENGTH: 175
<212> TYPE: RNA
<213> ORGANISM: Homo sapiens

<400> SEQUENCE: 11
uuuuaaacca aaagcuuuuu gggcgaaacg cugaaacuuc gaccgguuuu ucacccgcca    60
uccaccaguc cuaacaccuc cgaccaggaa gucaucagga auauugacca aucagaauuc   120
gaaggauuuc cuuuguuaac ucugaauuuu uaaaacccga agucaagagc uagua        175

<210> SEQ ID NO 12
<211> LENGTH: 137
<212> TYPE: RNA
<213> ORGANISM: Homo sapiens -continued

```
<400> SEQUENCE: 12
uuuuaaacca aaagcuuuuu gggcgaaacg cugaaacuuc gaccgguuuu ucacccgcca      60
uccaccaguc cuaacaccuc cgaccaggaa gucaucagga auauugacca aucagaauuc     120
gaaggauuuc cuuuguu                                                    137

<210> SEQ ID NO 13
<211> LENGTH: 25
<212> TYPE: PRT
<213> ORGANISM: Homo sapiens
<220> FEATURE:
<221> NAME/KEY: MISC_FEATURE
<222> LOCATION: (1)..(25)
<223> OTHER INFORMATION: Protein kinase ATP-binding motif
<220> FEATURE:
<221> NAME/KEY: MISC_FEATURE
<222> LOCATION: (1)..(1)
<223> OTHER INFORMATION: Xaa = any amino acid residue
<220> FEATURE:
<221> NAME/KEY: MISC_FEATURE
<222> LOCATION: (3)..(3)
<223> OTHER INFORMATION: Xaa = any amino acid residue
<220> FEATURE:
<221> NAME/KEY: MISC_FEATURE
<222> LOCATION: (5)..(6)
<223> OTHER INFORMATION: Xaa = any amino acid residue
<220> FEATURE:
<221> NAME/KEY: MISC_FEATURE
<222> LOCATION: (8)..(25)
<223> OTHER INFORMATION: Xaa = any amino acid residue

<400> SEQUENCE: 13

Xaa Gly Xaa Gly Xaa Xaa Gly Xaa Xaa Xaa Xaa Xaa Xaa Xaa Xaa
1               5                   10                  15

Xaa Xaa Xaa Xaa Xaa Xaa Xaa Lys Xaa
            20                  25
```